(12) United States Patent
Zhou et al.

(10) Patent No.: US 10,801,062 B2
(45) Date of Patent: Oct. 13, 2020

(54) METHODS AND SYSTEMS FOR SEQUENCING LONG NUCLEIC ACIDS

(75) Inventors: Wei Zhou, Saratoga, CA (US); Rui Mei, Santa Clara, CA (US); Filip Crnogorac, Palo Alto, CA (US); Guochun Liao, Belmont, CA (US); Julian Lucas, Davis, CA (US)

(73) Assignee: Centrillion Technology Holdings Corporation, Grand Cayman (KY)

( * ) Notice: Subject to any disclaimer, the term of this patent is extended or adjusted under 35 U.S.C. 154(b) by 1481 days.

(21) Appl. No.: 14/009,089

(22) PCT Filed: Apr. 2, 2012

(86) PCT No.: PCT/US2012/000185
§ 371 (c)(1),
(2), (4) Date: Jul. 3, 2014

(87) PCT Pub. No.: WO2012/134602
PCT Pub. Date: Oct. 4, 2012

(65) Prior Publication Data
US 2014/0315724 A1    Oct. 23, 2014

Related U.S. Application Data

(63) Continuation of application No. 13/153,218, filed on Jun. 3, 2011, now abandoned.

(60) Provisional application No. 61/470,497, filed on Apr. 1, 2011, provisional application No. 61/477,173, filed on Apr. 20, 2011, provisional application No. 61/489,662, filed on May 24, 2011.

(51) Int. Cl.
*C12Q 1/68* (2018.01)
*C12Q 1/6869* (2018.01)
*C12Q 1/6874* (2018.01)

(52) U.S. Cl.
CPC ......... *C12Q 1/6869* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 4,437,975 A | 3/1984 | Gillespie et al. | |
| 4,458,066 A | 7/1984 | Caruthers et al. | |
| 4,469,863 A | 9/1984 | Ts'o et al. | |
| 4,683,195 A | 7/1987 | Mullis et al. | |
| 4,683,202 A | 7/1987 | Mullis | |
| 4,883,750 A | 11/1989 | Whiteley et al. | |
| 4,988,617 A | 1/1991 | Landegren et al. | |
| 5,034,506 A | 7/1991 | Summerton et al. | |
| 5,143,854 A | 9/1992 | Pirrung et al. | |
| 5,216,141 A | 6/1993 | Benner | |
| 5,234,809 A | 8/1993 | Boom et al. | |
| 5,235,033 A | 8/1993 | Summerton et al. | |
| 5,242,794 A | 9/1993 | Whiteley et al. | |
| 5,386,023 A | 1/1995 | Sanghvi et al. | |
| 5,409,818 A | 4/1995 | Davey et al. | |
| 5,413,909 A | 5/1995 | Bassam et al. | |
| 5,470,705 A | 11/1995 | Grossman et al. | |
| 5,494,810 A | 2/1996 | Barany et al. | |
| 5,547,839 A | 8/1996 | Dower et al. | |
| 5,554,517 A | 9/1996 | Davey et al. | |
| 5,578,832 A | 11/1996 | Trulson et al. | |
| 5,602,240 A | 2/1997 | De Mesmaeker et al. | |
| 5,631,734 A | 5/1997 | Stern et al. | |
| 5,637,684 A | 6/1997 | Cook et al. | |
| 5,644,048 A | 7/1997 | Yau | |
| 5,705,628 A | 1/1998 | Hawkins | |
| 5,756,285 A * | 5/1998 | Fuller ................. | C12Q 1/6869 435/196 |
| 5,800,992 A | 9/1998 | Fodor et al. | |
| 5,834,758 A | 11/1998 | Trulson et al. | |
| 5,837,832 A | 11/1998 | Chee et al. | |
| 5,856,092 A | 1/1999 | Dale et al. | |
| 5,861,245 A | 1/1999 | Mcclelland et al. | |
| 5,871,928 A | 2/1999 | Fodor et al. | |
| 5,874,219 A | 2/1999 | Rava et al. | |
| 5,902,723 A | 5/1999 | Dower et al. | |
| 5,936,324 A | 8/1999 | Montagu | |
| 5,981,956 A | 11/1999 | Stern | |
| 6,025,601 A | 2/2000 | Trulson et al. | |

(Continued)

FOREIGN PATENT DOCUMENTS

DE    10149786 A1    7/2003
DE    10214395 A1    10/2003

(Continued)

OTHER PUBLICATIONS

Bentley et al. Accurate whole human genome sequencing using reversible terminator chemistry. Nature. Nov. 6, 2008; 456(7218):53-9.*

Bentley et al. Supplementary Information. pp. 1-55, Nature. Nov. 6, 2008; 456(7218):53-9.*

Guo J, Yu L, Turro NJ, Ju J. An integrated system for DNA sequencing by synthesis using novel nucleotide analogues. Acc Chem Res. Apr. 20, 2010; 43(4):551-63.*

Pan Z, Li Y, Xiao P, Lu Z. Multiple hybridization-extension sequencing (MHES) on microarray. J Biochem. Nov. 2007; 142(5):605-11. Epub Sep. 7, 2007.*

(Continued)

*Primary Examiner* — Teresa E Strzelecka
*Assistant Examiner* — Olayinka A Oyeyemi
(74) *Attorney, Agent, or Firm* — Wilson Sonsini Goodrich & Rosati

(57) ABSTRACT

The present invention provides methods and systems for sequencing long nucleic acid fragments. In one aspect of the invention, methods, systems and reagent kits are provided for sequencing nucleic acid target sequences. Some embodiments of the methods, systems and reagent kits are particularly suitable for sequencing a large number of fragments, particularly long fragments.

15 Claims, 24 Drawing Sheets

Specification includes a Sequence Listing.

(56) References Cited

U.S. PATENT DOCUMENTS

| | | | |
|---|---|---|---|
| 6,045,996 A | 4/2000 | Cronin et al. |
| 6,063,603 A | 5/2000 | Davey et al. |
| 6,090,555 A | 7/2000 | Fiekowsky et al. |
| 6,141,096 A | 10/2000 | Stern et al. |
| 6,185,030 B1 | 2/2001 | Overbeck |
| 6,201,639 B1 | 3/2001 | Overbeck |
| 6,214,246 B1 | 4/2001 | Craighead |
| 6,218,803 B1 | 4/2001 | Montagu et al. |
| 6,225,625 B1 | 5/2001 | Pirrung et al. |
| 6,267,872 B1 | 7/2001 | Akeson et al. |
| 6,361,947 B1 | 3/2002 | Dong et al. |
| 6,386,749 B1 | 5/2002 | Watts et al. |
| 6,391,592 B1 | 5/2002 | Su et al. |
| 6,391,623 B1 | 5/2002 | Besemer et al. |
| 6,410,276 B1 | 6/2002 | Burg et al. |
| 6,440,662 B1 | 8/2002 | Gerwen et al. |
| 6,464,842 B1 | 10/2002 | Golovchenko et al. |
| 6,518,189 B1 | 2/2003 | Chou |
| 6,548,810 B2 | 4/2003 | Zaluzec et al. |
| 6,582,938 B1 | 6/2003 | Su et al. |
| 6,627,067 B1 | 9/2003 | Branton et al. |
| 6,632,611 B2 | 10/2003 | Su et al. |
| 6,673,615 B2 | 1/2004 | Denison et al. |
| 6,685,841 B2 | 2/2004 | Lopez et al. |
| 6,787,308 B2 | 9/2004 | Balasubramanian et al. |
| 6,833,246 B2 | 12/2004 | Balasubramanian |
| 6,852,487 B1 | 2/2005 | Barany et al. |
| 6,872,529 B2 | 3/2005 | Su et al. |
| 6,897,023 B2 | 5/2005 | Fu et al. |
| 6,958,225 B2 | 10/2005 | Dong et al. |
| 6,969,488 B2 | 11/2005 | Bridgham et al. |
| 7,001,724 B1 | 2/2006 | Greenfield et al. |
| 7,189,503 B2 | 3/2007 | Akeson et al. |
| 7,217,562 B2 | 5/2007 | Cao et al. |
| 7,238,485 B2 | 7/2007 | Akeson et al. |
| 7,258,838 B2 | 8/2007 | Li et al. |
| 7,267,966 B2 | 9/2007 | Dong et al. |
| 7,297,778 B2 | 11/2007 | Matsuzaki et al. |
| 7,300,788 B2 | 11/2007 | Matsuzaki et al. |
| 7,689,022 B2 | 3/2010 | Weiner et al. |
| 9,328,382 B2 | 5/2016 | Drmanac et al. |
| 9,689,032 B2 | 6/2017 | Zhou et al. |
| 2002/0012930 A1 | 1/2002 | Rothberg et al. |
| 2003/0022207 A1 | 1/2003 | Balasubramanian et al. |
| 2003/0044781 A1 | 3/2003 | Korlach et al. |
| 2003/0058629 A1 | 3/2003 | Hirai et al. |
| 2003/0064376 A1 | 4/2003 | Makarov et al. |
| 2003/0064398 A1 | 4/2003 | Barnes |
| 2003/0100102 A1 | 5/2003 | Rothberg et al. |
| 2003/0148344 A1 | 8/2003 | Rothberg et al. |
| 2003/0186279 A1 | 10/2003 | Kennedy et al. |
| 2003/0186280 A1 | 10/2003 | Kennedy |
| 2004/0072217 A1 | 4/2004 | Kennedy |
| 2004/0106130 A1 | 6/2004 | Besemer et al. |
| 2004/0248144 A1 | 12/2004 | Mir |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0186576 A1 | 8/2005 | Chan et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0275782 A1* | 12/2006 | Gunderson .......... C12Q 1/6837 435/6.12 |
| 2007/0065816 A1 | 3/2007 | Dong et al. |
| 2007/0128649 A1 | 6/2007 | Young et al. |
| 2008/0102504 A1 | 5/2008 | Akeson et al. |
| 2008/0171316 A1 | 7/2008 | Golovchenko et al. |
| 2008/0248561 A1 | 10/2008 | Golovchenko et al. |
| 2009/0018024 A1 | 1/2009 | Church et al. |
| 2009/0088327 A1 | 4/2009 | Rigatti et al. |
| 2009/0203085 A1 | 8/2009 | Kurn et al. |
| 2009/0291475 A1 | 11/2009 | Lao et al. |
| 2010/0029498 A1 | 2/2010 | Gnirke et al. |
| 2010/0143900 A1 | 6/2010 | Peluso et al. |
| 2010/0173303 A1* | 7/2010 | Ronaghi .............. C12Q 1/6874 435/6.1 |
| 2010/0297706 A1 | 11/2010 | Lee et al. |
| 2010/0330570 A1* | 12/2010 | Vander Horn ....... C12Q 1/6827 435/6.11 |
| 2011/0009276 A1* | 1/2011 | Vermaas .............. C12Q 1/6874 506/7 |
| 2011/0319276 A1* | 12/2011 | Liu ....................... C07H 19/10 506/7 |
| 2012/0083417 A1 | 4/2012 | Zhou et al. |
| 2012/0252682 A1 | 10/2012 | Zhou et al. |
| 2014/0065604 A1 | 3/2014 | Zhou et al. |
| 2014/0186940 A1 | 7/2014 | Goel |
| 2016/0046985 A1 | 2/2016 | Drmanac et al. |
| 2016/0168632 A1 | 6/2016 | Edwards |
| 2016/0237486 A1 | 8/2016 | Zhou et al. |
| 2017/0022554 A1 | 1/2017 | Drmanac et al. |

FOREIGN PATENT DOCUMENTS

| | | | |
|---|---|---|---|
| DE | 10356837 A1 | 6/2005 | |
| DE | 10 2004 009 704 A1 | 9/2005 | |
| DE | 10 2004 025 744 A1 | 12/2005 | |
| DE | 10 2004 025 745 A1 | 12/2005 | |
| DE | 10 2004 025 746 A1 | 12/2005 | |
| DE | 10 2004 025 694 A1 | 2/2006 | |
| DE | 10 2004 025 695 A1 | 2/2006 | |
| DE | 10 2004 025 696 A1 | 2/2006 | |
| GB | 2398383 A | 8/2004 | |
| WO | WO 1988/10315 A1 | 12/1988 | |
| WO | WO 1990/06995 A1 | 6/1990 | |
| WO | WO96/40999 * | 12/1996 | .............. C12Q 1/68 |
| WO | WO 1996/40999 A1 | 12/1996 | |
| WO | WO 1999/47964 A1 | 9/1999 | |
| WO | WO09964437 * | 12/1999 | .............. C12Q 1/68 |
| WO | WO00123610 * | 4/2001 | .............. C12Q 1/68 |
| WO | WO 01/32930 A1 | 5/2001 | |
| WO | WO 02/29003 A2 | 4/2002 | |
| WO | WO 2002/088382 | 11/2002 | |
| WO | WO 2003/020968 | 3/2003 | |
| WO | WO 2003/031947 | 4/2003 | |
| WO | WO 2005/044836 | 5/2005 | |
| WO | WO 2008/066245 A1 | 6/2008 | |
| WO | WO 09/097626 A2 | 8/2009 | |
| WO | WO2010/075188 * | 7/2010 | .............. C12Q 1/68 |
| WO | WO 2010/075188 A2 | 7/2010 | |
| WO | WO 2011/032040 A1 | 3/2011 | |
| WO | WO-2012040624 A1 | 3/2012 | |
| WO | WO-2012106546 A2 | 8/2012 | |
| WO | WO-2012134602 A2 | 10/2012 | |
| WO | WO-2015017759 A1 | 2/2015 | |

OTHER PUBLICATIONS

Shendure J, Ji H. Next-generation DNA sequencing. Nat Biotechnol. Oct. 2008; 26(10):1135-45.*

Yang Z, Sismour AM, Benner SA. Nucleoside alpha-thiotriphosphates, polymerases and the exonuclease III analysis of oligonucleotides containing phosphorothioate linkages. Nucleic Acids Res. 2007; 35(9):3118-27. Epub Apr. 22, 2007.*

Slatko BE, Albright LM, Tabor S, Ju J. DNA sequencing by the dideoxy method. Curr Protoc Mol Biol. May 2001; Chapter 7: Unit7.4A. pp. 1-39. (Year: 2001).*

U.S. Appl. No. 60/011,359, filed Feb. 9, 1996, Barany et al.

U.S. Appl. No. 60/364,731, filed Mar. 15, 2002, Weiner et al.

"Mammal," (Wikipedia.com; accessed Sep. 22, 2011.

"Virus," Wikipedia.com, accessed Apr. 18, 2012.

European search report and written opinion dated May 15, 2014 for EP Application No. 11827648.4.

How many species of bacteria are there? Wisegeek.com. Accessed Sep. 23, 2011.

International search report and written opinion dated Jan. 18, 2012 for PCT/US2011/053079.

(56) References Cited

OTHER PUBLICATIONS

Ivashuta, et al. Linear amplification coupled with controlled extension as a means of probe amplification in a cDNA array and gene expression analysis during cold acclimation in alfalfa (*Medicago sativa* L.). J Exp Bot. Feb. 2002; 53(367): 351-9.
Newton, et al. The production of PCR products with 5' single-stranded tails using primers that incorporate novel phosphoramidite intermediates. Nucleic Acids Res. Mar. 11, 1993;21(5):1155-62.
Office action dated Mar. 13, 2013 for U.S. Appl. No. 13/243,833.
Office action dated Jul. 27, 2012 for U.S. Appl. No. 13/243,833.
Office action dated Nov. 17, 2014 for U.S. Appl. No. 13/970,321.
Ronaghi, M. Pyrosequencing sheds light on DNA sequencing. Genome Res. Jan. 2001; 11(1): 3-11. Review.
Schultz, et al. Single-target molecule detection with nonbleaching multicolor optical immunolabels. Proc Natl Acad Sci U S A. Feb. 1, 2000;97(3):996-1001.
Seo, et al. Four-color DNA sequencing by synthesis on a chip using photocleavable fluorescent nucleotides. Proc. Natl. Acad. Sci. USA. Apr. 26, 2005; 102(17):5926-5931.
Office action dated Feb. 13, 2015 for CN Application No. 201180056235.7 (with English translation).
"Fish," (Wikipedia.com, accessed Nov. 2, 2014).
"Fungi," (Wikipedia.com; accessed Jun. 3, 2013).
"How many species of bacteria are there" (wisegeek.com; accessed Jan. 21, 2014).
"List of sequenced bacterial genomes" (Wikipedia.com; accessed Jan. 24, 2014).
"Murinae," (Wikipedia.com, accessed Mar. 18, 2013).
"Plant," (Wikipedia.com; accessed Mar. 8, 2013).
"Viruses" (Wikipedia.com, accessed Nov. 24, 2012).
Office action dated Jun. 29, 2015 for U.S. Appl. No. 13/243,833.
Office action dated Jun. 18, 2015 for CN Application No. 201280027272.X.
European office action dated Aug. 12, 2015 for EP Application No. 11827648-4.
Office action dated Sep. 28, 2015 for U.S. Appl. No. 13/970,321.
Office action dated Sep. 29, 2015 for CN Application No. 201180056235.7.
Co-pending U.S. Appl. No. 14/970,435, filed Dec. 15, 2015.
U.S. Appl. No. 09/916,135, filed Jul. 25, 2001, Matsuzaki et al.
Adams, et al. The Genome Sequence of *Drosophila melanogaster*. Science. Mar. 24, 2000; 287 (5461): 2185-2195.
Constans, et al. Beyond Sanger: Toward the $1,000 Genome.The Scientist. Jun. 30, 2003; 17(13): 36.
European search report and written opinion dated Sep. 18, 2014 for European Patent Application No. 12762821.2.
Dempcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.
Dong, et al. Flexible use of high-density oligonucleotide arrays for single-nucleotide polymorphism discovery and validation. Genome Res. Aug. 2001;11(8):1418-24.
Gao, et al. Oligonucleotide synthesis using solution photogenerated acids. J. Am. Chem. Soc. 1999; 120: 12698-12699.
Grossman, et al. High-density multiplex detection of nucleic acid sequences: oligonucleotide ligation assay and sequence-coded separation. Nucleic Acids Res. Oct. 25, 1994;22(21):4527-34.

Guo, et al. Four-color DNA sequencing with 3'-0-modified nucleotide reversible terminators and chemically cleavable fluorescent dideoxynucleotides. Proc Natl Acad Sci U S A. 2008. 105(27):9145-50. Epub Jun. 30, 2008.
International search report and written opinion dated Oct. 1, 2012 for PCT/US2012/000185.
Jenkins, et al. The Biosynthesis of Carbocyclic Nucleosides. Chem. Soc. Rev. 1995; 169-176.
Letsinger, et al. Effects of pendant groups at phosphorus on binding properties of d-ApA analogues. Nucleic Acids Res. Apr. 25, 1986;14(8):3487-99.
Levene, et al. Zero-mode waveguides for single-molecule analysis at high concentrations. Science. Jan. 31, 2003;299(5607):682-6.
Mag, et al. Synthesis and selective cleavage of an oligodeoxynucleotide containing a bridged internucleotide 5'-phosphorothioate linkage. Nucleic Acids Res. Apr. 11, 1991;19(7):1437-41.
Marguiles, et al. Genome sequencing in microfabricated high-density picolitre reactors. Nature. Sep. 15, 2005;437(7057):376-80. Epub Jul. 31, 2005.
Metzker, ML. Sequencing technologies—the next generation. Nat Rev Genet. 2010.11(1):31-46 Epub Dec. 8, 2009. Review.
Miller, et al. A simple salting out procedure for extracting DNA from human nucleated cells. Nucleic Acids Research. 1998: 16(3): 9-10.
Office action dated Feb. 19, 2013 for U.S. Appl. No. 13/153,218.
Rawls. Optimistic About Antisense: Promising clinical results and chemical strategies for further improvements delight antisense drug researchers. C & E News. Jun. 2, 1997; p. 35.
Saiki, et al . Enzymatic amplification of beta-globin genomic sequences and restriction site analysis for diagnosis of sickle cell anemia. Science. Dec. 20, 1985;230(4732):1350-4.
Sprinzl, et al. Enzymatic incorporation of ATP and CTP analogues into the 3' end of tRNA. Eur J Biochem. Dec. 1977;81(3):579-89.
Venter, et al. Sequence of the Human Genome. Science. Feb. 16, 2001; 291(5507): 1304-1351.
Wu, et al. 3'-O-modified nucleotides as revers . . . [Proc Natl Acad Sci U S A. 2007] PubMed—NCBI. Proc Natl Acad Sci U S A. Oct. 16, 2007;104(42):16462-7. Epub Oct. 8, 2007.
Yang, et al. Nucleoside alpha-thiotriphosphates, polymerases and the exonuclease III analysis of oligonucleotides containing phosphorothioate linkages. Nucleic Acids Res. 2007;35(9):3118-27. Epub Apr. 22, 2007.
Notice of allowance dated Feb. 22, 2017 for U.S. Appl. No. 13/970,321.
Office action dated Jan. 22, 2017 for CN Application No. 201280027272X with English.
Office action dated Apr. 30, 2014 for CN Application No. 201180056235.7 (with English translation).
Office action dated May 12, 2016 for EP Application No. 12762821.2.
Office action dated Jun. 29, 2016 for CN Application No. 201280027272X with English.
Co-pending U.S. Appl. No. 15/631,414, filed Jun. 23, 2017.
Nickerson et al. Automated DNA diagnostics using an ELISA-based oligonucleotide ligation assay. PNAS USA 87(22):8923-8927 (1990).
Office action dated Jun. 14, 2017 for U.S. Appl. No. 14/970,435.
Office action dated Aug. 3, 2017 for EP Application No. 12762821.2.
Office action dated Sep. 27, 2016 for U.S. Appl. No. 13/970,321.

\* cited by examiner

Figure 1 is a schematic illustrating the process of sequencing a long nucleic acid.

Figure 2 is a schematic illustrating the process of sequencing a long nucleic acid where the resulting read has a gap.

Figure 3 is a schematic illustrating the process of creating an extended sequencing primer for sequencing Figure 4 is a schematic illustrating the process of building an extended sequencing primer by removing a sequencing product by peeling off the sequencing product or by digesting the sequencing product Figure 5 is a schematic illustrating the process of building an extended sequencing primer by removing a sequencing product by digesting sequencing product.

Figure 6 is a schematic illustrating the process of building an extended sequencing primer by partial digestion of a sequencing primer

FIG. 8

| Step | Length(bp) | Dark Base | | | | | | | | | | | |
|---|---|---|---|---|---|---|---|---|---|---|---|---|---|
| 1 | 7 | GCT | GGCTCTC | | | | | | | | | | |
| 2 | 14 | AGC | GGCTCTCAAGGGCA | | | | | | | | | | |
| 3 | 21 | TCG | GGCTCTCAAGGGCATCGGTCG | | | | | | | | | | |
| 4 | 25 | ACG | GGCTCTCAAGGGCATCGGTCGACGC | | | | | | | | | | |
| 5 | 35 | TCA | GGCTCTCAAGGGCATCGGTCGACGCTCTCCTTAT | | | | | | | | | | |
| 6 | 40 | GCA | GGCTCTCAAGGGCATCGGTCGACGCTCTCCTTATGCCGAC | | | | | | | | | | |
| 7 | 46 | TCG | GGCTCTCAAGGGCATCGGTCGACGCTCTCCTTATGCCGACTCCTGC | | | | | | | | | | |
| 8 | 55 | ATG | GGCTCTCAAGGGCATCGGTCGACGCTCTCCTTATGCCGACTCCTGCATTAGGAAG | | | | | | | | | | |
| 9 | 63 | CAG | GGCTCTCAAGGGCATCGGTCGACGCTCTCCTTATGCCGACTCCTGCATTAGGAAGCAGCCCAG | | | | | | | | | | |
| 10 | 76 | ATG | GGCTCTCAAGGGCATCGGTCGACGCTCTCCTTATGCCGACTCCTGCATTAGGAAGCAGCCCAGTAGTAGTTGAGG | | | | | | | | | | |
| 11 | 82 | GCT | GGCTCTCAAGGGCATCGGTCGACGCTCTCCTTATGCCGACTCCTGCATTAGGAAGCAGCCCAGTAGTAGTTGAGGCCGTTG | | | | | | | | | | |
| 12 | 102 | AGC | GGCTCTCAAGGGCATCGGTCGACGCTCTCCTTATGCCGACTCCTGCATTAGGAAGCAGCCCAGTAGTAGTTGAGGCCGTTGAGCACCGCCCCCGCAAGGAA | | | | | | | | | | |

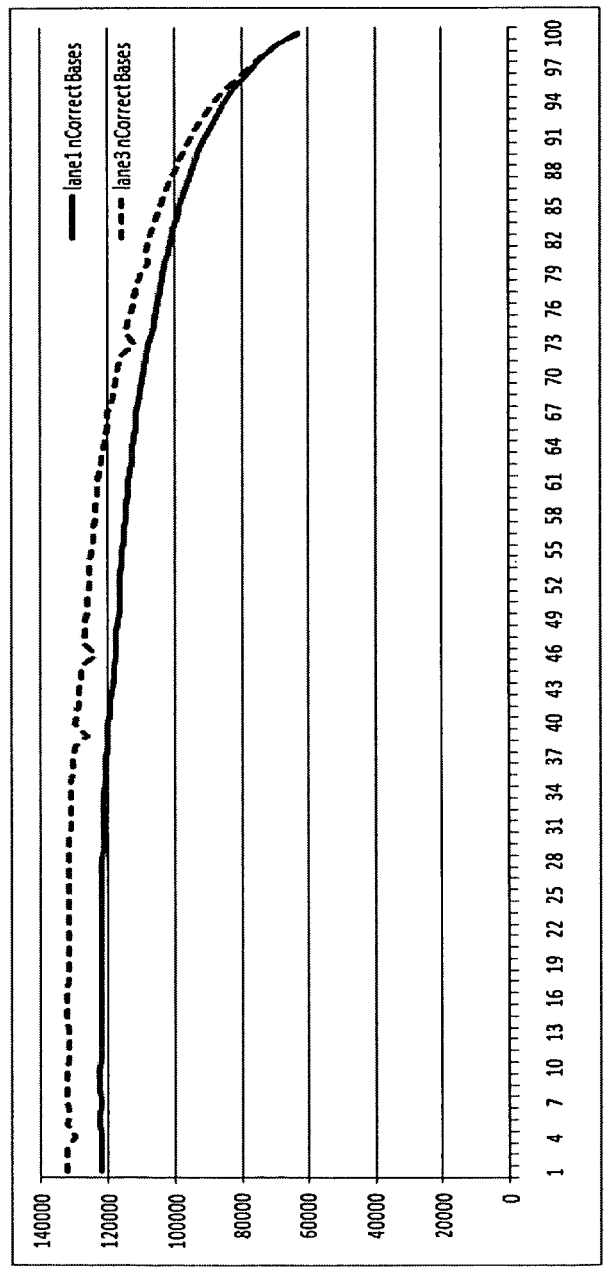

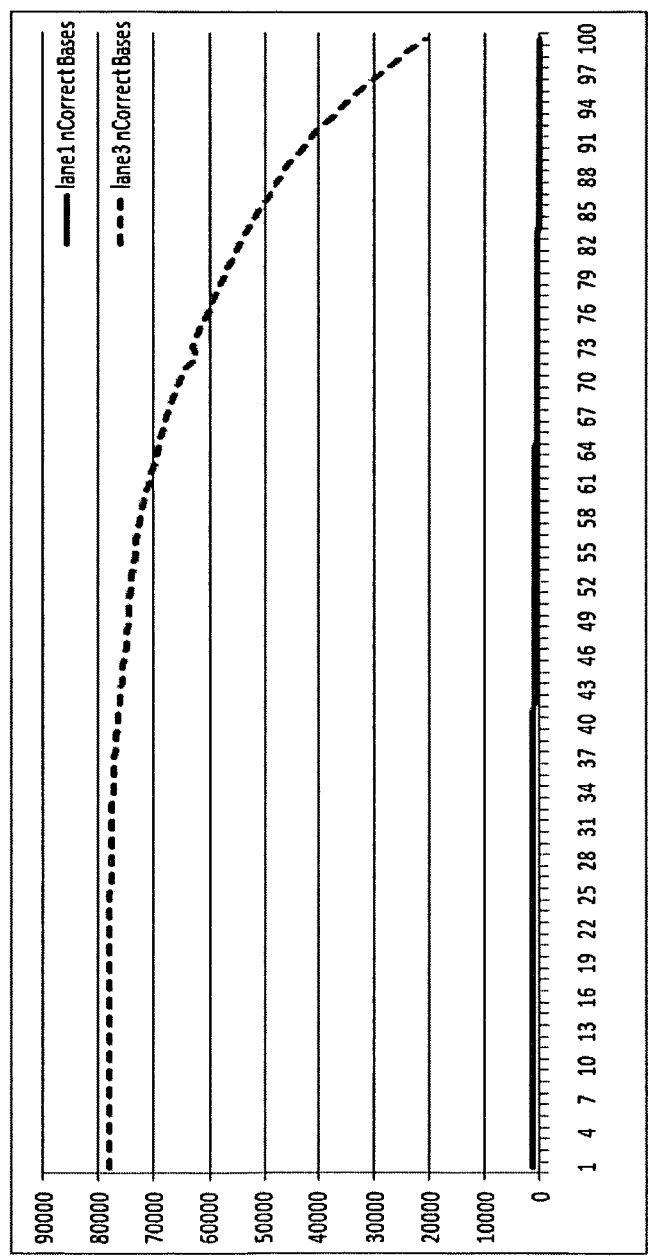

SEQUENCE LISTING

<160> NUMBER OF SEQ ID NOS: 11

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggctctcaag ggca                                                        14

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggctctcaag ggcatcggtc g                                                21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggctctcaag ggcatcggtc gacgc                                            25

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggctctcaag ggcatcggtc gacgctctcc cttat                                 35

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
ggctctcaag ggcatcggtc gacgctctcc cttatgcgac                    40
```

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
ggctctcaag ggcatcggtc gacgctctcc cttatgcgac tcctgc             46
```

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ggctctcaag ggcatcggtc gacgctctcc cttatgcgac tcctgcatta ggaag   55
```

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
ggctctcaag ggcatcggtc gacgctctcc cttatgcgac tcctgcatta ggaagcagcc   60
cag                                                                 63
```

<210> SEQ ID NO 9
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ggctctcaag ggcatcggtc gacgctctcc cttatgcgac tcctgcatta ggaagcagcc   60
cagtagtagg ttgagg                                                   76
```

<210> SEQ ID NO 10
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
ggctctcaag ggcatcggtc gacgctctcc cttatgcgac tcctgcatta ggaagcagcc   60
cagtagtagg ttgaggccgt tg                                            82
```

<210> SEQ ID NO 11
<211> LENGTH: 102
<212> TYPE: DNA
<213> ORGANISM: Artificial Sequence
<220> FEATURE:

-continued

```
<223> OTHER INFORMATION: Description of Artificial Sequence: Synthetic
      polynucleotide

<400> SEQUENCE: 11
ggctctcaag ggcatcggtc gacgctctcc cttatgcgac tcctgcatta ggaagcagcc      60
cagtagtagg ttgaggccgt tgagcaccgc cgccgcaagg aa                        102
```

METHODS AND SYSTEMS FOR SEQUENCING LONG NUCLEIC ACIDS

CROSS-REFERENCE

This application claims the benefit of U.S. Provisional Application Nos. 61/470,497, filed Apr. 1, 2011; 61/477,173, filed Apr. 20, 2011; and 61/489,662, filed May 24, 2011; and the U.S. Utility application Ser. No. 13/153,218, filed Jun. 3, 2011, now abandoned, each of which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jan. 28, 2014, is named 38558-705.831-Seqlist.txt and is 4 Kilobytes in size.

BACKGROUND

Nucleic acid sequencing is important for biological research, clinical diagnostics, personalized medicine and pharmaceutical development and many other fields. Cost effective, accurate and fast sequencing is needed for many applications, such as, but not limited to for microbial or pathogen detection and identification, and genetic identification for subjects. For example, applications can include, but not be limited to paternity testing and in forensic science (Reynolds et al., Anal. Chem., 63:2-15 (1991)), for organ transplant donor-recipient matching (Buyse et al., Tissue Antigens, 41:1-14 (1993) and Gyllensten et al., PCR Meth. Appl, 1:91-98 (1991)), for genetic disease diagnosis, prognosis, and prenatal counseling (Chamberlain et al., Nucleic Acids Res., 16:11141-11156 (1988) and L. C. Tsui, Human Mutat., 1:197-203 (1992)), and the study of drug metabolism and oncogenic mutations (Hollstein et al., Science, 253:49-53 (1991)). In addition, the cost-effectiveness of nucleic acid analysis, such as for infectious disease diagnosis, varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, and then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction, U.S. Pat. No. 4,683,202 and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported, U.S. Pat. No. 4,883,750, D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, Proc. Nat'l Acad. Sci. USA, 88:189-93 (1991) and F. Barany, PCR Methods and Applications, 1:5-16 (1991).

Another scheme for multiplex detection of nucleic acid sequence differences is disclosed in U.S. Pat. No. 5,470,705 where sequence-specific probes, having a detectable label and a distinctive ratio of charge/translational frictional drag, can be hybridized to a target and ligated together. This technique was used in Grossman, et al., Nucl. Acids Res. 22(21):4527-34 (1994) for the large scale multiplex analysis of the cystic fibrosis transmembrane regulator gene. Jou, et al., Human Mutation 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

Ligation of allele-specific probes generally has used solid-phase capture (U. Landegren et al., Science, 241:1077-1080 (1988); Nickerson et al., Proc. Natl. Acad. Sci. USA, 87:8923-8927 (1990)) or size-dependent separation (D. Y. Wu, et al., Genomics, 4:560-569 (1989) and F. Barany, Proc. Natl. Acad. Sci, 88:189-193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step-polymerase extension. The use of probes with distinctive ratios of charge/translational frictional drag for a more complex multiplex will either require longer electrophoresis times or the use of an alternate form of detection.

Methods for efficiently and accurately sequencing long nucleic acid fragments are needed. There is a great need for rapid, high-throughput, and low cost sequencing technology, such as for point-of-care applications and field detection of pathogens. The present invention permits sequencing of large amount of genome using simple chemistry and low cost equipments that lead to significant cost reduction and increase in speed, and other related advantages as well.

SUMMARY OF THE INVENTION

Provided herein are methods and systems for sequencing a target nucleic acid. Some embodiments of the invention are particularly suitable for sequencing a large number of target nucleic acids simultaneously.

In one aspect of the invention, methods, kits, computer software products are provided for sequencing long nucleic acids. Nucleic acids are often sequenced using stepwise methods such as polymerase extension based sequencing or ligation sequencing where one or more bases are read for each sequencing step. These stepwise based sequencing methods are often limited by its stepwise inefficiency, e.g., incomplete incorporation, incomplete ligation and other problems that create prephasing or dephasing. The stepwise inefficiency can accumulate over read length and limits read length.

In some embodiments, methods, kits and computer software products are provided to reset stepwise sequencing partially or completely.

In a first aspect, the method comprises: (a) sequencing one or more bases of a target nucleic acid by extending a first sequencing primer hybridized to the target nucleic acid to generate a first primer extension product, thereby obtaining a first sequence read; (b) releasing the first primer extension product from the target nucleic acid; (c) hybridizing a second sequencing primer to the target nucleic acid, optionally at the same or neighboring regions of the same target nucleic acid; (d) generating a second primer extension product (extended primer) by extending the second sequencing primer through limited or controlled extension; and (e) sequencing one or more bases of the target nucleic acid by further extending the second primer extension product to generate a third primer extension product, thereby obtaining a second sequence read. In one embodiment, the first sequencing primer and second sequencing primer are the same. In another embodiment, the first sequencing primer and second sequencing primer are different. The controlled or limited extension can be carried out or performed by pulse extension, such as, by allowing the extending reaction to last for a short period of time, such as less than a minute or from approximately half a minute to a minute, e.g. from 1-5, 5-10, 10-30, 30 to 60 seconds. In some embodiments, the extension is controlled by depriving 1, 2, or 3 of the four nucleotides. The pulse extension can be performed by adding nucleotide degrading enzymes such as alkaline phosphatase or apyrase. In some other embodiments, the pulse extension may be controlled using reversible terminator nucleotides. For example, each or some extension steps can be performed by including one or more reversible terminator nucleotides, such as dATP, dCTP, dGTP, dTTP*, where dTTP is a reversible terminator. In reversible terminator controlled extension, a step of removing the blocking group in the terminator may be performed before the next extension step.

In some embodiments, controlled extension can be performed by extension and wash cycles. Similar to the pulse extension, the controlled extension may be performed by limiting the availability of nucleotides or by adding reversible terminator nucleotide(s).

The limited extension can be carried out by using a nucleic acid polymerase and one or more sets of nucleotides. The one or more sets generally each comprise no more than three different nucleotides (bases). In some embodiments, the one or more sets comprise one to four nucleotides and at least one of the nucleotides is a reversible terminator nucleotide. The extending can be with more than one set of nucleotides, such as at least 1, 2, 3, or more sets. A set of nucleotides can comprise one, two or three different nucleotides.

In one embodiment, the method further comprises obtaining one or more additional sequence reads, such as by repeating the steps of releasing a primer extension product from the target nucleic acid; hybridizing an additional seed sequencing primer (or extension primer) (in some embodiments, the additional seed sequencing primer targeting the same or similar regions of the target nucleic acid) to the target nucleic acid; generating an additional primer extension product by extending the additional sequencing primer through controlled extension; and sequencing one or more bases of the target nucleic acid by further extending the additional primer extension product to generate an additional primer extension product, thereby obtaining an additional sequence read. The sequence of the target nucleic acid can be determined by assembling the first, second, and optional, one or more additional sequence reads. The sequencing of the target nucleic acid can be by extending the sequencing primer using a labeled reversible terminator, ligation, or any other methods known in the art for reading nucleotide sequences.

In another embodiment, a washing step or nucleotide degradation step can be performed prior to a subsequent addition of a set of nucleotides.

The target nucleic acid can be attached to a substrate. The substrate can be a flat surface or bead, such as a flow cell. In another embodiment, the substrate can comprise glass, silicon, metal, or plastics that have been surface treated to immobilize template strands or oligonucleotides. In another embodiment, the target nucleic acid can be attached to the substrate via a capture probe.

The methods and systems disclosed herein can further comprise analyzing the sequencing results, such as generated by a method disclosed herein, to provide a diagnosis, prognosis, or theranosis for a subject.

Furthermore, a method disclosed herein can be used to sequence a plurality of target nucleic acids.

In a second aspect, the invention refers to a method for sequencing a target nucleic acid, comprising:
 (a) obtaining a plurality of sequence reads from a nucleic acid template using a plurality of different sequencing primers, wherein at least one said primer is generated by a template dependent extension reaction; and
 (b) generating sequence information about the target nucleic acid by combining multiple sequence reads from step (a). In some embodiments, the sequence information comprises a nucleotide sequence of length greater than 500, 1000, 1500, 2000, or 3000 bases. In some embodiments, the assembled sequence reads generate sequence information with an average quality score of at least 26, 27, 28, 29, 30 or 31. In some embodiments, the assembled sequence reads generate sequence information with a quality score of at least 26, 27, 28, 29, 30 or 31 for any nucleotide position. In some embodiments, the sequence reads start at positions that are at least 5, 10, 15, 20, 25, 30, 35, 40, 50, 60, 70, 80, 90, 100, 150, 175, or 200 bases apart on the template nucleic acid. In some embodiments, sequence reads from the complement strand of the template nucleic acid are further assembled with the sequence reads.

(c) In a third aspect, the invention relates to kits for sequencing a target nucleic acid, comprising a primer that is hybridizable to the target nucleic acid, and one or more incomplete sets of nucleotides. In some embodiments, the multiple incomplete sets of nucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 40, 45, 50, or 60 incomplete sets of nucleotide bases. In some embodiments, the kit further comprises at least one DNA polymerase. In some embodiments, the DNA polymerase is a DNA-dependent DNA polymerase. In some embodiments, the DNA polymerase is an RNA-dependent DNA polymerase. In some embodiments, the DNA polymerase is Klenow exo(−). In some embodiments, the kit further comprises pyrophosphatase. In some embodiments, the kit further comprises apyrase. In some embodiments, the kit further comprises a nucleic acid denaturant. In some embodiments, the denaturant comprises, urea, formamide, or sodium hydroxide. In some embodiments, the kit further comprises a single strand binding protein. In some embodiments, an incomplete set of nucleotides comprises 1, 2, or 3 nucleotides. In some embodiments, the kit further comprises an exonuclease. In some embodiments, the exonuclease is a 5'-3' exonuclease. In some embodiments, the exonuclease is a 3'-5' exonuclease.

In a third aspect, the invention relates to a method for sequencing a target nucleic acid, the method comprising generating sequence information of length n from a single template using sequencing by synthesis; wherein the sequence information maintains a quality score of at least 26, 27, 28, 29, 30 or 31; and wherein n is greater than 100, 150, 200, 300, 400, 500, 700, 1000, 1500, 2000, or 3000.

In a fourth aspect, the invention relates to a system for sequencing a target nucleic acid, the system comprising;
(d) a sequencer adapted for multiple sequencing by synthesis reactions; and
(e) a primer that is hybridizable to the target nucleic acid; and
(f) one or more incomplete sets of nucleotides. In some embodiments, the multiple incomplete sets of nucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 40, 45, 50, or 60 incomplete sets of nucleotide bases. In some embodiments, the system further comprises at least one DNA polymerase. In some embodiments, the DNA polymerase is n DNA-dependent DNA polymerase. In some embodiments, the DNA polymerase is an RNA-dependent DNA polymerase. In some embodiments, the DNA polymerase is Klenow exo(−). In some embodiments, the system further comprises pyrophosphatase. In some embodiments, the system further comprises apyrase. In some embodiments, the system further comprising a nucleic acid denaturant. In some embodiments, the denaturant comprises, urea, formamide, or sodium hydroxide. In some embodiments, the system further comprises a single strand binding protein. In some embodiments, an incomplete set of nucleotides comprises 1, 2, or 3 nucleotides. In some embodiments, the system further comprises an exonuclease. In some embodiments, the exonuclease is a 5'-3' exonuclease. In some embodiments, the exonuclease is a 3'-5' exonuclease.

In a fifth aspect, the invention relates to a method for sequencing a target nucleic acid comprising:
(g) providing a first extension primer hybridized with said target nucleic acid;
(h) extending said first extension primer to a defined length; and
(i) sequencing the target nucleic acid from the extended first extension primer generating a first sequence read, thereby further extending the extended first extension primer with a sequencing product. In some embodiments, the method further comprises;
(d) removing said extended first extension primer and sequencing product;
(e) hybridizing a second extension primer with said target nucleic acid; and
(f) repeating steps (b) and (c) with the second extension primer replacing the first extension primer, sequencing a second region of said target nucleic acid generating a second sequence read. In some embodiments, the method further comprises;
(d) removing at least a part of said sequencing product;
(e) providing a second extension primer hybridized with said target nucleic acid;
(f) repeating steps b) and c) with the second extension primer replacing the first extension primer, sequencing a second region of said target nucleic acid generating a second sequence read, wherein said second region is different from said first region. In some embodiments, said removing comprises removing said sequencing product and said first extension primer completely from the target nucleic acid. In some embodiments, said removing comprises denaturing said sequencing product and said first extension primer from said target nucleic acid. In some embodiments, denaturing comprises contacting said sequencing product with NaOH, urea, or formamide. In some embodiments, said removing comprises enzymatic digestion of said sequencing product. In some embodiments, said removing comprises exonuclease digestion and wherein a base that is resistant to exonuclease digestion is incorporated to a position in the sequencing product during said sequencing. In some embodiments, said providing comprises:
(i) hybridizing a sequencing primer with said target nucleic acid;
(ii) sequencing a region of the target nucleic acid from the sequencing primer, thereby extending the sequencing primer with a sequencing product; and
(iii) removing a part of said sequencing product. In some embodiments, said providing comprises:
(i) hybridizing a sequencing primer with said target nucleic acid;
(ii) sequencing a region of the target nucleic acid from the sequencing primer, thereby extending the sequencing primer with a sequencing product;
(iii) removing said sequencing primer and its associated sequencing product; and
(iv) hybridizing said first extension primer with said target nucleic acid. In some embodiments, said first and second extension primers are the same. In some embodiments, said first and second extension primers are different. In some embodiments, said extending comprises controlled extension comprising:
(g) contacting said first extension primer with a set of nucleotides comprising no more than three different nucleotides and a polymerase.

In some embodiments, said extending comprises repeating step (g), wherein before the repeating, said nucleotides are removed. In some embodiments, said set of nucleotides are different between two subsequent steps. In some embodiments, said nucleotides are removed by washing. In some embodiments, said nucleotides are removed by a nucleotide degrading enzyme. In some embodiments, said set of nucleotides further comprises a reversible terminator nucleotide, wherein before the repeating, incorporated reversible terminator nucleotides are deblocked and made ready for further extension. In some embodiments, said extension is carried out by pulse extension. In some embodiments, said pulse extension is carried out by allowing an extending reaction to last 30 to 60 seconds. In some embodiments, the sequence of said target nucleic acid is determined by assembling said first, second, and optionally additional sequence reads. In some embodiments, said target nucleic acid is attached to a substrate. In some embodiments, said substrate is a flat surface or bead. In some embodiments, said substrate is a flow cell. In some embodiments, said substrate comprises glass. In some embodiments, said target nucleic acid is attached to said substrate via a capture probe. In some embodiments, the method further comprises analyzing results of said sequencing providing a diagnosis, prognosis, or theranosis for a subject. In some embodiments, the method further comprises sequencing a plurality of target nucleic acids. In some embodiments, said assembling results in sequence information comprising a nucleotide sequence of length greater than 500, 1000, 1500, 2000, or 3000 bases. In some embodiments, the assembling results in sequence information comprising an average quality score of at least 26, 27, 28, 29, 30 or 31. In some embodiments, the assembling results in sequence information comprising a quality score of at least 26, 27, 28, 29, 30 or 31 for any nucleotide position. In some embodiments, the first and second sequence reads start at positions that are at least 5, 10, 15, 20, 25, 30, 35, 40, 50, 60, 70, 80, 90, 100, 150, 175, or 200 bases apart on the template nucleic acid. In some embodiments, sequence reads from the complement strand of the template nucleic acid are further assembled with the first and second sequence reads. In some embodiments, the polymerase is Klenow exo(-). In some embodiments, the nucleotide degrading enzyme comprises pyrophosphatase or apyrase. In some embodiments, the enzymatic digestion of said sequencing product is performed by an enzyme comprising a 5'-3' exonuclease or 3'-5' exonuclease activity.

In a sixth aspect, the invention relates to a for sequencing a target nucleic acid comprising:
(a) performing a first sequencing of a first region of the target nucleic acid generating a first read;
(b) performing a second sequencing of a second region of the target nucleic acid generating a second read, wherein said first and second regions are different;
(c) combining said first and second regions to produce a combined read.

In some embodiments, said first and second sequencings are performed using as a template a polynucleotide from the same strand of the target nucleic acid. In some embodiments, at least one sequencing of said first and second sequencings comprises:
(i) extending an extension primer to a defined length; and
(ii) sequencing using the extended primer.

In some embodiments, said extending comprises controlled extension comprising:
(1) contacting said first extension primer with a set of nucleotides comprising no more than three different nucleotides and a polymerase.

In some embodiments, said extending comprises repeating of step 1, wherein before the repeating, said nucleotides are removed. In some embodiments, said set of nucleotides are different between two subsequent steps. In some embodiments, said nucleotides are removed by washing. In some embodiments, said nucleotides are removed by a nucleotide degrading enzyme. In some embodiments, said set of nucleotides further comprises a reversible terminator nucleotide wherein before the repeating, incorporated reversible terminator nucleotides are deblocked and made ready for further extension. In some embodiments, said combining is performed in silico by stitching said first and second regions into an assembled sequence for the target nucleic acid. In some embodiments, the assembled sequence comprises a gap of length n. In some embodiments, n is less than 2, 3, 4, 5, 6, 7, 8, 9, 10, 15, 20, 25, 30, 50, or 100 nucleotides. In some embodiments, said first and second sequencings are further performed using the same polynucleotide. In some embodiments, said extending is performed using native nucleotides. In some embodiments, said extension is carried out by pulse extension. In some embodiments, said pulse extension is carried out by allowing an extending reaction to last 30 to 60 seconds. In some embodiments, said target nucleic acid is attached to a substrate. In some embodiments, said substrate is a flat surface or bead. In some embodiments, said substrate is a flow cell. In some embodiments, said substrate comprises glass. In some embodiments, said target nucleic acid is attached to said substrate via a capture probe. In some embodiments, the method further comprises analyzing results of said sequencing providing a diagnosis, prognosis, or theranosis for a subject. In some embodiments, the method further comprises sequencing a plurality of target nucleic acids. In some embodiments, said combined read comprises sequence information comprising a nucleotide sequence of length greater than 500, 1000, 1500, 2000, or 3000 bases. In some embodiments, said combined read comprises sequence information comprising an average quality score of at least 26, 27, 28, 29, 30 or 31. In some embodiments, said combined read comprises sequence information comprising a quality score of at least 26, 27, 28, 29, 30 or 31 for any nucleotide position. In some embodiments, the first and second reads start at positions that are at least 5, 10, 15, 20, 25, 30, 35, 40, 50, 60, 70, 80, 90, 100, 150, 175, or 200 bases apart on the template nucleic acid. In some embodiments, a sequence read from a complement strand of the template nucleic acid are further combined producing the combined read. In some embodiments, the polymerase is Klenow exo(-). In some embodiments, the nucleotide degrading enzyme comprises pyrophosphatase or apyrase.

A set of nucleotides for controlled extension is a combination of any number of different types nucleotides including native, reversibly terminated, or other modified nucleotides as long as the combination allows controlled (or designed). In other words, a set of nucleotides is of any combination of any number of native, reversibly terminated, or otherwise manipulated nucleotides that do not result in runaway extension (unlimited extension). Sometimes, a controlled extension nucleotide set is described as containing no more than three different nucleotides. As used herein, "no more than three different nucleotides" refer to three different nucleotides, each having a different base (i.e., three of the A, C, G, T bases or three of the A, C, G, U bases. T and U bases can be considered equivalent in some embodiments). If a nucleotide set contains A, C, T, and U, it contains three different nucleotides because T and U are considered as equivalent in some embodiments. If the base of a nucleotide is modified, the modified nucleotide can be classified according to its pairing property. For example, if a dATP is modified in the base, but once incorporated, the base of the modified nucleotide still pair with a T base, the modified dATP still has the A base.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 depicts an example of a template and triple base extension reactions. FIG. 8 discloses SEQ ID NOS 1-11, respectively, in order of appearance.

DETAILED DESCRIPTION OF THE INVENTION

Figure 1:
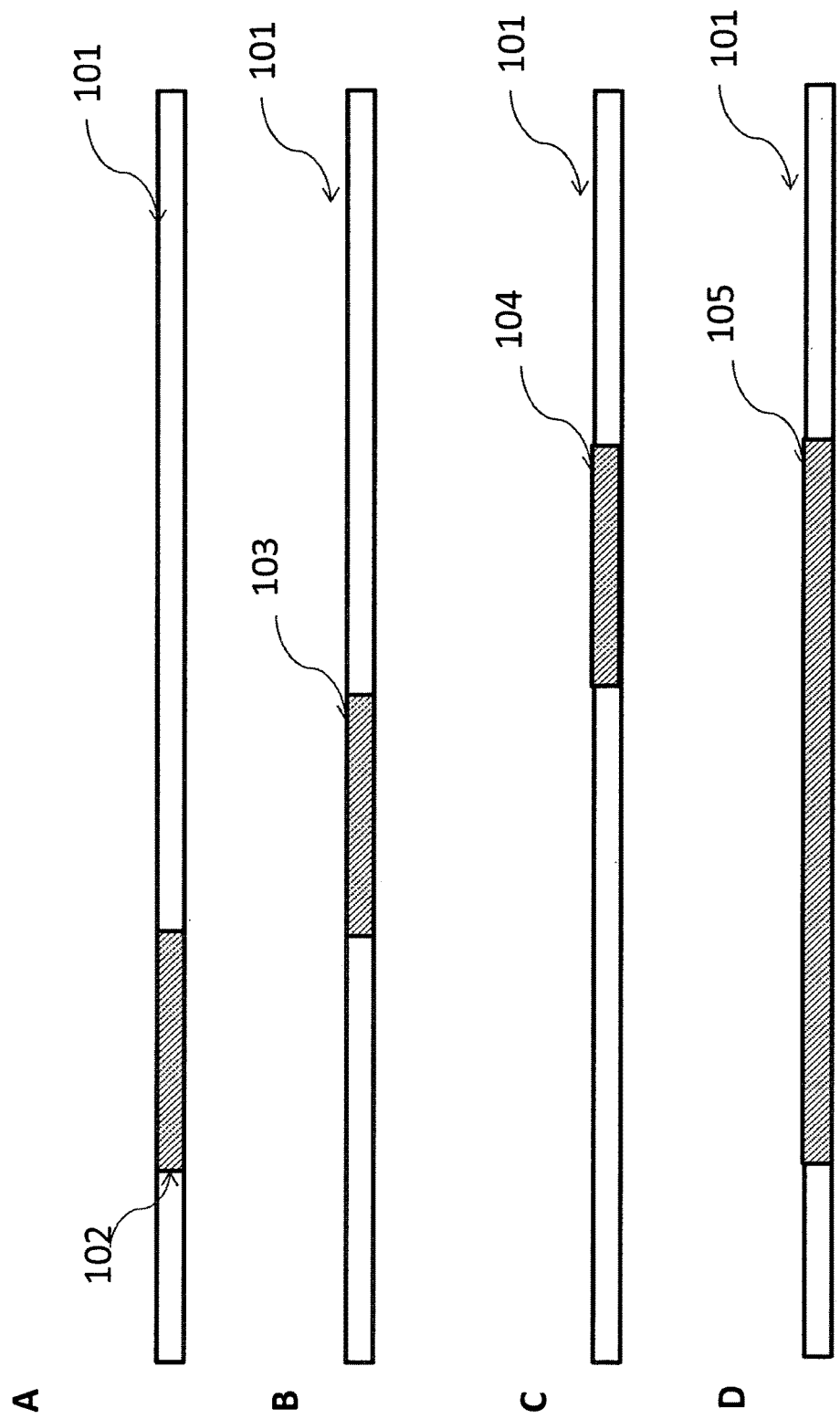
FIG. 1 is a schematic illustrating an exemplary process of sequencing a long nucleic acid.

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are now described. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry 4th Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

Provided herein are methods and systems for sequencing a target nucleic acid. Some embodiments of the invention are particularly suitable for sequencing a large number of target nucleic acids simultaneously.

In one aspect of the invention, methods, kits, computer software products are provided for sequencing long nucleic acids. Nucleic acids are often sequenced using stepwise methods such as polymerase extension based sequencing or ligation sequencing, where one or more bases are read for each sequencing step. These stepwise based sequencing methods are often limited by their stepwise inefficiency, e.g., incomplete incorporation, incomplete ligation and other problems that create prephasing or dephasing. The stepwise inefficiency can accumulate over read length and limits read length.

For example, reversible terminator nucleotide based sequencing (commercially available from Helicos, Inc., Illumina, Inc., Intelligent Biosystems, Inc./Azco Biotech, Inc. and described in vendor literature and their patent filings and at www.helicosbio.com, www.illumina.com, www.azcobiotech.com) are limited by the efficiency of incorporating reversible terminator nucleotides that are modified in the 3' hydroxyl group or modified otherwise to interrupt further extension by a polymerase. If the sequencing detection is based upon incorporation of modified nucleotides with added detectable label such as a fluorescent group, the incorporation efficiency could be further reduced. The problem can be partially alleviated by mixing unlabeled and labeled reversible terminator nucleotides. However, even with improved chemistry and efficiency, the stepwise inefficiency can significantly limit read length and read quality at the end of the read.

The stepwise efficiency problem can be illustrated with a case where each sequencing step has a constant stepwise efficiency of incorporation of about 99% and there are 1,000 template molecules in a cluster. After the first incorporation step, 10 sequencing primers are not extended and are capped or otherwise no longer involved in sequencing. In such a case, after 100 sequencing steps, only $(0.99)^{100}$=36.6% or 360 molecules remain in the cluster for additional sequencing. At step 200, only $(0.99)^{200}$=13.4% or 134 molecules remain in the cluster for additional sequencing. If the efficiency drops to 98%, at step 100, there is only 13.4% molecules left for additional sequencing reactions and at step 200, only 1.8% molecules can be potentially used for further sequencing.

For nucleotide limited addition sequencing methods such as pyrophosphate detection based sequencing (commercially available from Roche/454 and described in vendor literature and patent filings and at www.454.com) or pH detection based sequencing (commercially available from Ion Torrent, Inc./Life Technologies, Inc. and described in vendor literature and patent filings), the efficiency can be limited by incomplete incorporation, mis-incorporation, loss of bound polymerase (fall-off). Stepwise ligation based sequencing has a similar efficiency problem as stepwise efficiency is limited by, e.g., ligation reaction efficiency and removal of labels.

In one aspect of the invention, methods, reagents kits, instrument and computer software products are provided to sequence nucleic acids. In some embodiments, two or more segments of a nucleic acid target sequence are obtained sequentially from a template. The segments are then assembled to produce a contiguous sequence or a gapped sequence of the nucleic acid target sequence. FIG. 1 illustrates the process in some embodiments. A part (102) of the target nucleic acid (101) is sequenced (FIG. 1A). Another part (103) of the target nucleic acid (101) is also sequenced (FIG. 1B). The process can be repeated (FIG. 1C) many times. As shown in FIG. 1, the sequenced parts are overlapping so the sequences can be assembly based upon overlapping sequences and/or other information.

In some embodiments, a large number of target nucleic acids (e.g. at least 10, 100, 1,000, 10,000, 100,000, or 1,000,000) is sequenced simultaneously. These target nucleic acids can be DNA, RNA or modified nucleic acids. While they can be sequenced as single molecules, they can also be sequenced as clones or clusters. Each of the clones or clusters (e.g. on beads) are derived from a single nucleic acid molecule. Methods for sequencing a large number of target nucleic acids in single molecule or clonal molecular clusters or beads are well known in the art. For simplicity of illustration, some embodiments may be described using singular terms such as "a target nucleic acid" or "an extension primer," one of skill in the art would appreciate that many of the embodiments can be used to sequence many target nucleic acids simultaneously or sequentially and such sequencing may be performed on copies (more than 10, 100, 1,000, 100,000 copies) of the target nucleic acids.

A computer software product is generally used to assemble the sequences when the amount of data is quite large. The computer software product typically inputs the raw sequences for each of the target nucleic acids and assembles contiguous sequences upon finding overlapping regions and optionally validating the overlapping regions using additional information such as alignment with a reference sequence, information about the starting position of the sequencing run or relative positional difference among sequencing runs. The resulting contiguous sequence (105) can be further validated by, for example, alignment with a reference sequence for the target nucleic acid. The sequencing can be performed using, for example, stepwise sequencing methods discussed earlier. While the individual sequencing runs (such as 102, 103, and 104) have read length limitations based on the underlying sequencing readout technologies, the assembled contiguous sequence can be significantly longer at for example, greater than 1.5, 2, 3, 4, or 5× of the individual sequencing reads (102, 103, and 104). The individual sequencing runs can be carried out sequentially. In some embodiments, the order of the sequencing runs is not important. For example, the step in FIG. 1 C can be performed before the step in FIG. 1A. If the target nucleic acid is copied to several distinct locations, the sequencing runs using alternative sequencing primers may also be carried out in parallel.

Figure 2:
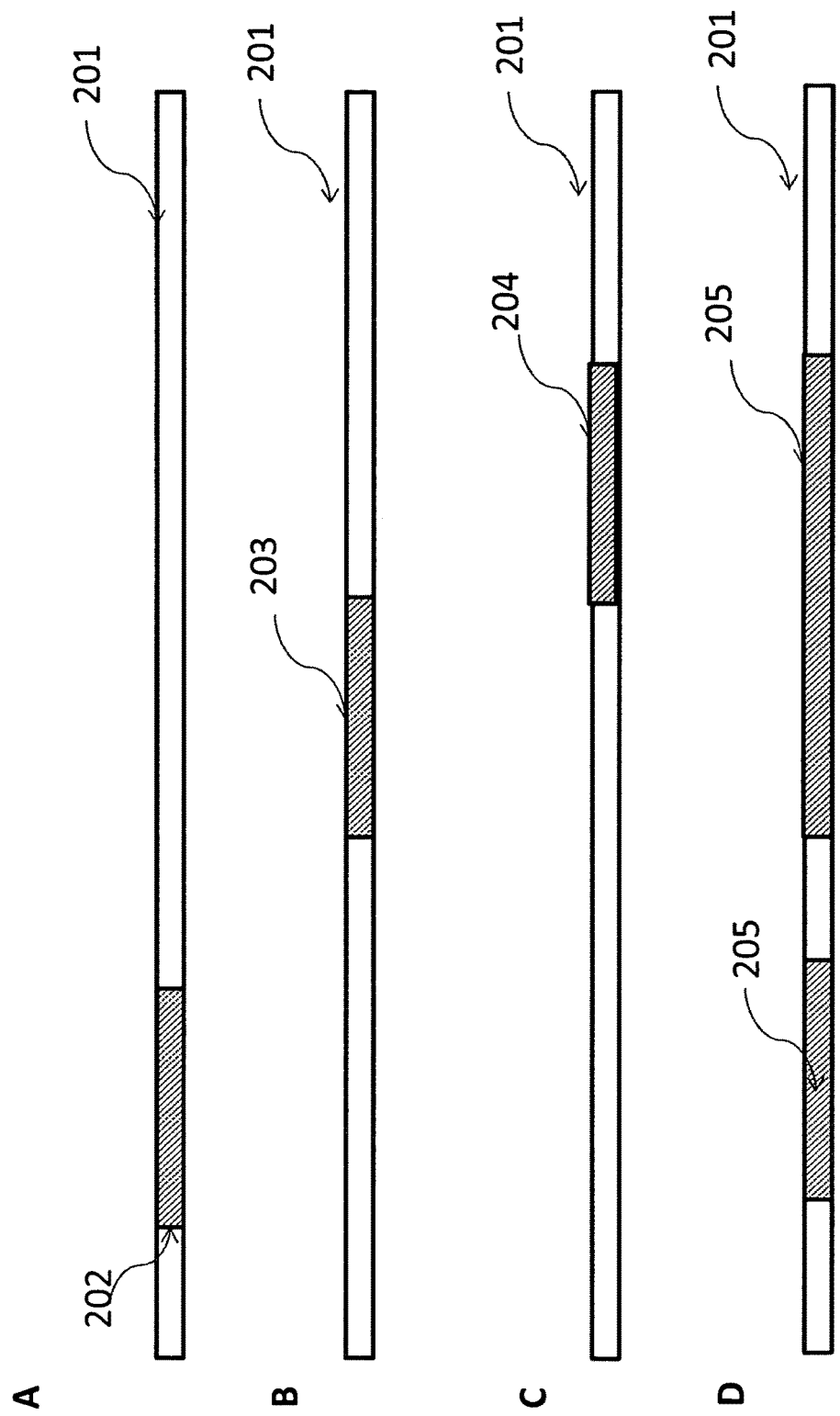
FIG. 2 is a schematic illustrating an exemplary process of sequencing a long nucleic acid where the resulting read has a gap.

The individual sequencing reads do not have to overlap. FIG. 2 illustrates the sequencing of a long nucleic acid by three independent sequencing runs. Sequencing reads 202 and 203 do not overlap and the resulting assembled sequence 205 has a gap. In some embodiments, the computer software product provided can output the sequence with the gap, but can also estimate the size of the gap based upon alignment to a reference sequence. The positional difference between the sequencing reads can be estimated, for example, based upon different sequencing primer starting positions. The positional difference can be used to estimate the gap size.

Because individual sequencing runs can be carried out independently, each sequencing run resets the sequencing start conditions and is not affected or less affected by cumulative inefficiency or errors. By segmenting the sequencing of a target nucleic acid, sequencing methods and chemistries that have inherent length limitations can be used to sequence a target nucleic acid obtaining longer sequence information than the original length limitations of these sequencing methods and chemistries. For example, for a reversible terminator sequencing chemistry with sequencing length limitation of 250 bases, a 1,000 base long target nucleic acid can be sequenced contiguously by carrying out the 250 base long reversible terminator sequencing 4 or more times. In various embodiments, the total read length from a single template can be up to 100, 200, 250, 500, 1000, 2000 bases or more.

In another aspect of the invention, methods and reagent kits are provided for building sequencing primers. The resulting sequencing primers can be of varying length. Different sequencing primers for the same target nucleic acid can be used to sequence different segments of the target nucleic acid.

In some embodiments, an extension primer hybridized to a target nucleic acid is provided. In one embodiment, the extension primer is extended by controlled extension. Controlled extensions can be performed using polymerase extension reactions, stepwise ligation reactions and other methods. For polymerase extension reaction, controlled extension can be performed by, for example, three nucleotide cycles or by reversible terminator reactions. Controlled extension is also described in great detail in a section below and throughout the specification.

Figure 3:
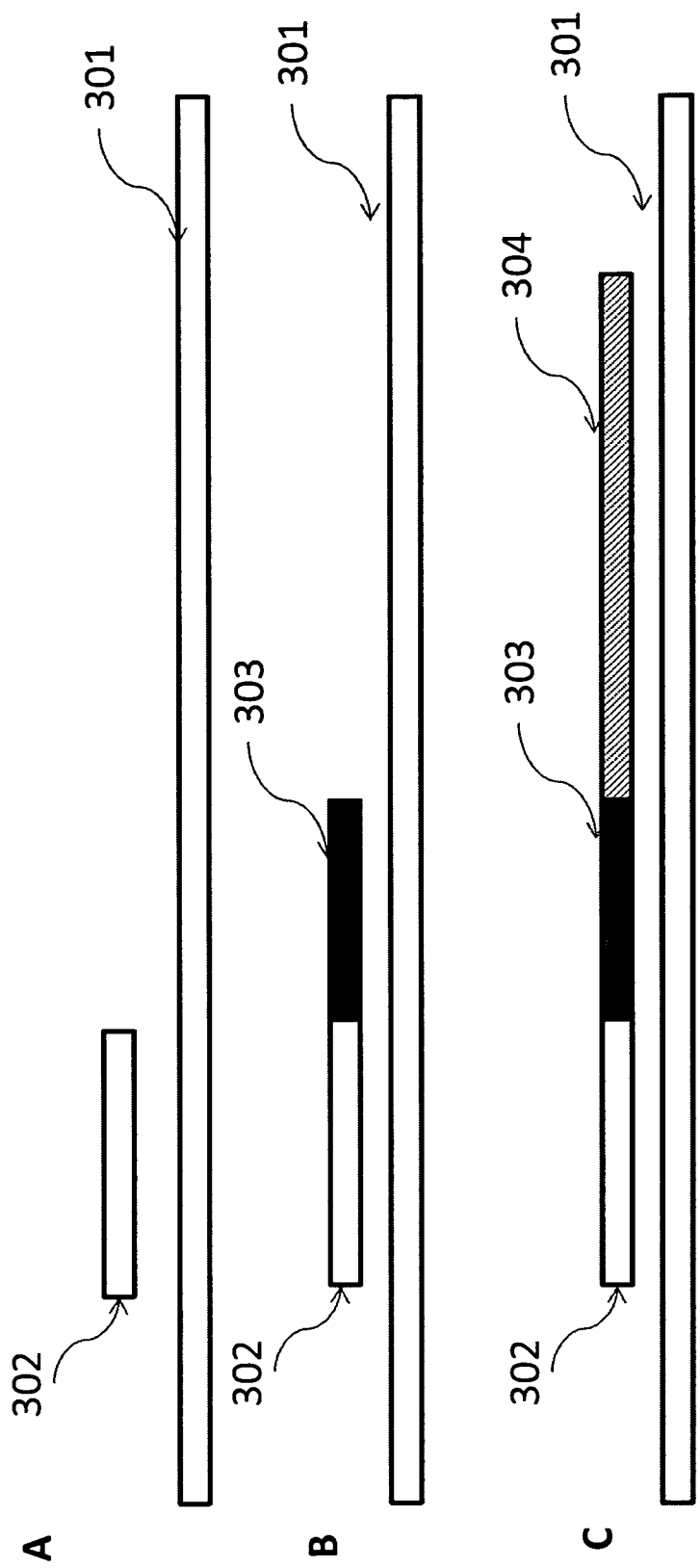
FIG. 3 is a schematic illustrating an exemplary process of creating an extended sequencing primer for sequencing

The extended extension primer can be used for sequencing. FIG. 3 illustrates some embodiments of this process. FIG. 3A shows that a target nucleic acid (301) is hybridized with an extension primer (302). In FIG. 1B, the extension primer (302) is then extended by a number of bases using one or more nucleic acid polymerization reactions or by one or more ligation reactions to produce an extended primer (302 and 303, where 303 is the extended portion). The extended primer (302, 303) is then used as a sequencing primer for sequencing (FIG. 3C, sequencing product is shown as 304).

In some embodiments, a target nucleic acid is hybridized with a sequencing product (such as the product resulting from FIG. 3C). The sequencing product can be the result of reversible terminator sequencing or nucleotide addition sequencing. Typically, in a clonal cluster of the target nucleic acids, sequencing products of different length may be hybridized with the target nucleic acid copies in the clonal cluster because of the inefficiencies of sequencing reactions which result in, for example, dephased or prephased products. One of skill in the art would appreciate that, while embodiments of the invention are often described using singular terms, typical sequencing reactions can be carried out using molecular clones, where each of the clones contains large number of copies of the same molecule with small variations because of errors in bridge amplifications, emulsion PCRs, rolling cycle amplifications and other amplification reactions. One of skill in the art would also appreciate that a large of number of target nucleic acids and thus a large number of molecular clonal clusters are sequenced simultaneously in a massively parallel fashion.

Figure 4:
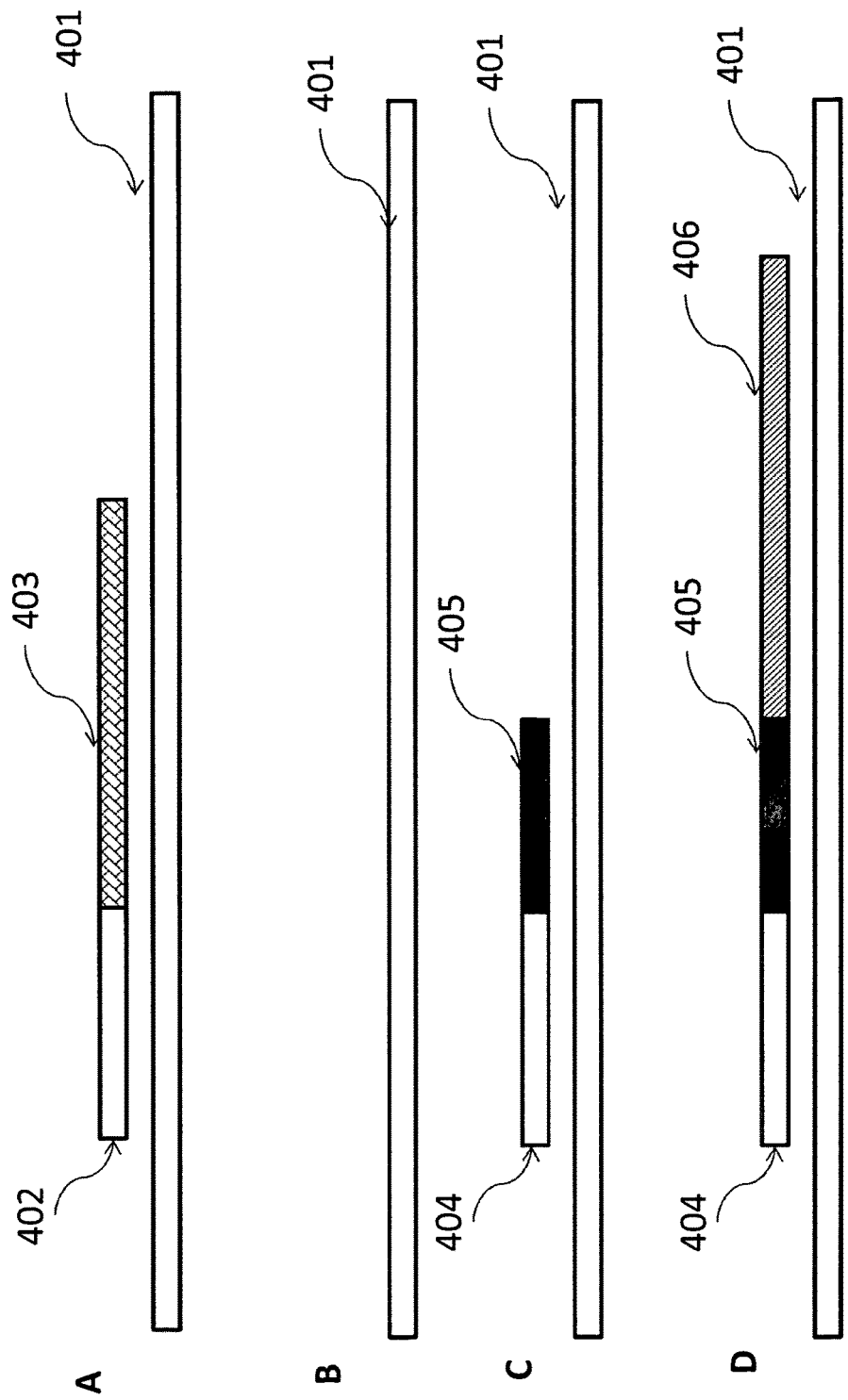
FIG. 4 is a schematic illustrating an exemplary process of building an extended sequencing primer by removing a sequencing product by peeling off the sequencing product or by digesting the sequencing product

Such a sequencing product (or in the case of sequencing clusters, products) can be removed before an extension primer is hybridized to the sequencing template. FIG. 4 illustrates some embodiments of the process. In FIG. 4A, a sequencing template (401) is hybridized with a sequencing primer (402) and the sequencing primer is used for sequencing which results in a sequencing product (403). The sequencing primer (402) and sequencing product (403) structure is removed by denaturation or by enzymatic digestion (FIG. 4B). Methods for removing a strand of nucleic acid from a double strand nucleic acid structure are well known in the art. For example, the sequencing structure can be denatured by contacting it with a NaOH solution (e.g., about 0.1 N NaOH) or another denaturation reagent. The sequencing product structure can also be removed by exonuclease digestion or other enzymatic treatment. If enzymatic digestion is used, the target nucleic acid strand can be protected using, for example, protecting bases in the 5' and/or 3' end. In many cases, the template is immobilized on a substrate so that only one end could be potentially susceptible to nuclease digestion. In some case, protecting the template is not necessary because certain exonucleases only digest in a particular orientation (5'-3' or 3'-5'). For example, exonuclease III predominately digests recessed 3' ends of double strand DNA. If the target nucleic acid is immobilized at its 3' end, it may not be necessary to protect the 5' end. After the sequencing product is removed, an extension primer can be hybridized and extended (FIG. 4C) as described above and detailed in following sections to produce an extended primer, which can serve as a primer for sequencing (FIG. 4D).

Figure 5:
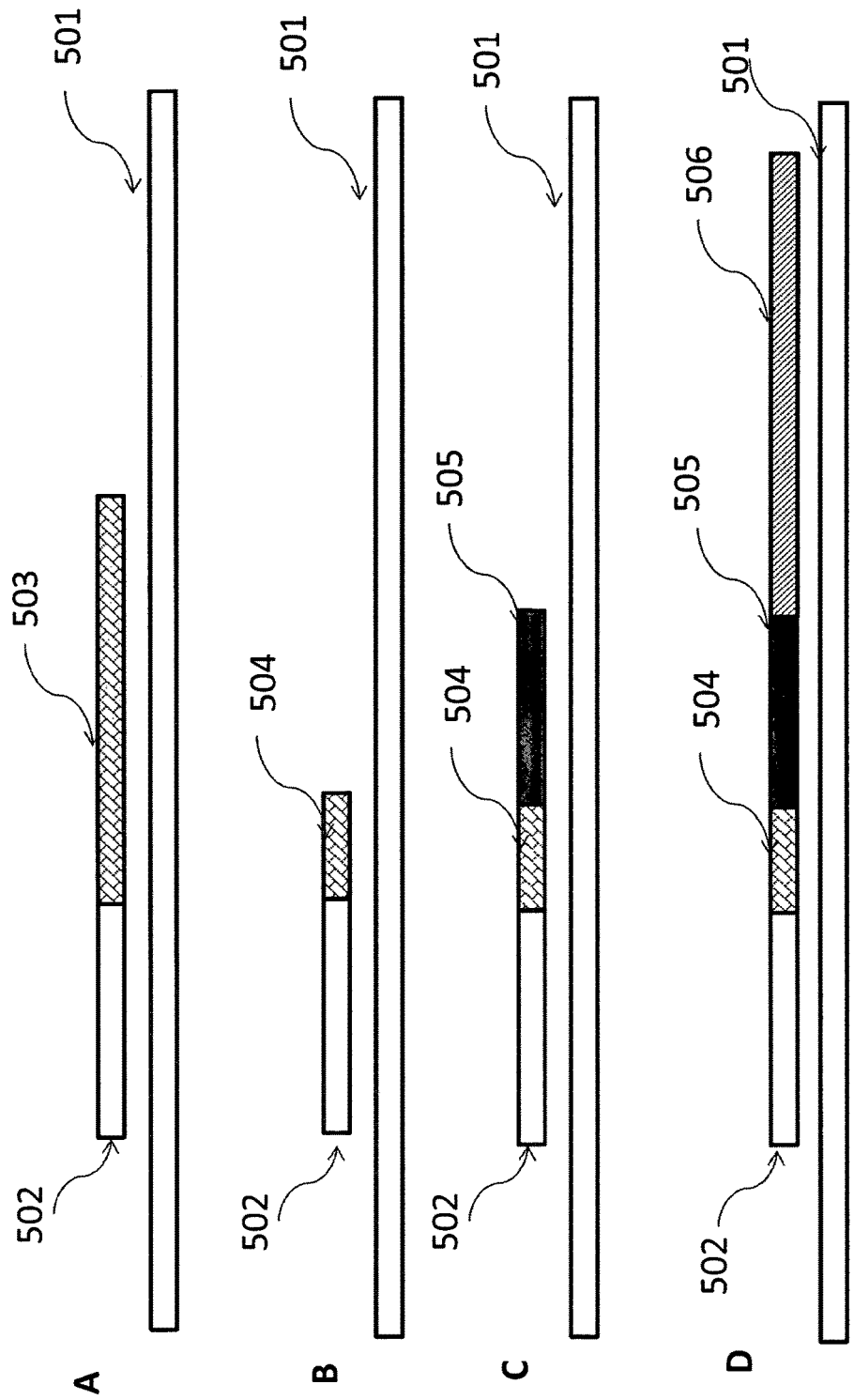
FIG. 5 is a schematic illustrating an exemplary process of building an extended sequencing primer by removing a sequencing product by digesting sequencing product.
Figure 6:
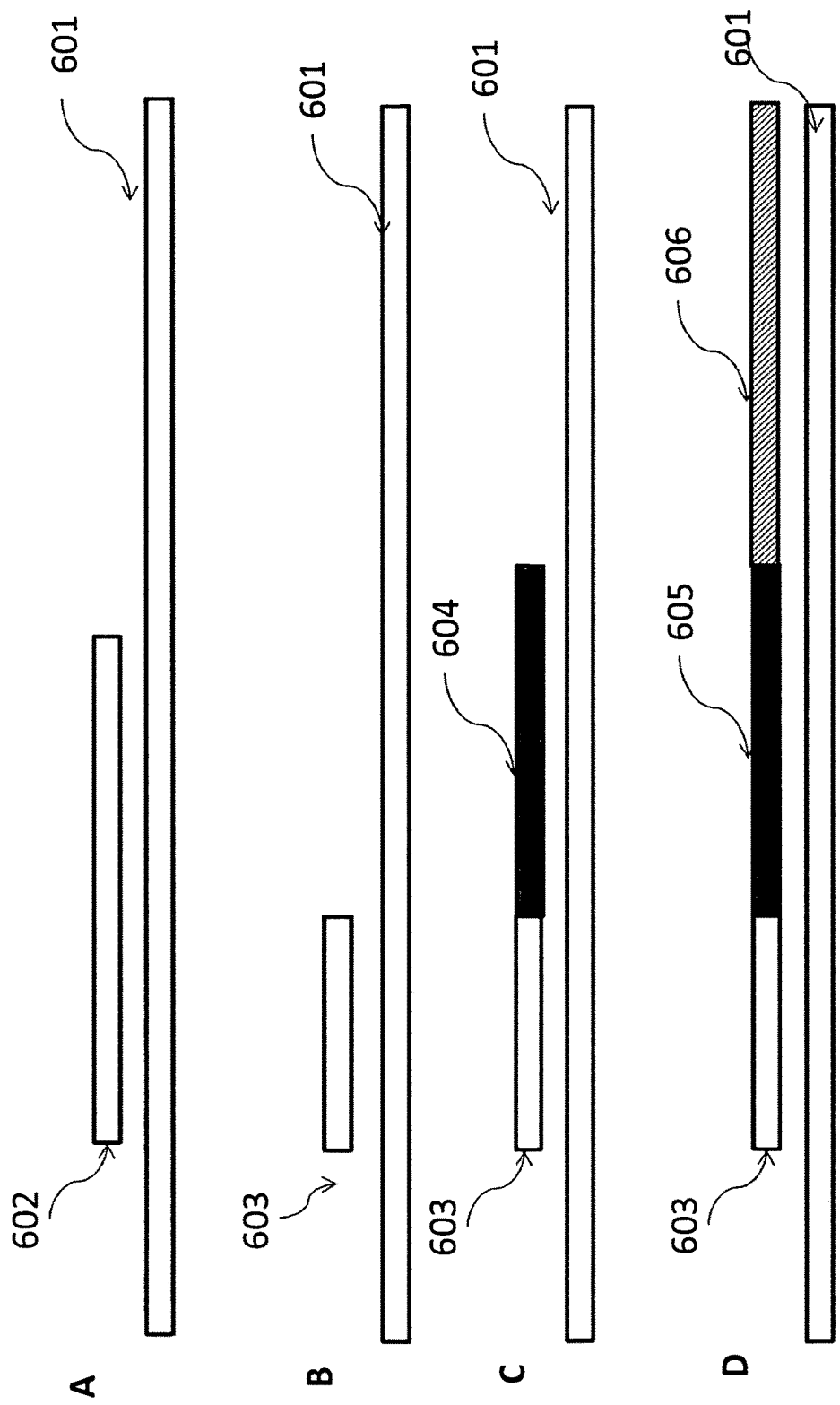
FIG. 6 is a schematic illustrating an exemplary process of building an extended sequencing primer by partial digestion of a sequencing primer.

In some other embodiments, a sequencing product structure does not need to be completely removed. It can be partially removed. As shown in FIGS. 5 and 6, the sequencing product part (503 or 603) may be completely (FIG. 6) or partially removed (FIG. 5, 505 is smaller than 503). The sequencing primer part (502 or 602) can be the product of earlier extension reactions such as these described in FIGS. 3,4, 5 and 6. Partial digestion of nucleic acids may be achieved using exonuclease digestion (such as Exonuclease III digestion). If a synthetic primer was used as 502, the last base can be a base that cannot be digested by an exonuclease. For example, if the orientation from 502 to 503 is 5' to 3', the last base of the 502 part can be connected using a thiol bond which is resistant to certain exonuclease digestion. It is well known that alpha-thiophosphate-containing phosphodiester bonds are resistant to hydrolysis by the 3'-to-5' exonucleolytic activity of phage T4 DNA polymerase and exonuclease III. A thiophosphate containing diester bond can also be produced by incorporating one or more thiotriphosphate nucleotides in the desired position(s). As reported by Yang et al., (2007), "Nucleoside Alpha-Thiotriphosphates, Polymerases and the Exonuclease III Analysis of Oligonucleotides Containing Phosphorothioate Linkages", Nucleic Acids Research, 2007, Vol. 35: 3118-3127, incorporated herein by reference, the pure S-diastereomer form of thiotriphosphate is recommended because the R-diastereomer form may be labile to Exonuclease III digestion.

FIG. 5B illustrates the partial digestion of sequencing product. For example, during sequencing, a nucleotide thiotriphosphate can be incorporated into one or more specific positions. In reversible terminator sequencing, the reversible terminator nucleotide can be a nucleotide thiotriphoshate. This position can be used to terminate an exonuclease digestion in the step illustrated in FIG. 5B. Partial removal of sequencing products can be useful where the early steps of sequencing do not introduce too many prephasing or dephasing or other inefficiencies. It can reduce the need for extension steps illustrated in FIG. 5C because the total size of 504 plus 505 is longer than 405 in FIG. 4 and extend the next sequencing (506) further than 406. However, by incorporating part of the sequencing product (505), if the 504 fragments in a cluster vary too much in length, the process may affect the subsequent sequencing quality.

Target or Target Nucleic Acid

In one aspect, the present invention provides a method for sequencing a target nucleic acid molecule or a collection of target nucleic acids. By "target nucleic acid molecule", "target molecule", "target polynucleotide", "target polynucleotide molecule" or grammatically equivalent thereof, as used herein it is meant a nucleic acid of interest. Target nucleic acid, for example, can be DNA or RNA or any synthetic structure that have similar properties of DNA or RNA. Sequencing, as used herein, refers to the determination of at least a single base, at least 2 consecutive bases, at least 10 consecutive bases or at least 25 consecutive bases in a target nucleic acid. Sequencing accuracy can be at least 65%, 75%, 85, 95%, 99%, 99.9% and 99.99% overall or per base. Sequencing can be performed directly on a target nucleic acid or on a nucleic acid derived from target nucleic acids. In some applications, a large number of target nucleic acids, such as at least 1,000, 10,000, 100,000 or 1,000,000 target nucleic acids are simultaneously sequenced.

In some embodiments, a target nucleic acid is genomic DNA derived from the genetic material in the chromosomes of a particular organism and/or in nonchromosomal genetic materials such as mitochondrial DNA. A genomic clone library is a collection of clones made from a set of randomly generated overlapping DNA fragments representing the entire genome of an organism. A genomic library is a collection of at least 2%, 5%, 10%, 30%, 50%, 70%, 80%, or 90% of the sequence or sequences in the genomic DNA of an organism.

Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification using methods known in the art, including without limitation extracting a fragment of genomic DNA from an organism (e.g. a cell or bacteria) to obtain target nucleic acids. In another example, target nucleic acids can also be isolated by amplification using methods known in the art, including without limitation polymerase chain reaction (PCR), whole genome amplification (WGA), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes. "Amplification" refers to any process by which the copy number of a target sequence is increased. Amplification can be performed by any means known in the art. Methods for primer-directed amplification of target polynucleotides are known in the art, and include without limitation, methods based on the polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, picotiter PCR and emulsion PCR. Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. In some embodiments, the amplification is performed inside a cell.

In any of the embodiments, amplification may occur on a support, such as a bead or a surface. In any of the embodiments herein, targets may be amplified from an extract of a single cell.

Target nucleic acids may also have an exogenous sequence, such as a universal primer sequence or barcode sequence introduced during, for example, library preparation via a ligation or amplification process. The term "sequencing template" used herein may refer the target nucleic acid itself or to a nucleotide sequence that is identical or substantially similar to the nucleotide sequence of a fragment of a target nucleic acid or the complement of a target nucleic acid. In one embodiment, the target nucleic acid molecule comprises ribonucleic acid (RNA).

In one embodiment, the target polynucleotide is genomic DNA or a portion of the genomic DNA. While one embodiment is for sequencing a whole genome, such as at more than 50% coverage, these embodiments are also suitable for sequencing a targeted region such as genomic regions relating to drug metabolism. In one example, the target polynucleotide is human genomic DNA.

Target nucleic acid, as used herein, can also refer to nucleic acid structures for sequencing. Such structures typically comprise adaptor sequences on one or both ends of target nucleic acid sequences. For example, a sequence derived from the genomic DNA of sample or derived from a RNA molecule of a sample, may be ligated with amplification and/or sequencing adaptor(s). Library construction methods are well known in the art. Nucleic acid sequencing libraries may be amplified in clonal fashion on substrates using bridge amplifications, emulsion PCR amplifications, rolling cycle amplifications or other amplification methods. Such processes may be performed manually or using automation equipment such as the cBot (Illumina, Inc.) or OneTouch™ (Ion Torrent).

"Nucleic acid" or "oligonucleotide" or "polynucleotide" or grammatical equivalents typically refer to at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (see e.g. Beaucage et al., Tetrahedron 49(10): 1925 (1993); Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048), phosphorodithioate (see e.g. Briu et al., J. Am. Chem. Soc. 111:2321 (1989)), O-methylphophoroamidite linkages (see e.g. Eckstein, Oligonucleotides and Analogues: A Practical Approach, Oxford University Press), and peptide nucleic acid (also referred to herein as "PNA") backbones and linkages (see e.g. Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996)).

Other analog nucleic acids include those with bicyclic structures including locked nucleic acids, also referred to herein as "LNA", (see e.g. Koshkin et al., J. Am. Chem. Soc. 120.13252 3 (1998)); positive backbones (Denpcy et al., Proc. Natl. Acad. Sci. USA 92:6097 (1995)); non-ionic backbones (see e.g. U.S. Pat. Nos. 5,386,023, 5,637,684, 5,602,240, 5,216,141 and 4,469,863; Kiedrowshi et al., Angew. Chem. Intl. Ed. English 30:423 (1991)); Letsinger et al., J. Am. Chem. Soc. 110:4470 (1988); Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook.

Nucleic acids containing one or more carbocyclic sugars are also included within the definition of nucleic acids (see e.g. Jenkins et al., Chem. Soc. Rev. (1995) pp 169 176). Several nucleic acid analogs are described in Rawls, C & E News Jun. 2, 1997 page 35.

The target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine, hypoxathanine, isocytosine, isoguanine, etc.

In one embodiment, the methods of the present invention comprise capture of target polynucleotide. The target polynucleotide may be from a known region of the genome. In one embodiment, oligonucleotide probes can be immobilized on beads and these oligonucleotide beads which are inexpensive and reusable can be used to capture the target genomic polynucleotide. In another embodiment, microarrays are used to capture target polynucleotide.

In one embodiment, the target polynucleotide may be fragmented to a suitable length or plurality of suitable lengths, such as approximately between 100-200, 200-300, 300-500, 500-1000, 1000-2000 or more bases in length.

In one embodiment, the target polynucleotide is prepared by whole genome amplification (WGA) (see for example, Hawkins et al.: Whole genome amplification—applications and advances. Curr Opin. Biotechnol. 2002 February; 13(1): 65-7)). In another embodiment, the target polynucleotide is prepared by whole genome sampling assay (WGSA). Generally, the WGSA reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified. The fragments that are amplified by WGSA may be predicted by in silico digestion and restriction enzyme combinations may be selected so that the resulting WGSA amplified fragments may represent the genomic regions of specific interests. The resulting library, often having desired adaptor sequences (including optional barcode sequences and sequencing primer hybridization site(s)) may be used for sequencing and for hybridizing with a genotyping array. In such embodiments, the library can be used for sequencing and the detected SNPs or indels can be validated by hybridizing the same library with an array. WGSA is disclosed in Kennedy et al. (2003), *Nat Biotechnol*, Vol., pp. 1233-1237, and U.S. patent application Ser. Nos. 10/316,517, 10/442, 021, 10/463,991, 10/316,629 and U.S. Pat. Nos. 6,361,947, 6,548,810, 7,267,966, 7,297,778, and 7,300,788, all of which are herein incorporated by reference.

In one embodiment, the target polynucleotide or a collection of target polynucleotides is prepared by PCR, such as long-range PCR. Long range PCR allows the amplification of PCR products, which are much larger than those achieved with conventional Taq polymerases. Generally, up to 27 kb fragments from good quality genomic DNA can be prepared, although 10-20 kb fragments are routinely achievable, given the appropriate conditions. In some embodiments, a fragment greater than 27 kb is obtained. The method typically relies on a mixture of thermostable DNA polymerases, usually Taq DNA polymerase for high processivity (i.e. 5'-3' polymerase activity) and another DNA polymerase with 3'-5' proofreading abilities (usually Pwo). This combination of features allows longer primer extension than can be achieved with Taq alone.

In one embodiment, the target polynucleotide is prepared by locus-specific multiplex PCR. Multiplex locus specific amplification can be used to amplify a plurality of pre-selected target sequences from a complex background of nucleic acids. The targets are selected for amplification using splint oligonucleotides that are used to modify the ends of the fragments. The fragments have known end sequences and the splints are designed to be complementary to the ends. The splint can bring the ends of the fragment together and the ends are joined to form a circle. The splint can also be used to add a common priming site to the ends of the target fragments. Specific loci are amplified and can be subsequently analyzed.

In yet another embodiment, target polynucleotides are produced using multiplex PCR and each of the PCR fragments is labeled with a tag sequence. Such tag sequence can be added as a part of one of the primers used for the PCR. Therefore, each resulting PCR fragment can be uniquely identified. Such applications can be useful for the identification of species, such as microbial species.

Other suitable amplification methods include but are not limited to the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603 each of which is incorporated herein by reference). Other amplification methods that may be used are described in, U.S. Pat. Nos. 5,242,794, 5,494, 810, 4,988,617 and in U.S. Ser. No. 09/854,317, each of which is incorporated herein by reference. Additional methods of sample preparation and techniques for reducing the complexity of a nucleic sample are described in Dong et al., Genome Research 11, 1418 (2001), in U.S. Pat. Nos. 6,361,947, 6,391,592, 6,632,611, 6,872,529, 6,958,225 and U.S. Ser. No. 09/916,135.

Naturally-existing targets can be assayed directly in cell lysates, in nucleic acid extracts, or after partial purification of fractions of nucleic acids so that they are enriched in targets of interest. In one example, the target polynucleotide is human genomic DNA. The polynucleotide target to be detected can be unmodified or modified. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, ether by chemical or enzymatic reaction such as ligation or polymerase-assisted extension. Alternatively, the internal labels and anchor ligands can be incorporated into an amplified target or its complement directly during enzymatic polymerization reactions using small amounts of modified NTPs as substrates.

The target polynucleotide can be isolated from a subject. The subject is not limited to a human being but may also be other organisms including but not limited to mammals, plants, bacteria, virus or fungi. In one example, the target polynucleotide is genomic DNA extracted from a human.

The input nucleic acid can be DNA, or complex DNA, for example genomic DNA. The input DNA may also be cDNA. The cDNA can be generated from RNA, e.g., mRNA. The input DNA can be of a specific species, for example, human, rat, mouse, other animals, plants, bacteria, algae, viruses, and the like. The input nucleic acid also can be from a mixture of genomes of different species such as host-pathogen, bacterial populations and the like. The input DNA can be cDNA made from a mixture of genomes of different species. Alternatively, the input nucleic acid can be from a synthetic source. The input DNA can be mitochondrial DNA. The input DNA can be cell-free DNA. The cell-free DNA can be obtained from, e.g., a serum or plasma sample. The input DNA can comprise one or more chromosomes. For example, if the input DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC). The input DNA can be from more than one individual or organism. The input DNA can be double stranded or single stranded. The input DNA can be part of chromatin. The input DNA can be associated with histones. The methods described herein can be applied to high molecular weight DNA, such as is isolated from tissues or cell culture, for example, as well as highly degraded DNA, such as cell-free DNA from blood and urine and/or DNA extracted from formalin-fixed, paraffin-embedded tissues, for example.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the invention, such as to remove excess or unwanted reagents, reactants, or products.

Controlled Primer Extension

A controlled extension is an increase in the length of an extension primer by a defined length or defined distance. As used herein, defined length refers to a length of extension that is dependent upon the extension conditions and may be dependent upon the template sequence. For an extension reaction, a defined length of the extension may not be known, but can be determined. For example, a single step of three nucleotide extension can extend the primer to a position where a missing nucleotide is needed for correct further extension. Such a position is dependent upon the nucleotide combination and the template sequence and is thus defined. But it may not be known if the template sequence is unknown and the extension product has not been measured. Once the template or target nucleic acid sequence is determined, the extension length can be estimated.

In some other embodiments, however, the defined length may be independent of the template sequence. For example, if the controlled extension is carried out by stepwise ligation reactions, the defined extension length could be independent of the template sequence. There are many ways to carry out stepwise ligation to grow a primer. In one example, a random hexamer (a collection of hexamers with random sequences) is ligated to the 5' end of the extension primer. The random hexamer does not have 5' phosphate so it cannot be ligated to already extended primer (added hexamer does not provide 5' phosphate). The 5' phosphate can be added with a kinase reaction and the extended primer is then read for another extension. In this example, each extension step adds 6 bases. Similar stepwise ligation can be performed in the 3' end of the extension primer.

For a clonal cluster of molecules for sequencing, the controlled extensions are at least 55%, 65%, 70%, 75%, 80%, 85%, 95%, 98%, 99%, 99.9%, 99.99% synchronized, because at least majority of the molecules in a cluster are extended at the same length for each steps.

In some embodiments, a controlled primer extension is performed using polymerization. In such embodiments, the extension primer is extended from its 3' end in the 5'-3' orientation. In some embodiments, long nucleic acids are sequenced by incorporating sequence reads that are obtained using one or more the controlled primer extension reactions. In some embodiments, controlled primer extension comprises the use of native nucleotides or modified nucleotides.

In one embodiment, a series of sequential reactions is performed such that each reaction of the series extends an extension primer, such as a deoxyribonucleic acid (DNA) primer or a sequencing primer, to a different length to create incremental sequences complementary to a sequencing template (the target nucleic acid or target polynucleotide molecule). For each of the extension reactions (often with incremental number of steps), the extension primer may be the same or similar to other(s) in the series. As used herein, two similar primers may target the same region of the target nucleic acid or target neighboring regions, typically within 10, 20, 50, 100 bases. Two similar primers may target the same region but be different in length. In many sequencing reactions, the desired region of the target nucleotides may be surrounded by or adjacent to adaptor and/or key(s) sequences. In one example, a biologically derived sequence may be ligated with an adaptor sequence (such as in sequencing libraries for Illumina HiSeq's reversible terminator sequencing or for Ion Torrent's pH detection sequencing).

A sequencing primer is often designed to hybridize with the whole or a part of the adaptor sequence and can be designed to hybridize to the last 3' base of an adaptor sequence so that the first base read is the biological sample derived sequence (Illumina HiSeq library). However, in some cases, the sequencing primer may be designed to hybridize to a region that is 5' to the biological sample derived sequence because the first part of the sequence to be read can be a barcode or index run or a key sequence (e.g., in Ion Torrent PGM Sequencing). These sequencing primers can also be used as extension primers.

In some embodiments, the extension primer sequences are designed to hybridize to the same or different parts of the adaptor sequences, typically 5' to the biologically derived sequences. The extension primers can be the same or similar.

An extension primer and the extended extension primer can also be used as a sequencing primer. The extension of the extension primer or sequencing primer can be with one or more nucleotides and a polymerase, such as native or native performance nucleotide(s) and native or native performance polymerase or a modified polymerase. Where RNA extension can be performed similarly, using an RNA polymerase, various embodiments are illustrated using DNA extensions as examples.

These extended extension primers can be generated or produced by extending the extension primer through controlled extension, such as by pulse extension. In some embodiments, a series of extended sequencing primers of incremental length are generated. In another embodiment, sequencing primers of incremental length can be generated or produced by extending the extension primer through extension, such as with an incomplete set of nucleotides, i.e., with a set of nucleotides comprising no more than three different nucleotides. Each incomplete set of nucleotides can extend the extension primer until the extension reaches a position where the target nucleic acid (or template) has the complementary nucleotide base. For example, in an incomplete set of nucleotides comprising C, G, and T, the sequencing primer can be extended until it reaches a T base in the template target nucleic acid.

Multiple steps of extension can be performed using different incomplete nucleotide sets. The extension reactions can be performed with at least two different sets of nucleotides. For example, multiple steps of extension can be performed using a first nucleotide set consisting of dATP, dCTP, dGTP and a second nucleotide set consisting of dATP, dCTP, dTTP. Because certain DNA polymerases can incorporate nucleotide diphosphates, if such a DNA polymerase is used for extension, the nucleotides can be diphosphates instead of triphosphates.

Between the extension steps, unincorporated nucleotides need to be removed to avoid run-offs. In some embodiments, a washing step is used between two extension steps. Because the target nucleic acids or the extension primers are often immobilized on a substrate such as on a glass slide or on beads, washing can be performed relatively easily. The washing solution may optionally include nucleotide degrading enzymes such as apyrase and/or alkaline phosphatase.

Controlled extension can be performed using pulse extension with no washing steps between extension steps when extension is performed with serial addition of various sets of nucleotides, wherein each set comprises one, two or three different nucleotides. In a pulse mode, sets of nucleotides are typically added serially at specified time intervals (such as for 1-10, 10-20, 20-30, 30-60 seconds). The nucleotides are typically degraded before the next addition of nucleotides by nucleotide degrading enzymes such as apyrase and/or alkaline phosphatase in the reaction solution.

Extension with washing and pulse extension steps can be combined. For example, extension can be performed in a pulse mode After certain number of pulse extension steps (such as 20-40, 41-60, 61-100 steps), the reaction mixture can be washed to remove residual nucleotides or by products. A new series of pulse extension steps can then be performed.

In some embodiments, controlled extension is performed using unmodified nucleotides. Unmodified nucleotides are typically more efficiently incorporated than labeled nucleotides. However, labeled nucleotides can be used as long as their incorporation efficiency is high. Incorporation efficiency can be affected by the polymerase used. Therefore, the selection of nucleotides can be dependent upon the corresponding polymerase used to incorporate the nucleotides. Modified nucleotides with a bulky group such as a fluorescent label can significantly reduce the incorporation efficiency and may not be good nucleotides for some embodiments.

In one embodiment, the controlled extension can be performed using a polymerase in a buffer that is suitable for the polymerase to catalyze polymerase reaction. In addition to the polymerase, nucleotide(s) are also added to the extension reaction. In one embodiment, a reaction contains a polymerase and a set of nucleotides, wherein the set of nucleotides comprises no more than three different nucleotides. For example, the set of nucleotides consists of one to three of the four types of nucleotides (e.g. for DNA polymerase, one, two or three of the four nucleotides dATP, dCTP, dTTP, dGTP). In one embodiment, a reaction containing three of the different nucleotides stops at the template base that is complementary to the missing nucleotide. For example, for a reaction that has dATP, dCTP, dGTP, the extension stops at a base "A" on the template because "A" is complementary to the missing nucleotide dTTP, thereby limiting extension of a primer hybridized to the template. Alternatively, nucleotide polymers, such as dimers, trimers, or longer nucleotide polymers can be used in each set. For example, a set may contain GA, GG, GC, GT, AA, AG, AC, AT, CA, CC, CG, and CT.

Base extension can be performed many times with various nucleotide sets, or with numerous cycles of nucleotide sets. For random chosen genomic sequences, the average extension length per single "three nucleotide" extension step is about 4 bases. To extend an average length of approximately 96 bases, a total of 24 extension steps are needed on average. In comparison, "single nucleotide" extension as used in Ion Torrent's PGM or pyrophosphate sequencing requires a total of 154 extension steps to achieve an approximate average extension length of 96 bases. Forty eight three base extension steps can achieve an average extension length of approximately 192 bases. Three nucleotide extensions are more than 6 times faster than single nucleotide extensions.

Optimizing conditions for controlled extension is important for many embodiments where it is desirable to minimize dephasing or prephasing. DNA polymerases, such as Bst DNA polymerase and Klenow DNA polymerase, both of which are suitable for controlled extension, may incorporate wrong bases particularly if the correct nucleotide is absent. Mis-incorporation tends to happen slower than correct incorporation for some enzymes. Therefore, it may be desirable to complete the extension quickly, for example, within 30 sec, 1 min., 2 min. or 5 min. of incorporation time. On the other hand, too short an extension time may cause incomplete incorporation because of the lack of sufficient incorporation time. Many DNA polymerases, however, have very fast incorporation time.

Nucleotide concentration is another important consideration for controlled extensions. Higher concentrations of nucleotides tend to cause mis-incorporation, while lower concentrations tend to cause incomplete incorporation. In some embodiments, the nucleotide concentration is between 1-100 µM, 2-60 µM, 3-50 µM, 3-25 µM, 3-10 µM, 5-8 µM. One of skill in the art would appreciate that the optimal nucleic acid concentrations vary. The optimal nucleotide concentration may be obtained by performing extensions using different nucleotide concentrations and measuring mis-incorporation and/or incomplete extension products versus correct extension products. Various extension products can be detected by gel electrophoresis, HPLC analyses or sequencing. The optimal nucleotide concentration may be dependent upon other conditions for controlled extension.

Many DNA polymerases are suitable for controlled extensions in at least some embodiments. Suitable DNA polymerases include, Klenow fragment, Bst, and other DNA polymerases known in the art. Bst DNA polymerase is particularly suitable for controlled extensions when there is no reversible terminator nucleotides in the nucleotide mix. If a reversible terminator is included, a modified polymerase may be used to increase the efficiency of incorporation.

Controlled extension can be performed in a variety of temperature settings. Typically, the polymerase used has a preferred or optimal reaction temperature or temperature range. The GC content of the target nucleic acids may be a consideration for selecting an extension temperature. The controlled extension can be performed, for example, at room temperature, about 20° C., about 37° C., about 65° C. or about 70-75° C. The reaction buffer can be selected based upon the polymerase used. Optionally, a pyro-phosphatase/ inorganic phosphatase can be included to remove extension byproducts. In some embodiments, the buffer contains apyrase to digest nucleotides so that the polymerase is only exposed to nucleotides in a short period of time. The apyrase concentration can be adjusted to affect the nucleotide concentration curve during the incorporation period. In some embodiments, a single strand DNA binding protein (SSB) is used in extension reactions to reduce the effect of secondary structures. Other additives such as GC Melt, betaine and formamide can be added at appropriate amounts.

In some embodiments, before the first extension reaction, a buffer containing a polymerase such as the Bst DNA polymerase can be used to incubate the hybridized extension primer/template (target nucleic acid) complex so that the enzyme has sufficient time to bind with the complex. The incubation time can be optimized by measuring extension results. Typically, the extension time is between 30 sec to 10 min.

In the subsequent extension steps, additional polymerase can be added at each step or in some steps to improve overall efficiency of multi-step extensions. In some embodiments, however, polymerase is not added at extension steps, particularly in pulse model where the polymerase remains in the buffer when there are no washing steps.

In some embodiments, instead of missing one or more nucleotides in the extension reaction, one to three types of nucleotides (such dATP, dCTP, dTTP) are mixed with a reversible terminator nucleotide (such as dGTP) and can be used to control the extension. Many reversible terminator nucleotides are suitable for this method and are discussed in, e.g., Wu et al. (2007), 3'-O-modified nucleotides as reversible terminators for pyrosequencing, PNAS vol. 104 no. 42 16462-16467; and Bently et al. (2008), Accurate whole human genome sequencing using reversible terminator chemistry, Nature 456, 53-59, all incorporated herein by reference. In one embodiment, nucleotides that have 3' phosphates are used as reversible terminators. Treatment with alkaline phosphatase can effectively remove the 3' phosphate and reverse the chain termination. For each step, the extension stops at the first base in the template that is complementary to the reversible terminator in the solution (such as a C base in the template and G base in the reversible terminator). There is generally no particular preference for which base is used as the reversible terminator base except when the target templates base composition is known and is biased towards the use of certain bases. For example, it may be preferred to use C or G as reversible terminator if the goal is to maximize extension length for every step. To avoid situations of slow extension for homopolymers (e.g. GGGGG), it is desirable to alternate two or more reversible terminators, e.g., G, C or G, C, A, or G, C, A, T. In some embodiments, the mixture may contain more than two or three reversible terminators with one or two no terminator nucleotides.

After incorporating the reversible terminator base, the unincorporated nucleotides are washed away and the chain termination is reversed by removing the terminating group in the reversible terminator base. The use of reversible terminators in traditional reversible terminator sequencing, particularly when some of the terminators are labeled with fluorescent labels, causes inefficient polymerization and may result in progressive decline in sequencing quality, and further, limit the read length. Using reversible terminators in an extension mixture to extend an extension primer will cause less incorporation inefficiency because these are on average incorporated in every four or five bases in random sequences instead of every step in traditional reversible terminator sequencing. Therefore, a mixture of three no terminator nucleotides with one reversible terminator can extend a sequencing primer efficiently even when reversible terminators are used.

The reversible terminators can be optionally labeled. In such cases, the incorporation can be monitored. In some embodiments, the extension reactions can be monitored by, for example, measuring polymerization byproducts such as pyrophosphate or phosphate or pH changes.

The extended primers can then be used as sequencing primers to determine the sequence of the template. For example, a primer extension product can be extended in the presence of labeled nucleotides to generate a sequence read for the template. Sequencing can be performed using, for example, reversible terminator sequencing, ligation based sequencing, pyrophosphate detection based sequencing, proton detection based sequencing, or any suitable sequencing reaction known in the art.

In one embodiment, sequencing a target nucleic acid comprises incremental base extension, compiling data generated from detecting the presence of bases present in each incrementally extended sequence, and determining the sequence of the target nucleic acid through analyzing the collected data. For example, a plurality of primer extension products of varying lengths are generated or produced for a target nucleic acid sequence serving as a template. The plurality of primer extension products can be used to produce a variety of sequence reads. The sequence of the target polynucleotide molecule can be obtained by assembling the variety of sequence reads. The assembly may comprise stitching together overlapping sequence information, for example, originating from a specific target sequence. The origin of target sequences may be determined, among other methods, by location, by specific target or barcode sequences or any other suitable method known in the art. For example, a barcode specific oligonucleotide can be either used as a seed/extension primer or ligated to a seed/extension primer. The products of the ligation can then be used to prime a sequencing reaction or primer extension reaction.

In one aspect of the present invention, the method comprises sequencing one or more bases of a target nucleic acid by using a first sequencing primer hybridized to a target nucleic acid. Such sequencing can be performed using sequencing by synthesis, for example, step-wise reversible terminator sequencing, incorporating labeled nucleotides, pyrophosphate detection based sequencing, ion detection based sequencing, or alternatively, step-wise ligations, or other methods, thereby obtaining a first sequence read. The first primer and any extension from the primer from the first sequencing can then be released from the target nucleic acid, for example, by denaturing the target nucleic acid via heating the target nucleic acid, contacting the target nucleic acid with sodium hydroxide solution, urea solution, formamide solution, or any other suitable denaturation solution known in the art. The target nucleic acid is then hybridized to a second sequencing primer, which can be the same as the first sequencing primer. A primer extension product is generated by extending the second sequencing primer, such as through controlled limited extension to produce an elongated primer The elongated sequencing primer can be used to sequence one or more bases of the target nucleic acid by using one of many sequencing methods such as step-wise reversible terminator sequencing from the elongated primer, incorporating labeled nucleotides, pyrophosphate detection based sequencing, ion detection based sequencing, step-wise ligations, or other methods, thereby obtaining a second sequence read. The steps of releasing the primer extension product, hybridizing a sequencing primer, extending the sequencing primer to produce an elongated primer, and extending the elongated primer product to obtain a sequence read can be repeated for many times. When these steps are repeated, the controlled extension length may be different. As used herein, "controlled extension" means extension of nucleic acid sequence at specific length. The specific length can be known or unknown. For example, in a three base template dependent extension reaction driven by a nucleic acid polymerase, the extension length can be dependent upon the sequence of the template. Because the template sequence may or may not be known before it is sequenced, the specific extension length may not be known until the template is sequenced or the length is otherwise determined. Nevertheless, the length of extension is generally not random, rather it may be determined by the template sequence. In the case where a cluster of the template molecules, such as in a cluster generated by bridge amplification from a single template or a bead with molecules copied from a single template nucleic acid molecule via emulsion PCR, a majority of the primer extension molecules (e.g. at least 55%, 70%, 85%, 90%, 95%, 99%, 99.9%, 99.99%, 99.999%) hybridized to target nucleic acids in the cluster is extended to the same length in a single step of extension. Some dephasing or prephasing may occur. Over multiple steps of extension, some dephasing or prephasing in an early step may be overcome by one or more late extension steps.

Each primer extension may include one or more cycles of extension and may extend the sequencing primer by a varying number of bases. The plurality of sequence reads can be assembled, such as through overlapping sequence reads, to generate the sequence of the target nucleic acid.

For example, using same initial oligonucleotides for the first seed sequencing primer and if the second primer extension product is shorter than the first sequence read (first primer extension), there will be an overlapping sequence between the first sequence read and the second sequence read. If the second primer extension product is longer than the first sequence read, there can be a gap between the first sequence read and the second sequence read. However, additional sequence reads can be obtained with subsequent extension product removal(s) and one or more new rounds of primer extension to obtain additional sequence reads. Fewer extension steps may be used to have more overlapping sequence results between successive sequencing for more templates. Alternatively, more extension steps can be used to have more non-overlapping sequences.

In general, the length of first sequence read and subsequent reads depend on the sequencing technology used, which can generate different lengths for a given accuracy. Preferably, the sequence read is between 25 to 100 bp, 200 bp, 500 bp, 1kb or up to 2 kb. One of skill in the art would appreciate the order of sequencing may not be significant. For example, long sequences can be obtained with extension and sequencing first and then primer without extension and sequencing.

In some embodiments, a large number of nucleic acid targets are simultaneously sequenced. In such embodiments, the target nucleic acids are typically immobilized on a substrate. At least some target nucleic acids can be spatially separated by forming single molecule clusters that are at least partially non-overlapping. Methods for sequencing a large number of single molecule clusters are well known in the art and kits, instruments and instructions for performing such sequencing have been commercially available from, e.g., Illumina, Inc. (San Diego, Calif.), Life Technologies, Inc. (Foster City, Calif.) Further, sequencing services are available from Complete Genomics, Inc. (Mountain View, Calif.) and Centrillion Biosciences, Inc. (Mountain View, Calif.).

Predicting Controlled Extension Distance

In some embodiments, the extension distance of one or more steps of controlled extensions is estimated by calculating the difference (Pe−Ps) between the extension start position (Ps) and the extension end position (Pe). If the target nucleic acid sequence is known, for each extension step, the stop position can be found by, for example, finding the positions of a target nucleic acid base that is complementary with the missing base in the extension step. The stop position is one base before the first complementary base position. For example, an extension with a nucleotide combination of A, C, and G is used to extend a primer over a template sequence of TTGCATTG. The stop position is base 4 ("C") because the template base A is complement with the missing base "T." If a reversible terminator nucleotide is used in the extension step with three other nucleotides (e.g., A, C, G and terminator T), the stop position should be the first complementary base position (position 5 or first "A"). The start position of a single extension step in a series can be the start position of the series if it is the first extension step. The start position of a single extension step can also be the next complementary target nucleotide to a missing base or one base after the next complementary target nucleotide to a reversible terminator. The total extension distance can be calculated by aggregating the extension distance of each step.

After a target nucleic acid is sequenced, the extension distance can be calculated, for example, as described. However, if the target nucleic acid sequence is unknown, the extension distance can still be estimated by, for example, using simulated random sequences. After the first extension step, the average extension distance of each three nucleotide extension step extends about 4 bases per step. If a reversible terminator is used, the average extension distance of a single extension step, after the first extension step, is about 5 bases per step.

In embodiments where each extension is performed in about 20 seconds, a 1,000 base extension takes on average 250 steps or 1.4 hours. In comparison, in embodiments where each extension is performed in about 10 seconds, the extension time is less than one hour. If a reversible terminator is used, the single step extension time may be longer to allow time for deblocking and other optional steps.

Instrument and Computer Software Products for Controlled Extension Instrument, Automation and Computer Software In some embodiments, controlled extensions are performed in suitable reaction vessels, such as a test tube, a well in a microtiter plate, or a flow cell. While controlled extensions and sequencing can be performed manually, it is more convenient and may be more consistent if some steps are performed with automated equipment.

In some embodiments, controlled extensions are performed using a computer controlled instrument. In one embodiment, nucleotide sets are delivered to the reaction site, such as a lane in a flow cell or a flow chamber of a chip, using a computer controlled pump or an automated pipette. Computer controlled pumps are available from many commercial sources and in many format and specifications. Syringe pumps and peristaltic pumps are particularly suitable for delivering small volumes of reagents in a very short time. Computer software that control the operation of the pumps can be coded using any suitable language known in the art, such as C/C++, objective C, C #, Java, or a variety of scripting languages.

While each reagent such as washing solution or a nucleotide set can be delivered using its own pump, it is often desirable to use a pump in combination with one or more valves. A computer controlled valve can make the system more versatile. In some embodiments, such as IonTorrent by Life Technologies, liquid reagents can be manipulated via pressurized containers creating back pressure onto reagents, rather than using pumps.

Some commercially available sequencers such as the Hiseq 2000, Hiscan Sequencers, MiSeq sequencers and Ion Torrent PGM sequencers include computer controlled reagent delivery systems. These systems may be reprogrammed to perform the sequencing methods in some embodiments.

Other liquid handling equipment, such as the cBot cluster station and MiSeq from Illumina, Inc. and a variety of liquid handling robots, such as the Tecan Freedom Evo and Beckman Coulters Biomek series liquid handling robots can be reprogrammed (using scripts) to perform controlled extensions.

Reagents may be packaged as kits to facilitate automation.

The controlled extensions, including stripping or removing sequencing products, can be performed in line in a sequencer with suitable reagent delivery capability. In some embodiments, a flow cell is sequenced, stripped, extended, and sequenced in a sequencer with the cluster alignment maintained so that the resulting sequence data can be correlated with the correct clusters. Maintaining alignment can be important because a large number of clusters can easily be sequenced simultaneously. Maintaining alignment, however, does not necessarily mean that the flow cell cannot be moved.

For some cluster generation methods, such as the Ion Torrent beads on chip format, aligning different reads to the same cluster/bead is straight forward since each bead has its own coordinate in a chip. For clusters in the Hiseq or MiSeq sequencers, each identified cluster has coordinates and can be located as long as alignment has not changed significantly.

In some embodiments, if the cluster alignment is not maintained between different sequencings, clusters from different sequencing runs may still be correlated by comparing coordinates between two different runs and using overlapping sequences, as well as, alignment to reference sequences. If a consistent pattern of pixel shift is uncovered, a large percentage of clusters in different sequencing runs can still be correlated.

Sequencing

Sequencing by extending a sequencing primer or by extending an extension product can be carried out using a variety of methods. For example, sequencing can be carried out with a labeled reversible terminator or by ligation with a labeled oligonucleotide. Sequencing can be performed using any commercially available method, such as a reversible terminator based sequencing method that is commercially available from companies such as Illumina, Inc. (San Diego, Calif.), Helicos, Inc. (Boston, Mass.), and Azco Biotech, Inc. (San Diego, Calif.).

Sequencing can be accomplished through classic Sanger sequencing methods, which are well known in the art. In some embodiments, a long target nucleic acid (e.g. at least 1,000, 2,000, 10,000, 50,000 bases in length) can be sequenced using controlled extension and sequencing approach. The sequence readout can be carried out using Sanger sequencing which can read about 500-1200 bases per reaction. In one embodiment, the controlled extension is carried out in a series of extension reactions. A 1,800 base long DNA fragment can be sequenced by one Sanger sequence read of 1,000 bases and another Sanger sequence read of 1,000 bases after a controlled extension of about 800 bases. The controlled extension takes about 2-5 hours. In some embodiments, during the controlled extension, preferably in the last step, cleavable nucleotides are used. After Sanger sequencing reaction, the controlled extension product can be removed from the Sanger sequencing product so that the controlled extension product does not add bases to the Sanger fragment. By removing the controlled extension product, the Sanger readout can be performed using standard Sanger sequencing gels or capillary sequencers.

The cleavable nucleotide can be a dUTP. Once incorporated, the uracil from the base U can be released using Uracil-DNA glycosylase (UDG). The resulting apurinic/apyrimidinic (AP) site can be cleaved using, e.g., AP lyase, which can break a DNA fragment. In addition to the dUTP/Glycosylase/AP Lyase system, other suitable cleavable base systems known in the art can also be used.

Sequencing can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read In some embodiments, high-throughput sequencing involves monitoring pH changes during polymerization. In some embodiments, high-throughput sequencing involves the use of technology available by Helicos BioSciences Corporation (Cambridge, Mass.) such as the Single Molecule Sequencing by Synthesis (SMSS) method. SMSS is described in part in US Publication Application Nos. 2006002471 I; 20060024678; 20060012793; 20060012784; and 20050100932.

In some embodiments, high-throughput sequencing involves the use of technology available from 454 Lifesciences, Inc. (Branford, Conn.). Methods for using bead amplification followed by fiber optics detection are described in Marguiles, M., et al. "Genome sequencing in microfabricated high-density picolitre reactors", Nature, doi: 10.1038/nature03959; and well as in US Publication Application Nos. 20020012930; 20030058629; 20030100102; 20030148344; 20040248161; 20050079510, 20050124022; and 20060078909.

In some embodiments, high-throughput sequencing is performed using Clonal Single Molecule Array (Solexa, Inc Allumina, Inc.) or sequencing-by-synthesis (SBS) utilizing reversible terminator chemistry. These technologies are described in part in, e.g., U.S. Pat. Nos. 6,969,488; 6,897, 023; 6,833,246; 6,787,308; and US Publication Application Nos. 20040106130; 20030064398; 20030022207; and Constans, A., The Scientist 2003, 17(13):36.

In some embodiments, high-throughput sequencing of RNA or DNA can take place using AnyDot.chjps (Genovoxx, Germany). In particular, the AnyDot-chips allow for 10×-50× enhancement of nucleotide fluorescence signal detection. AnyDot.chips and methods for using them are described in part in International Publication Application Nos. WO02/088382, WO03/020968, WO03/031947, WO2005/044836, PCT/EP05/105657, PCT/EPOS/105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target nucleic acid molecule having a plurality of bases by the temporal addition of bases via a polymerization reaction that is measured on a molecule of nucleic acid, i e., the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In one embodiment, sequencing can be conducted with labeled nucleotides such as dNTPs with labels. Bases may be detected by extending the incremental fragments via contacting the hybridization complexes sequentially with one of labeled dATP, dCTP, dGTP and dTTP, in the presence of a polymerase, and detecting the incorporation of the labeled dATP, dCTP, dGTP and dTTP to obtain a sequence read from each reaction.

In one embodiment, a mixture of labeled dATP, dCTP, dGTP and dTTP are used. Generally, due to general low incorporation efficiency of the modified dNTPs, such as labeled dNTPs, only the first few bases are extended to generate strong signal. The possibility of "run-on" extension is rather low and the signal generated by such "run-on" extension can be filtered out as noise using methods provided herein or known in the art. In one embodiment, a mixture of labeled ddATP, ddCTP, ddGTP and ddTTP are used, and no "run-on" extension is permitted. In one embodiment, only one round of interrogation that covers all four possible bases is carried for each incremental fragment. For example, sequential addition with one labeled dNTP in each round of interrogation provides possible addition of one detectable base at a time (i.e. on each substrate). This generally results in short read (such as one base or a few bases) that could be assembled for each round. In another embodiment, a longer read is generated with more than one round of interrogation.

In another embodiment, a mixture of labeled ddATP, ddCTP, ddGTP, ddTTP and small amount (<10% (e.g. 5, 6, 7, 8, or 9%) or <20% (e.g., 10, 11, 12, 13, 14, 15, 16, 17, 18, or 19%) of native dATP, dCTP, dGTP, and dTTP are added.

In one embodiment, the labeled nucleotides are reversible terminators. Multiple bases can be detected by the signal strength or in the case of reversible terminator, base addition detection. Nucleotide reversible terminators are nucleotide analogues, which are modified with a reversible chemical moiety capping the 3'-OH group to temporarily terminate the polymerase reaction. In this way, generally only one nucleotide is incorporated into the growing DNA strand even in homopolymeric regions. For example, the 3' end can be capped with an amino-2-hydroxypropyl group. An allyl or a 2-nitrobenzyl group can also be used as the reversible moiety to cap the 3'-OH of the four nucleotides. Examples of reversible terminators include but are not limited to 3'-O-modified nucleotides such as 3'-O-allyl-dNTPs and 3'-O-(2-nitrobenzyl)-dNTPs.

In one embodiment, after detection of the cleavage site present on the solution probe, the 3'-OH of the primer extension products is regenerated through different deprotection methods. The capping moiety on the 3'-OH of the DNA extension product can be efficiently removed after detection of a cleavage site by a chemical method, enzymatic reaction or photolysis, i.e. the cap will be cleaved from the cleavage site. To sequence DNA, in one embodiment, templates containing homopolymeric regions are immobilized on Sepharose beads, and then extension—signal detection—deprotection cycles are conducted by using the nucleotide reversible terminators on the DNA beads to unambiguously decipher the sequence of DNA templates. In one embodiment, this reversible-terminator-sequencing approach is used in the subject methods to accurately determine DNA sequences. (The cap may be referred to herein as a "protective group").

Polynucleotide of the invention can be labeled. In one embodiment, a molecule or compound has at least one detectable label (e.g., isotope or chemical compound) attached to enable the detection of the compound. In general, labels of use in the present invention include without limitation isotopic labels, which may be radioactive or heavy isotopes, magnetic labels, electrical labels, thermal labels, colored and luminescent dyes, enzymes and magnetic particles as well. Labels can also include metal nanoparticles, such as a heavy element or large atomic number element, which provide high contrast in electron microscopy. Dyes of use in the invention may be chromophores, phosphors or fluorescent dyes, which due to their strong signals provide a good signal-to-noise ratio for decoding.

In one embodiment, labels may include the use of fluorescent labels. Suitable dyes for use in the present invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 11th Edition of the Molecular Probes Handbook by Richard P. Haugland, hereby expressly incorporated by reference in its entirety. Commercially available fluorescent nucleotide analogues readily incorporated into the labeling oligonucleotides include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-1 4-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-1 4-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-1 4-UTP (Invitrogen). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Invitrogen), and Cy2, Cy3.5, Cy5.5, and Cy7 (GE Healthcare).

In one embodiment, multiplex detection formats are used for base detection or sequencing. Examples of multiplex formats that can be used include, but are not limited to, either labeled/tagged bead sets (e.g., those produced by Luminex), in which each label is assigned to the individual probe-specific primer, or oligonucleotide arrays on slides, in which specific oligonucleotide spot/position is assigned to the individual probe-specific primer. The limited sequence complexity of the recovered target-specific probes can provide conditions for easier and higher level multiplexing, especially using with universal and Zip-code/ID sequence tags. After the hybridization of the primers to the target-probe complex, the primers can be extended by a nucleotide polymerase. In certain embodiments, the polymerase is selected from an RNA polymerase and a reverse transcriptase.

Where an array is utilized, the detection phase of the process may involve scanning and identifying target polynucleotide sequences in the test sample Scanning can be carried out by scanning probe microscopy (SPM) including scanning tunneling microscopy (STM) and atomic force microscopy (AFM), scanning electron microscopy, confocal microscopy, charge-coupled device, infrared microscopy, electrical conductance, transmission electron microscopy (TEM), and fluorescent or phosphor imaging, for example fluorescence resonance energy transfer (FRET). Optical interrogation/detection techniques include but are not limited to near-field scanning optical microscopy (NSOM), confocal microscopy and evanescent wave excitation. More specific versions of these techniques include far-field confocal microscopy, two-photon microscopy, wide-field epi-illumination, and total internal reflection (TIR) microscopy. Many of the above techniques can also be used in a spectroscopic mode. The actual detection means include charge coupled device (CCD) cameras and intensified CCDs, photodiodes and photomultiplier tubes. These methods and techniques are well-known in the art. Various detection methods are disclosed in U.S. Patent Application Publication No. US 2004/0248144, which is herein incorporated by reference.

For multicolor imaging, signals of different wavelength can be obtained by multiple acquisitions or by simultaneous acquisition by splitting the signal, using RGB detectors or analyzing the whole spectrum (Richard Levenson, Cambridge Healthtech Institutes, Fifth Annual meeting on Advances in Assays, Molecular Labels, Signaling and Detection, May 17-18$^{th}$ Washington D.C.). Several spectral lines can be acquired by the use of a filter wheel or a monochromater. Electronic tunable filters such as acoustic-optic tunable filters or liquid crystal tunable filters can be used to obtain multispectral imaging (e.g. Oleg Hait, Sergey Smirnov and Chieu D. Tran, 2001, Analytical Chemistry 73: 732-739). An alternative method to obtain a spectrum is hyperspectral imaging (Schultz et al., 2001, Cytometry 43:239-247).

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, 7,689,022 and in WO99/47964, each of which also is hereby incorporated by reference in its entirety for all purposes. Fluorescence imaging and software programs or algorithms for DNA sequence analysis and read interpretation are known to one of ordinary skill in the art and are disclosed in Harris T D, et al. "Single-Molecule DNA Sequencing of a Viral Genome" Science 4 Apr. 2008: Vol. 320. no. 5872, pp. 106-109, which is herein incorporated by reference in its entirety. In one embodiment, Phred software is used for DNA sequence analysis. Phred reads DNA sequencer trace data, calls bases, assigns quality values to the bases, and writes the base calls and quality values to output files. Phred is a widely-used program for base calling DNA sequencing trace files. Phred can read trace data from SCF files and ABI model 373 and 377 DNA sequencer chromat files, automatically detecting the file format. After calling bases, Phred writes the sequences to files in either FASTA format, the format suitable for XBAP, PHD format, or the SCF format. Quality values for the bases are written to FASTA format files or PHD files, which can be used by the phrap sequence assembly program in order to increase the accuracy of the assembled sequence. The quality value is a log-transformed error probability, specifically $Q=-10 \log_{10}(P_e)$ where Q and $P_e$ are respectively the quality value and error probability of a particular base call. The Phred quality values have been thoroughly tested for both accuracy and power to discriminate between correct and incorrect base-calls. Phred can use the quality values to perform sequence trimming.

DNA polymerase based sequencing reactions generally possess efficiency problems. Native nucleotides can be incorporated at a relatively high efficiency, compared to reduced efficiency incorporation of non-native nucleotides, such as labeled nucleotides or reversible terminators. Thus, in a growing strand of a nucleotide extension reaction, the likelihood of elongation drops as a function of the extended length. Thus, even slight differences in single nucleotide incorporation efficiency can lead to significant differences, as the reaction proceeds. The reduced incorporation efficiency accounts for increased error rates and hence decreased sequence information quality along growing strands. The resulting sequence information consists of relatively short sequence reads that have been terminated due to unacceptably low correct sequence signal. The present invention provides methods and compositions to overcome these problems in sequencing reactions. A seed primer can be extended using high incorporation efficiency nucleotides, such as native nucleotides. Accordingly, a large population of templates can be primed further and further downstream to start a sequencing reaction, for example n bases downstream as compared to another sequencing primer. The sequencing reaction at the start position would start with a high overall efficiency and continue s bases, until the quality of the sequencing information drops below an acceptable level. Due to the initial n bases, sequence information can be obtained down to n+s bases on the target template. Sequencing primers of different length can thus provide sequencing information that ends n bases apart. By varying the length n of high efficiency extension reactions prior to sequencing, overlapping sequence information of high quality can be obtained from a single template. In various embodiments, a set of sequencing primers are used that start sequencing reactions less than 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200 or more bases apart. In some embodiments, sequence information for up to 500, 1000, 2000 or more bases are obtained. Methods described herein, allow for obtaining sequence information for up to 500, 1000, 2000 or more bases in over 80, 90, 95, 98, 99, 99.5, 99.9%, or more of the templates.

In one embodiment, one detection cycle is performed by adding labeled A, C, G, T sequentially followed by washing and detecting after each addition. In one embodiment, multiple detection cycles can be performed using nucleotides with removable labels.

In one embodiment, the series of incremental fragments are further extended (thus, serving as sequencing primer) for sequencing reactions to obtain the sequence information of the target molecules. The sequence information is a series fragment sequences that are adjacent on the target molecule, which can be assembled to obtain a long fragment or the full length sequence of the target molecule.

In one embodiment of the present invention, serial sequencing of a target polynucleotide is converted to parallel sequencing to reduce the time required for sequencing a given number of bases of the target polynucleotide.

Immobilized Target

In one embodiment, a nucleic acid target is attached to a substrate or immobilized on a substrate. The substrate can be a bead, flat substrate, flow cell or other suitable surfaces. In one embodiment, the substrate comprises glass.

In one embodiment, a target nucleic acid is attached or immobilized to a substrate via a capture probe. A capture probe is an oligonucleotide that is attached to the surface of a substrate and is capable to bind to a sequencing template. Capture probes can be of various lengths, such as from 18 bases to 100 bases, such as 20 bases to 50 bases.

In one embodiment, the capture probe has a sequence that is complementary to the sequencing template. For example, if the present method is used to sequence a genome with at least partial sequence known already, capture probes can be designed to complement to the known sequences. In one embodiment, the capture probes are complementary to "barcode" or "identifier" sequence added to the sequencing templates via, e.g., specific ligation, as a part of the primer for PCR reaction. In such reactions, a sequencing template-specific primer and a primer comprising a unique barcode are used for the amplification, thus all the target molecules with the same sequences have the same barcode attached.

The capture probe can be attached to the substrate at either the 5' end or the 3' end. In some embodiments, the capture probe is attached to the substrate at the 5' end, and the 3' end of the capture probe can be extended by the incorporation of nucleotides as described herein to generate incremental extension fragments which can in turn be sequenced by further incorporation of labeled nucleotides. In another embodiment, the capture probe is attached to the substrate at the 3' end, and the 5' end of the capture probe cannot be extended by the incorporation of nucleotides. A second probe (or sequencing primer) hybridizes to the sequencing template and its 3' end is extended by the incorporation of nucleotides as described herein to generate an incremental extension fragment which can in turn be sequenced by further incorporation of labeled nucleotides. In this case, the extension is towards the direction of the capture probe. In general, the sequencing primer hybridizes to a linker introduced to the end of the sequencing template when generated, either directly from a genomic DNA or from a parent target molecule. Thus a seed/sequencing primer that is a "universal primer" can be used to sequence different target molecules. In one embodiment, sequencing primers specific to the target molecule are used.

In one embodiment, the capture probe is immobilized on a solid support before binding to the sequencing template. In one embodiment, the 5' end of a capture probe is attached to a solid surface or substrate. A capture probe can be immobilized by various methods known in the art including, without limitation, covalent cross-linking to a surface (e.g., photochemically or chemically), non-covalent attachment to the surface through the interaction of an anchor ligand with a corresponding receptor protein (e.g. biotin-streptavidin or digoxigenin-anti-digoxigenin antibody), or through hybridization to an anchor nucleic acid or nucleic acid analog. The anchor nucleic acid or nucleic acid analog have sufficient complementarity to the sequencing template (i.e., the formed duplex has sufficiently high $T_m$) that the anchor-sequencing template-probe complex will survive stringent washing to remove unbound targets and probes, but they do not overlap with the target site that is complementary to the probe antisense sequence.

In one embodiment, a capture template or target nucleic acid is used as a template for bridge amplification. In such embodiments, two or more different immobilized probes are used. In some cases, single molecule templates are used to generate clusters of nucleic acids on a substrate by bridge amplification. In one embodiment, each of the clusters of nucleic acids contains substantially the same (>95%) type of nucleic acids because they are derived from a single template nucleic acid. These clusters are typically referred to as single molecule clusters. Such substrates with single molecular clusters can be produced using, for example, the method described in Bently et al., Accurate whole human genome sequencing using reversible terminator chemistry, Nature 456, 53-59 (2008), incorporated herein by reference, or using commercially available kit and instrument from, for example, Illumina, Inc. (San Diego, Calif.).

Another method for generating suitable nucleic acids for sequencing is described in Church et al., US Patent Application Publication No. US20090018024 A1, incorporated herein by reference. Additional exemplary methods for generating a suitable template for sequencing include emulsion PCR with DNA capture, with beads that are used to create random arrays (commercially available from, for example, Life Technologies, Inc.) or nanoballs created after rolling circle amplification of constructs that contact target molecules and deposition on patterned arrays (commercial service using the technology is available from, for example, Complete Genomics, Inc.).

The solid substrate can be made of any material to which the molecules can be bound, either directly or indirectly. Examples of suitable solid substrates include flat glass, quartz, silicon wafers, mica, ceramics and organic polymers such as plastics, including polystyrene and polymethacrylate. The surface can be configured to act as an electrode or a thermally conductive substrate (which enhances the hybridization or discrimination process). For example, micro and sub-micro electrodes can be formed on the surface of a suitable substrate using lithographic techniques. Smaller nanoelectrodes can be made by electron beam writing/lithography. Electrodes can also be made using conducting polymers which can pattern a substrate by ink-jet printing devices by soft lithography or be applied homogenously by wet chemistry. $TnO_2$ coated glass substrates are available. Electrodes can be provided at a density such that each immobilized molecule has its own electrode or at a higher density such that groups of molecules or elements are connected to an individual electrode. Alternatively, one electrode may be provided as a layer below the surface of the array which forms a single electrode. The solid substrate may optionally be interfaced with a permeation layer or a buffer layer. It is also possible to use semi-permeable membranes such as nitrocellulose or nylon membranes, which are widely available. The semi-permeable membranes can be mounted on a more robust solid surface such as glass. The surface layer may comprise a sol-gel. The surfaces may optionally be coated with a layer of metal, such as gold, platinum or other transition metal. A particular example of a suitable solid substrate is the commercially available SPR BIACore™ chip (GE Healthcare). Heaton et al., 2001 (PNAS 98:3701-3704) have applied an electrostatic field to an SPR surface and used the electric field to control hybridization.

The solid substrate is generally a material having a rigid or semi-rigid surface. In one embodiment, at least one surface of the substrate is substantially flat, although in some embodiments it may be desirable to physically separate discrete elements with, for example, raised regions or etched trenches. For example, the solid substrate may comprise nanovials—small cavities in a flat surface e.g. 10 jun in diameter and 10 μm deep. Other formats include but are not limited to synthetic or natural beads, membranes or filters, slides including microarray slides, microtiter plates, microcapillaries, and microcentrifuge tubes.

In one embodiment, oligonucleotide capture probes are coated or attached onto beads for capturing the sequencing templates. Hybridization between capture probes and sequencing template polynucleotides can be carried out on beads in columns at a controlled temperature and salt concentration. The hybridization products can be eluted from the beads with moderate pressure.

The use of a solid support with an array of capture oligonucleotides is disclosed in U.S. Pat. No. 6,852,487, which is hereby incorporated by reference.

Loading of nucleic acids onto these substrates can be modulated and/or controlled by the flow and/or electrical forces, including diffusion forces and surface forces exerted by areas of differential charge and/or hydrophobicity. The number of nucleic acids applied to the substrate (i.e., with a loading buffer or other solution) can be adjusted to assure maximal occupancy of the linear features with non-overlapping nucleic acid molecules and thus minimize the number of empty linear features on the substrate. In an exemplary embodiment, at least 50% of the linear features of a substrate are occupied by at least one nucleic acid molecule. In a further embodiment, at least 60%, 70%, 80%, 90%, and 95% of the linear features are occupied by one or more nucleic acids.

Two exemplary approaches of laying probes are disclosed herein below for illustrative purposes. The first approach is in situ oligonucleotide synthesis in which the probes are in known geographic locations in the X-Y coordinate plane. In one embodiment, the oligonucleotide probe is synthesized on the surface. Examples of technologies that allow on-surface oligo synthesis include but are not limited to photolithography and ink jet. In another embodiment, the pre-synthesized oligonucleotide probes are spotted onto the surface. Various microarray protocols, for example, protocol for Agilent inkjet-deposited pre-synthesized oligo arrays are known to one skilled in the art.

Polymers such as nucleic acids or polypeptides can be synthesized in situ using photolithography and other masking techniques whereby molecules are synthesized in a step-wise manner with incorporation of monomers at particular positions being controlled by methods of masking techniques and photolabile reactants. For example, U.S. Pat. No. 5,837,832 describes a method for producing DNA arrays immobilized to silicon substrates based on very large scale integration technology. In particular, U.S. Pat. No. 5,837,832 describes a strategy called "tiling" to synthesize specific sets of probes at spatially-defined locations on a substrate. U.S. Pat. No. 5,837,832 also provides references for earlier techniques that can also be used. Light directed synthesis can also be carried out by using a Digital Light Micromirror chip (Texas Instruments) as described (Singh-Gasson et al., (1999) Nature Biotechnology 17:974-978). Instead of using photo-deprotecting groups which are directly processed by light, conventional deprotecting groups such as dimethoxytrityl can be employed with light directed methods where, for example, a photoacid molecule bearing a chromophore capable of receiving UV radiation is generated in a spatially addressable way which selectively deprotects the DNA monomers (McGall et al PNAS 1996 93: 1355-13560; Gao et al J. Am. Chem Soc. 1998 120: 12698-12699). Electrochemical generation of acid is another method that can be used in the subject methods of the present invention.

The in situ arrays can have about 1 to 10, 10 to 100, 100 to 1000, or 1,000 to 100,000,000 probes. The in situ arrays can have more than 100,000,000 array probes. In one embodiment, the in situ array carries approximately 200,000,000 probes.

Molecules that can be immobilized in the array include nucleic acids such as DNA and analogues and derivatives thereof, such as PNA. Nucleic acids can be obtained from any source, for example genomic DNA or cDNA or synthesized using known techniques such as step-wise synthesis. Nucleic acids can be single or double stranded. DNA nanostructures or other supramolecular structures can also be immobilized. Other molecules include but are not limited to compounds joined by amide linkages such as peptides, oligopeptides, polypeptides, proteins or complexes containing the same; defined chemical entities, such as organic molecules; conjugated polymers and carbohydrates or combinatorial libraries thereof.

In one embodiment, the biotinylated beads are used to anchor the target sequence and the sequencing is carried out by performing the base incorporation in the bead system.

In another embodiment, a "chip" is a substrate for immobilizing or attached a target. The geometric design of the chip can vary. For example, the chip can be a tube with the usable surface inside. Chips can be in flow cell format to facilitate liquid handling. In one embodiment, the chips are allele specific sequencing chips as disclosed in PCT/US2010/048526, herein is incorporated by reference.

In one embodiment, the chip is a membrane multichip. A multilayered substrate with holes (e.g. 1 micron to 50 micron) is generated. Target molecules are loaded into the holes with some holes containing a single molecule target. Targets are amplified within holes. The layers are peeled off. Each layer has some molecules attached to the holes. The layers are substantially similar in terms of molecules (copies of each other). These layers can be directly used or transferred to a suitable sequencing substrate for sequencing.

Other chips can also be used in the present invention, include but are not limited to photo cleavable oligo multichip, multilayer substrates with holes, and nanoprinting chip.

In one embodiment, the biotinylated beads are used to anchor the target sequence and the sequencing is carried out by performing the base incorporation in the bead system.

An immobilized or attached target nucleic acid can then be hybridized with a primer (or multiple primers). Polymerase in its suitable buffer is then added to make contact with the immobilized or attached template or target nucleic acid. The primer can be used directly as a sequencing primer or can be used as a seed primer to generate primer extension products of various lengths. These primer extension products can further be used as sequencing primers in a sequencing reaction. Primer extension reactions are discussed in further detail elsewhere herein. A controlled extension reaction may be chosen to generate primer extension products. The buffer may contain a set of nucleotides (1-3 nucleotides of the four possible nucleotides) or the set of nucleotides can be added later to start the reaction. After a suitable amount of time (such as approximately, 5, 10, 15, 20, 25, or 30 to 90 second for native bases), the buffer solution is removed and the immobilized template is washed to remove the nucleotides. Optionally, nucleotide degrading enzymes such as apyrase or alkaline phosphatase are added into the reaction buffer at the end of the reaction and/or in the washing solution to minimize contamination of the next round of extension with nucleotides from the previous extension.

In some embodiments, primer extension is performed using a pulse method, such as described herein. In some embodiments, the immobilized template is contacted with a multi-enzyme buffer that contains a polymerase (such as Klenow exo(−) for DNA sequencing), one or several nucleotide degrading enzymes such as apyrase, alkaline phosphatase. Optionally, an inorganic pyrophosphatase is added to degrade pyrophosphate generated by polymerase reaction. Sets of nucleotides are successively added to the reaction buffer at interval of 30-90 seconds (preferably 30 seconds). Nucleotides are utilized by the polymerase for polymerase reaction and at the same time, are degraded by apyrase or alkaline phosphatase.

Template Cluster

For sequencing multiple target polynucleotides (or fragments of a single large polynucleotide target), a large number of different target polynucleotides or its fragments can be immobilized on a substrate. Such a substrate is replicated many times to produce a set of the substrates.

In one embodiment, a plurality of target nucleic acids or templates are immobilized on substrates and each template cluster is originated from a single molecule (see for example, Bentley et al., Nature 456, 53-59, (2008) and its supplement, incorporated herein by reference in its entirety). Because the location of the template cluster are known, a first sequence from the first round of sequencing and second sequence from a second round of sequencing for the same template can be readily determined.

In one embodiment, parallel sequencing is performed. In parallel sequencing, commonly referred to as next generation sequencing, millions or more template (clusters) are sequenced simultaneously often with a single primer. In one embodiment, nucleotide addition is optimized to control primer extension length.

In another embodiment, a fixed sequence of nucleotide addition such as step one: dATP, dCTP, dGTP; step two, dCTP, dGTP, dTTP; step three: dGTP, dTTP, dATP; step four; dTTP, dATP, dCTP; step five: dATP, dCTP, dGTP, and so forth, is used to control the length of the primer extension. Because template sequences vary, the resulting extended primer length varies.

In one embodiment, multiple targets such as 10,000, 100,000, 1 million, 10 million, or 100 million sequences or targets are sequenced simultaneously. Thus, for each substrate, there are a plurality of capture sites with each capture sites have different capture probes that recognize different targets (sequencing templates). If the targets are fragments of a longer sequence, contigs can be assembled to obtain the longer sequence, such as the whole genome sequence. In general, multiple target sequencing is typically done in chip format, but it can be performed in bead format as well.

In one embodiment, the chip comprises random clusters started with single molecules (such as Illumina flow cells). The molecular clones of target molecules can be printed to many substrates to create replicate substrates for sequencing. In one embodiment, the chips are duplicating chips by nylon membrane impression and printing or other methods known in the art.

Sequencing System

Figure 7:
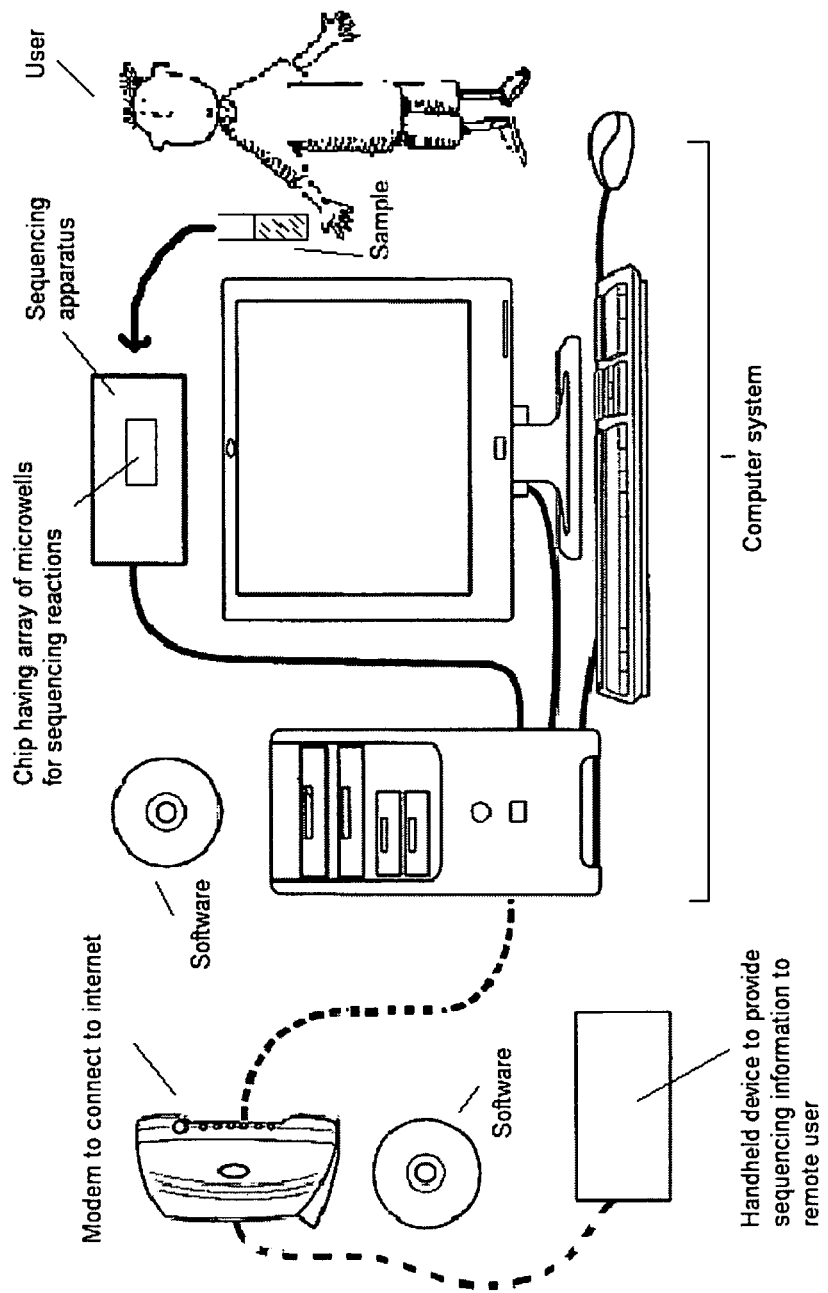
FIG. 7 depicts that nucleic acid sequence information can be obtained, processed, analyzed and/or assembled via a computer system.

In another aspect, the present invention provides a system for sequencing. In some embodiments, one or more methods of sequencing disclosed herein are performed by a system, such as an automated sequencing system instrument controlled by a user (e.g., as schematically depicted in FIG. 7). In one embodiment, the user controls a computer which may operate various instrumentation, liquid handling equipment or analysis steps of the invention. In one embodiment, a computer controlled collection, handling, or analysis system is used to control, activate, initiate, continue or terminate any step or process of the methods as herein described. In one embodiment, a computer device is used to control, activate, initiate, continue or terminate the handling and/or movement of fluids or reagents into and through the system or device as herein described, the handling or movement of one or more reagents to one or more chambers or plurality of chambers in one or more cartridges, the obtaining or analysis of data, etc. In one embodiment, chips of the sequencing reaction are placed in one or more chambers/flow cells or plurality of chambers/flow cells in one or more cartridges. The chips may comprise substrates which provide sites for the sequencing reactions.

In one embodiment, the computer is any type of computer platform such as a workstation, a personal computer, a server, or any other present or future computer. The computer typically includes known components such as a processor, an operating system, system memory, memory storage devices, and input-output controllers, input-output devices, and display devices. Such display devices include display devices that provides visual information, this information typically may be logically and/or physically organized as an array of pixels. In one embodiment, a graphical user interface (GUI) controller is included that comprises any of a variety of known or future software programs for providing graphical input and output interfaces. In one embodiment, GUI's provide one or more graphical representations to the user, and are enabled to process the user inputs via GUI's using means of selection or input known to those of ordinary skill in the related art.

It will be understood by those of ordinary skill in the relevant art that there are many possible configurations of the components of a computer and that some components that may typically be included in a computer are not described, such as cache memory, a data backup unit, and many other devices. In the present example each execution core may perform as an independent processor that enables parallel execution of multiple threads.

In one embodiment, the processor executes operating system, which is, for example, a WINDOWS™ type operating system (such as WINDOWS™ XP) from the Microsoft Corporation; the Mac OS X operating system from Apple Computer Corp. (such as 7.5 Mac OS X v10.4 "Tiger" or 7.6 Mac OS X v10.5 "Leopard" operating systems); a UNIX™ or Linux-type operating system available from many vendors or what is referred to as an open source; or a combination thereof. The operating system interfaces with firmware and hardware in a well-known manner, and facilitates processor in coordinating and executing the functions of various computer programs that may be written in a variety of programming languages. The operating system, typically in cooperation with the processor, coordinates and executes functions of the other components of computer. The operating system also provides scheduling, input-output control, file and data management, memory management, and communication control and related services, all in accordance with known techniques.

In one embodiment, the system memory is of a variety of known or future memory storage devices. Examples include any commonly available random access memory (RAM), magnetic medium such as a resident hard disk or tape, an optical medium such as a read and write compact disc, or other memory storage device. Memory storage devices may be any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette.

In one embodiment, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

In one embodiment, input-output controllers include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers could include controllers for any of a variety of known display devices for presenting information to a user, whether a human or a machine, whether local or remote. In one embodiment, the functional elements of computer communicate with each other via system bus. Some of these communications may be accomplished in alternative embodiments using network or other types of remote communications.

In one embodiment, applications communicate with, and receive instruction or information from, or control one or more elements or processes of one or more servers, one or more workstations, and/or one or more instruments. In one embodiment, a server or computer with an implementation of applications stored thereon are located locally or remotely and communicate with one or more additional servers and/or one or more other computers/workstations or instruments. In one embodiment, applications are capable of data encryption/decryption functionality. For example, it may be desirable to encrypt data, files, information associated with GUI's or other information that may be transferred over network to one or more remote computers or servers for data security and confidentiality purposes.

In one embodiment, applications include instrument control features, where the control functions of individual types or specific instruments such as a temperature controlling device, imaging device, or fluid handling system are organized as plug-in type modules to the applications. In one embodiment, the instrument control features include the control of one or more elements of one or more instruments that, for instance, include elements of a fluid processing instrument, temperature controlling device, or imaging device. In one embodiment, the instrument control features are capable of receiving information from the one or more instruments that include experiment or instrument status, process steps, or other relevant information. In one embodiment, the instrument control features are under the control of an element of the interface of the applications. In one embodiment, a user inputs desired control commands and/or receive the instrument control information via one of GUI's.

In one embodiment, the automated sequencing system is controlled by a first user, conducts sequencing methods described herein, analyzes the raw data as described herein, assembles sequence reads as described herein, and then send the sequencing information to a remote second user at a location different from that of the first user.

Processing of Data and Data Analysis

In one embodiment, identifying target polynucleotide sequence and integrating sequences to assemble genomic information is carried out with a computer. In one embodiment, the present invention encompasses a computer software or algorithm designed to analyze and assemble sequence information obtained via the methods of the present invention.

In terms of sequence read interpretation for the in situ arrays, reads at array features correspond to X-Y coordinates that map to the loci of interest. A "read" typically refers to an observed sequence derived from raw data, such as the order of detected signals corresponding to the cyclical addition of individual nucleotides. In one embodiment, the reads are checked against the expected reference genome sequence at the 10-bp loci for quality control. A reference sequence enables the use of short read length. Reads that have passed the quality control check are then combined to generate a consensus sequence at each locus. In one example, there are 10 unique probes per locus of interest minus any reads that have failed the quality control checks.

In terms of sequence read interpretation for the "lawn" approach, the reads are at random locations on a surface, e.g. a flow cell. In one embodiment, the reads are checked against the expected subset of reference genome sequence at the loci of interest for quality control. Reads that have passed the quality control check are mapped to the individual locus of interest. Reads corresponding to each locus are then combined to generate a consensus sequence. In one embodiment, there are more than 3,000 reads per 10-bp locus.

Assembly of Sequence Reads

In one embodiment, the present invention provides a method for obtaining the sequence information of the target molecules by assembling the sequence reads from each of the substrates. The sequence reads can be obtained by base extension of a series of polynucleotide with different lengths due to the different base extension of the same capture probe using the same target molecules, such as described above. As such, they represent continued fragments of the target molecule sequence and can be assembled to provide the continue sequence of the target molecule.

A computer program can be used to track the sequence reads obtained from the same capture probes on different substrates for the assembly.

In some embodiments, sequencing information originating from a single template is identified using a unique identifier of the template, such as the template location or a tag sequence. Overlapping sequence information can be stitched together to generate longer sequence information from a single template. In some embodiments, a template's complement is also sequenced. In some embodiments, sequence information is stitched together using sequence reads generated both from the template and its complement.

Applications

The methods of the present invention provide several advantages. In one embodiment, the sequencing methods provided herein permit the use of unmodified nucleotide and enzymes, which utilize the natural nucleic acid synthesis chemistry. This not only reduces the cost, but also increases the accuracy because the high-fidelity chemistry generated by the evolution process.

The sequencing method provided by the present invention can be used to sequence DNA/RNA. It can be used to sequence pathogens/microbial genomes to identify species/strains quickly. One advantage of the sequencing method provided by the present invention is that is can accommodate low efficiency sequencing chemistry (reversible terminators, ligations, etc.), thus reduces the time to sequence. In addition, the method can sequence very long fragments (e.g. 100-10000 base pairs or more).

Furthermore, when loci- and allele-specific sequencing templates are used, they are SNP capable, and can carry multiple signal-reporting labels or ligands, providing for a higher level of multiplexing of diverse target sequences.

Thus, the present invention can provide low-cost, high-throughput and accurate methods for sequencing target polynucleotides with long reads. In some embodiments, the long reads are assembled from sequencing reads obtained using available sequencing technologies discussed herein and assembled using the methods, compositions, and systems of the inventions.

The sequencing methods of the present invention can be multiplexed to a very high degree. In one embodiment, samples can comprise pooled genomes of target and control subject populations respectively. Populations can be of any sex, race, gender or age. Populations can also include animal subjects, particularly mammalian subjects such as dog, cat, horse, mouse, rat, etc., screened for veterinary medicine or pharmaceutical drug development purposes.

In some embodiments, the target polynucleotide is DNA, for example DNA composing at least 50% of a genome of an organism. Some embodiments further comprise identifying and/or counting a gene sequence of more than one cell, and correlating sequence information from the various cells. Such embodiments find application in medical genetics. Other embodiments compare DNA sequences of normal cells to those of non-normal cells to detect genetic variants. Identification of such variants finds use in diagnostic and/or prognostic applications.

In some embodiments, enumeration may determine changes in gene number, indicating, for example that a gene appears three times instead of two times (as in a trisomy) or a gene fails to appear (such as a homozygous deletion). Other types of allelic loss and changes change in diploidy may also be determined, including changes related to, for example, a somatic recombination, a translocation, and/or a rearrangement, as well as a sporadic mutation.

Such embodiments find use in diagnostic and prognostic applications, also featured in the present invention. For example, a homozygous deletion may indicate certain forms of cancer. It will be appreciated by those of skill in the art that other diseases, disorders, and/or conditions may also be identified based on recognized changes in diploidy. For example, three copies of chromosome 21 genes can indicate trisomy 21, associated with Down syndrome.

Detection of Genetic Variants

Methods of the present invention allow rapid analysis of DNA sequences at the single molecule level, lending themselves to applications relying on detailed analysis of individual sequences. Additional aspects of the present invention include such applications.

For example, certain embodiments provide for SNP detection, by identifying incorporation of a single nucleotide into a complementary strand of a target polynucleotide sequence at the site of a known SNP. Any of the variations, embodiments, and/or aspects of the present invention may be used for such SNP detection. Such methods can also be used to identify other variants due to point mutations, including a substitution, frameshift mutation, an insertion, a deletion, and inversion, a missense mutation, a nonsense mutation, a promoter mutation, a splice site mutation, a sporadic mutation and the like.

Moreover, the invention also features methods of diagnosing a metabolic condition, a pathological condition, a cancer and other disease, disorder or condition (including a response to a drug) by identifying such genetic variants. For example, a known wild type versus a known variant can be distinguished using the methods described herein. Whether a target polynucleotide exhibits the wild type or variant sequence can readily be determined by the methods of the present invention. Furthermore, the long sequence information originating from single templates can provide haplotyping information that is otherwise difficult to obtain. The haplotyping information linking two or more loci, can be used in genetic analysis.

Certain embodiments provide for detection of additional genetic variants, by identifying incorporation of more than one nucleotide into a complementary strand of a target polynucleotide sequences, either at substantially known regions of variation or at substantially unknown regions. Any of the variations, embodiments, and aspects of the present invention may be used for such detection. Comparison of sequences from more than one individual allows identification of genetic variants, including substitutions, frameshift mutations, insertions, deletions, inversions, missense mutations, nonsense mutations, promoter mutations, splice site mutations, sporadic mutations, a duplication, variable number tandem repeats, short tandem repeat polymorphisms, and the like.

In another embodiment, the sequencing method provided herein use single molecule counting for accurate analysis of allele frequencies and/or haplotype frequencies. Since more than a single site on each molecule can be probed, haplotype information can be easily determined. In another embodiment, the present methods and systems disclosed herein can be used to obtain haplotype frequencies. Such methods can be applicable to association studies, where genotype frequencies (such as SNP frequencies) are correlated with diseases in a population. The expense of single SNP typing reactions can be prohibitive when each study requires the performance of millions of individual reactions; the present invention permits millions of individual reactions to be performed and analyzed on a single array surface.

In one embodiment, the sequencing methods provided herein are used for identifying high value polymorphisms located in regulatory elements and coding regions for a number of drug metabolizing enzyme and transporter (DMET) genes. In one embodiment, information on the expression of DMET genes provides information on the absorption, distribution, metabolism, and excretion profiles of a drug. In one embodiment, the methods of the present invention provide for information collected on the complex transcriptional responses to various drugs and subsequent prediction of physiological effects is important for the development of effective therapeutics. In one embodiment, the sequencing methods provided herein are used to draw links between gene expression profiles and physiological effects. Physiological effects can include a subjects' likely response to a drug candidate.

A wide variety of diseases can be detected by the process of the present invention. In one embodiment, the sequencing methods provided herein are used for detecting infectious diseases. Infectious diseases can be caused by a pathogen, such as a bacterial, viral, parasitic, or fungal infectious agent. In one embodiment, resistance of various infectious agents to drugs is determined using the methods of the present invention.

In one embodiment, the sequencing methods provided herein are used to sequence pathogens/microbial. In one embodiment, the sequencing methods provided herein are used to identify species/strains. In one embodiment, the sequencing methods provided herein are used to sequence pathogens/microbial and to identify species/strains.

For example, the sequencing method provided herein can be used for detecting one or more microbes. Detection of a microbe can be by sequencing PCR products from a microbe, such as a virus or bacteria. For example, a viral or bacterial PCR product can be hybridized with 5'-3' chips (direct sequencing) or 3'-5' chips (requires additional sequencing primer). In one embodiment, approximately 20-50 bases or longer sequencing is used, to detect a microbe. In one embodiment, about 10-20 chips, wherein a chip density of 10k can produce approximately 200k to 500k base sequence, is used.

The invention also provides methods of diagnosing a metabolic condition, a pathological condition, a cancer, and/or other disease, disorder or condition (including a response to a drug) by identifying such genetic variants. In one embodiment, detection is carried out by prenatal or post-natal screening for chromosomal and genetic aberrations or for genetic diseases. In some embodiments, an identified sequence variant indicates a disease or carrier status for a genetic condition. Examples of detectable genetic diseases include, but are not limited to, 21 hydroxylase deficiency, adenomatous polyposis coli, adult polycystic kidney disease, α1-antitrypsin deficiency, cystic fibrosis, familial hypercholesterolemia, Fragile X Syndrome, hemochromatosis, hemophilia A, hereditary nonpolyposis colorectal cancer, Marfan syndrome, myotonic dystrophy, neurofibromatosis type 1, osteogenesis imperfecta, retinoblastoma, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, diabetes, as well as cleft lip, club foot, congenital heart defects, neural tube defects, pyloric stenosis, alcoholism, Alzheimer disease, bipolar affective disorder, cancer, diabetes type I, diabetes type II, heart disease, stroke, and schizophrenia.

Genetic Cancer Research and Detection

In one embodiment, the sequencing methods provided herein are used to detect a cancer or for performing genetic cancer research, where sequence information from a cancer cell is correlated with information from a non-cancer cell or with another cancer cell in a different stage of cancer. In certain embodiments, sequence information may be obtained, for example, for at least about 10 cells, for at least about 20 cells, for at least about 50 cells, for at least about 70 cells, and for at least about 100 cells. Cells in different stages of cancer, for example, include a colon polyp cell vs. a colon cancer cell vs. a colon metastasizing cell from a given patient at various times over the disease course. Cancer cells of other types of cancer may also be used, including, for example a bone cancer, a brain tumor, a breast cancer, an endocrine system cancer, a gastrointestinal cancer, a gynecological cancer, a head and neck cancer, a leukemia, a lung cancer, a lymphoma, a metastases, a myeloma, a pediatric cancer, a penile cancer, a prostate cancer, a sarcoma, a skin cancer, a testicular cancer, a thyroid cancer, and a urinary tract cancer. In one embodiment, detection of a cancer involves detection of one or more cancer markers. Examples of cancer markers include, but are not limited to, oncogenes, tumor suppressor genes, or genes involved in DNA amplification, replication, recombination, or repair. Specific examples include, but are not limited to, BRCA1 gene, p53 gene, APC gene, Her2/Neu amplification, Bcr/Abl, K-ras gene, and human papillomavirus Types 16 and 18. The sequencing methods provided herein can be used to identify amplifications, large deletions as well as point mutations and small deletions/insertions or other mutations of genes in the following human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

For example, to screen for a cancer marker, the genomic DNA from subject can be prepared as a sequencing template and can be allowed to bind a capture probe fixed to a substrate. In this example there can be multiple substrates each with the same capture probe wherein each substrate can then be exposed to an identical version of the sequencing template. After removal of any unbound sequencing template, the arrays, or chips, are then subjected to incremental base extension. The capture probes can serve as a primer and specifically bind to a region of the sequencing template near a location that can be use for detecting a relevant distinction indicating a disease. In the case of cancer and screening Bcr/Abl, the capture probes can bind in close proximity to the expected translocation site. Incremental extensions of the bases can reveal whether or not the sequencing template contains DNA from only one gene in the region of interest or that from a translocated gene region. After reading the results from step-wise hybridization events across the multiple chips, and processing the raw data, once can then determine if a subject's DNA has a Bcr/Abl translocation, and therefore detect the presence of a genetic sequence indicative of cancer.

In one embodiment, the sequencing methods of the present invention are used for environmental monitoring. Environmental monitoring includes but is not limited to detection, identification, and monitoring of pathogenic and indigenous microorganisms in natural and engineered ecosystems and microcosms such as in municipal waste water purification systems and water reservoirs or in polluted areas undergoing bioremediation. In one embodiment, the methods of the present invention are used to detect plasmids containing genes that can metabolize xenobiotics, to monitor specific target microorganisms in population dynamic studies, or either to detect, identify, or monitor genetically modified microorganisms in the environment and in industrial plants.

In one embodiment, the sequencing methods provided herein are used in a variety of forensic areas. Examples of forensic areas include, but are not limited to, human identification for military personnel and criminal investigation, paternity testing and family relation analysis, HLA compatibility typing, and screening blood, sperm, and transplantation organs for contamination.

In the food and feed industry, the present invention has a wide variety of applications. In one embodiment, the sequencing methods provided herein are used for identification and characterization of production organisms. Examples of production organisms include, but are not limited to, yeast for production of beer, wine, cheese, yogurt, and bread. In one embodiment, the methods of the present invention are used for quality control and certification of products and processes (e.g., livestock, pasteurization, and meat processing) for contaminants. In one embodiment, the sequencing methods provided herein are used for characterization of plants, bulbs, and seeds for breeding purposes, identification of the presence of plant-specific pathogens, and detection and identification of veterinary infections.

RNA Applications

In some embodiments, the target polynucleotide is RNA, and/or cDNA copies corresponding to RNA. In some embodiments, the RNA includes one or more types of RNA, including, for example, mRNA, tRNA, rRNA, and snRNA. In some embodiments, the RNA comprises RNA transcripts.

Some embodiments use a primer that hybridizes to the target polynucleotide whose complementary strand is to be synthesized. In some of those embodiments, the primer used comprises a polyT region and optionally, a region of degenerate nucleotides. This facilitates identification and/or counting of random mRNA sequences in eukaryotic cells, as the polyT can hybridize to the polyA region of the mRNA and the degenerate nucleotides can hybridize to corresponding random sequences. Incorporation of degenerate nucleotides into seed primers also avoids sequencing the polyA tail itself while taking advantage of a universal seed primer for primer extension.

In some embodiments, the RNA comprises RNA molecules from a cell, from an organelle, and/or from a microorganism. The number of RNA molecules may be about 100, about 200, about 300, about 400, about 500, about 600, about 700, about 800, about 900, about 1,000, about 2,000, about 3,000, about 4,000, about 5000, about 6,000, about 7,000, about 8,000, about 9,000, about 10,000, up to an including all of the RNA molecules in the cell, organelle, and/or microorganism. Some embodiments comprise identifying/sequencing and/or counting RNA molecules from more than one cell, organelle, and/or microorganism. A histogram of the copy numbers of various types of RNA molecules identified can be constructed for different cells, organelles and/or microorganisms, and used to compile transcriptional patterns of RNA complements for each analyzed cell. The different cells, organelles, and/or microorganisms may be in different states, e.g. a diseased cell vs. a normal cell; or at different stages of development, e.g. a totipotent cell vs. a pluripotent cell vs. a differentiated cell; or subjected to different stimuli, e.g. a bacterial cell vs. a bacterial cell exposed to an antibiotic. In some embodiments, the methods can detect any statistically significant difference in copy numbers between cells, organelles, and/or microorganisms.

Annotating Genomes

The invention also features an approach to annotating genomes based on counting and identifying RNA transcripts. The identified transcripts indicate, for example, how sequenced genes are actually transcribed and/or expressed. By comparing the analyzed sequence of an identified transcript to one or more predicted expressed sequences, the prediction can be confirmed, modified, or refuted, providing a means to annotate genomes.

Determining Phylogenic Relationships

Still another feature of the present invention involves methods of determining phylogenic relationships of various species. Such embodiments provide for compiling transcriptional patterns of cells from different species and analyzing the relationships amongst homologous transcripts. Such information finds use in determining evolutionary relationships amongst species.

Determining Cellular Responses to Stimuli

Another feature of the present invention involves a method of determining a microorganism's response to various stimuli, for example, response when exposed to a drug or subjected to other treatment, such as being deprived of certain metabolites. In such embodiments, transcriptional patterns of a cell of the microorganism, for example a bacteria cell, can be compared before and after administration of the drug or other treatment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the present invention described herein may be employed in practicing the present invention. It is intended that the following claims define the scope of the present invention and that methods and structures within the scope of these claims and their equivalents be covered thereby.

EXAMPLES

Example 1: Controlled Extension

Figure 9:
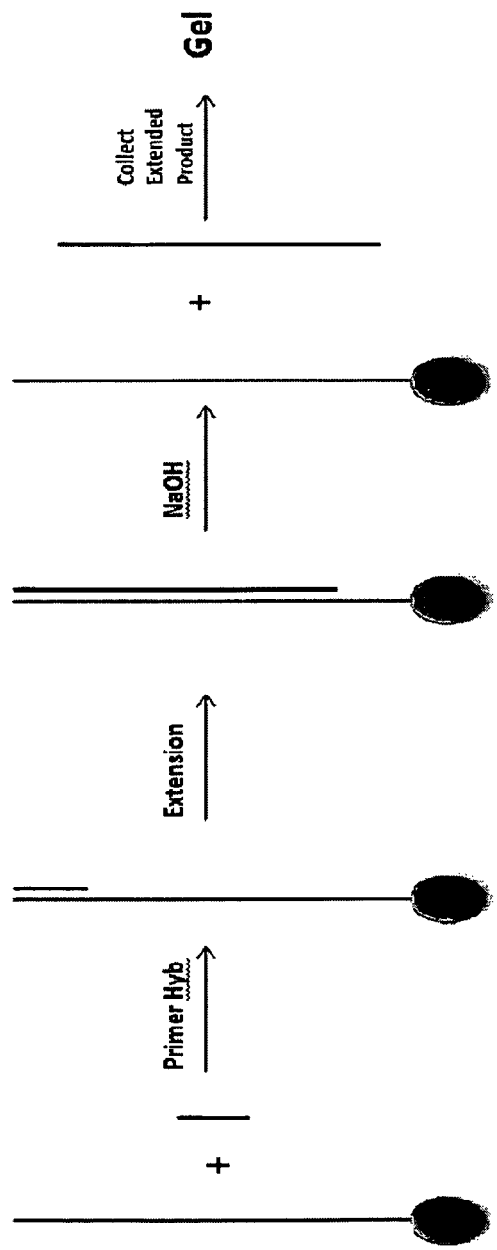
FIG. 9 depicts an exemplary embodiment of a dark base (native nucleotide) extension experiment design.

A sequencing template was immobilized on streptavidin coated beads via its 5' biotin and was hybridized with a sequencing primer by incubating at 70° C. for 3 min., 55° C. for 15 min and 25° C. for 5 min. In a 50 µl reaction, 8U Klenow exo(−), 65 mU of apyrase, 10 mU of inorganic pyrophosphatase, and 5 µg of single strand binding protein (SSB) were added. The extension reactions were carried out at room temperature. At one minute intervals, successive sets of nucleotides, each of 6.7 µM final concentration, were added to the reaction buffer with mixing. Three dark bases (native nucleotides) were added at each step as depicted in FIG. 8. After 5 step nucleotide additions as depicted in FIG. 8, the beads were washed and a fresh reaction buffer with enzymes and SSB was added to the beads. After some nucleotide addition steps, for example, after Steps 9, 10, and 12 as depicted in FIG. 8, in which the results are depicted in FIG. 3, an aliquot of beads was taken out and treated with NaOH to release the extended primer. The extension products were examined using denaturing polyacrylamide gel and the signals were analyzed using ImageJ (available from the National Institute of Heath). A general schematic of the protocol is depicted in FIG. 9.

Figure 10:
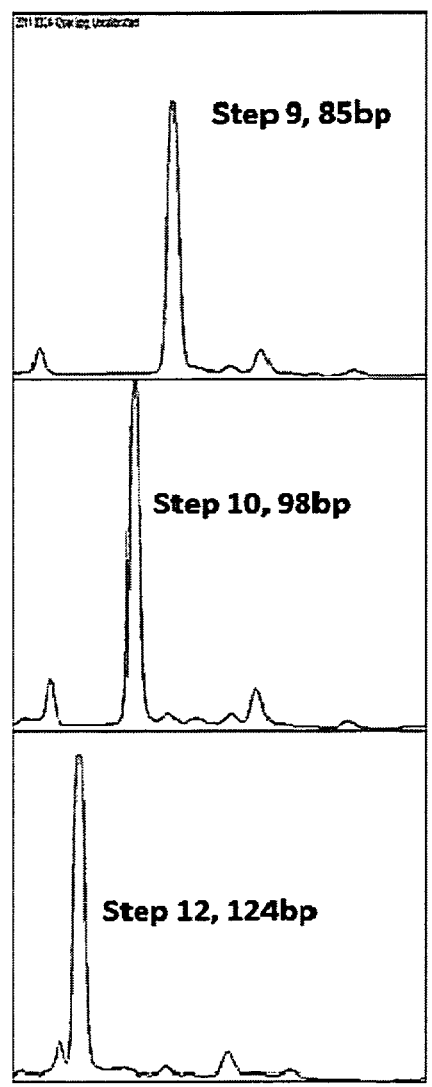
FIG. 10 depicts results of an exemplary embodiment of the present invention, in which 12 steps of 3-base extension resulted in a 124 base pair (bp) product (extension plus primer), wherein the template was an oligonucleotide.

The results of the extension products are depicted in FIG. 10. The largest band is the expected extension product. The primary product of the extension was as expected in length. Few smaller bands were detected, which may be products of incomplete incorporation and represented a small portion of the reaction products. The Step 9 extension product of 85 base pairs (bp), which corresponds to the extension of 63 bp to the 22 bp primer, the Step 10 extension product of 98 bp, which corresponds to the extension of 76 bp to the 22 bp primer, and the Step 12 extension product of 124 bp, which corresponds to the extension of 102 bp to the 22 bp primer, are depicted in FIG. 11.

Example 2: Controlled Extension with PCR Product as Template

A PCR product was used as a template in this Example. The PCR template was immobilized on streptavidin coated beads via its 5' biotin and was hybridized with a sequencing primer by incubating at 70° C. for 3 min., 55° C. for 15 min and 25° C. for 5 min. In a 50 µl reaction, 8U Klenow exo(−), 65 mU of apyrase, 10 mU of inorganic pyrophosphatase, and 5 µg of single strand binding protein (SSB) were added. The extension reactions were carried out at room temperature. At one minute intervals, successive sets of nucleotides, each at 6.7 µM final concentration, were added to the reaction buffer with mixing. Three dark bases were added at each step as depicted in FIG. 8.

Figure 11:
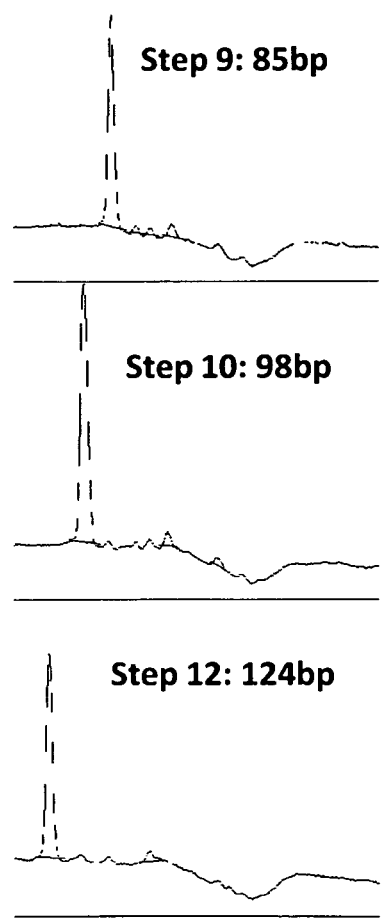
FIG. 11 depicts results of an exemplary embodiment of the present invention, in which 12 steps of 3-base extension resulted in a 124 bp product (extension plus primer), wherein the template was a PCR product.

The results of the extension products are depicted in FIG. 11. The largest band is the extension product. The primary product of the extension was as expected in length. Few smaller bands were detected, which may be products of incomplete incorporation and represented small portion of the reaction products.

The Step 9 extension product of 85 base pairs (bp), which corresponds to the extension by 63 bp of the 22 bp primer, the Step 10 extension product of 98 bp, which corresponds to the extension by 76 bp of the 22 bp primer, and the Step 12 extension product of 124 bp, which corresponds to the extension by 102 bp of the 22 bp primer, are depicted in FIG. 11.

Example 3: Massive Parallel Sequencing Following Dark Base Extension

Massive parallel sequencing following dark base +S extension was demonstrated using a sequencing flow cell with 8 lanes (commercially available from Illumina, San Diego, Calif.). Sequencing libraries prepared from genomic samples (including samples enriched for exon regions) were prepared and sequenced for 100 bases according to standard protocols using an Illumina HiScanSQ sequencer.

All flow cell lanes were then stripped with 0.1N NaOH to remove sequencing extension products that are labeled with fluorescent signals. The resulting flow cell lanes were washed with saline-sodium citrate (SSC) washing solution. A sequencing primer (P1) was hybridized with sequencing templates still in the flow cell lanes for 30 minutes at 60° C. The flow cell lanes/channels were then washed with SSC.

For Lane 1, pre-incubation buffer with Klenow, NEB2, pyrophosphatase was loaded and kept for 1 minute. A dark base (+S) triplet solution with 13.4 µM each of dTTP, dGTP, and dCTP in buffer was loaded for one minute, then removed. An apyrase wash solution (1 mU/µl) was loaded into the lane and removed after three minutes. Another cycle of dark base extension was then employed. The sequence of dark base extension in terms of missing nucleotides was A, T, G, C, A, T, G, C, A, and T. A total of ten dark base extension steps were used, with the last missing nucleotide being dTTP.

For Lane 3, pre-incubation buffer with Klenow, NEB2, pyrophosphatase and apyrase (1 mU/µl) was loaded and kept for 1 minute. A dark base triplet solution is spiked into the pre-incubation solution with 13.4 µM each of dTTP, dGTP, and dCTP. The mixed solution was loaded into the flow cell lane for one minute. Another cycle of dark base addition/extension was then employed. The sequence of dark base extension in terms of missing nucleotides was A, T, G, and C. A total of four dark base extension steps were used, with the last missing nucleotide being dCTP.

After dark base extension, the flow cell was then loaded to an Illumina HiScanSQ sequencer to sequence 25 bases (second sequencing). After the second sequencing, the flow cell lanes were striped again with 0.1 N NaOH and the striped nucleic acids were analyzed using a denaturing gel.

Lane 1 generated about 278 million base reads with about 11 million clusters passing filter. Lane 3 generated about 653 million base reads with about 25.6 million clusters passing filter.

Figure 12:
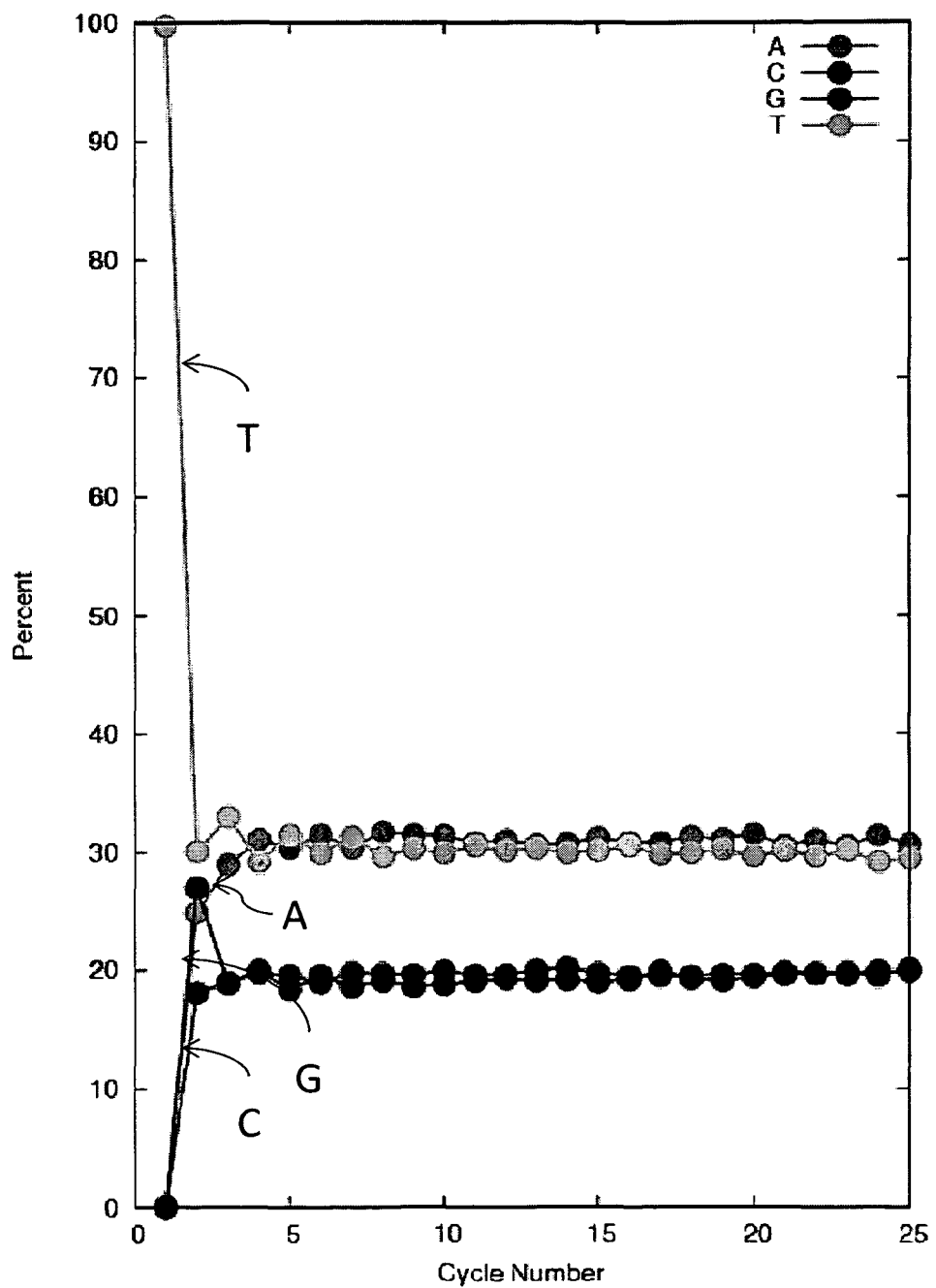
FIG. 12 depicts the percent base calls per sequencing step for lane 1 of an exemplary embodiment of the present invention, where the last step of the dark base extension was a missing T step, and as expected, 100% of the first sequencing base was "T".

FIG. 12 shows the percent base calls per sequencing step for Lane 1. As expected, 100% of the first base was called "T" as the last step of the dark base extension was a "missing T" step, as it is expected that the first base addition in the sequencer after the first base should be "T".

Figure 13:
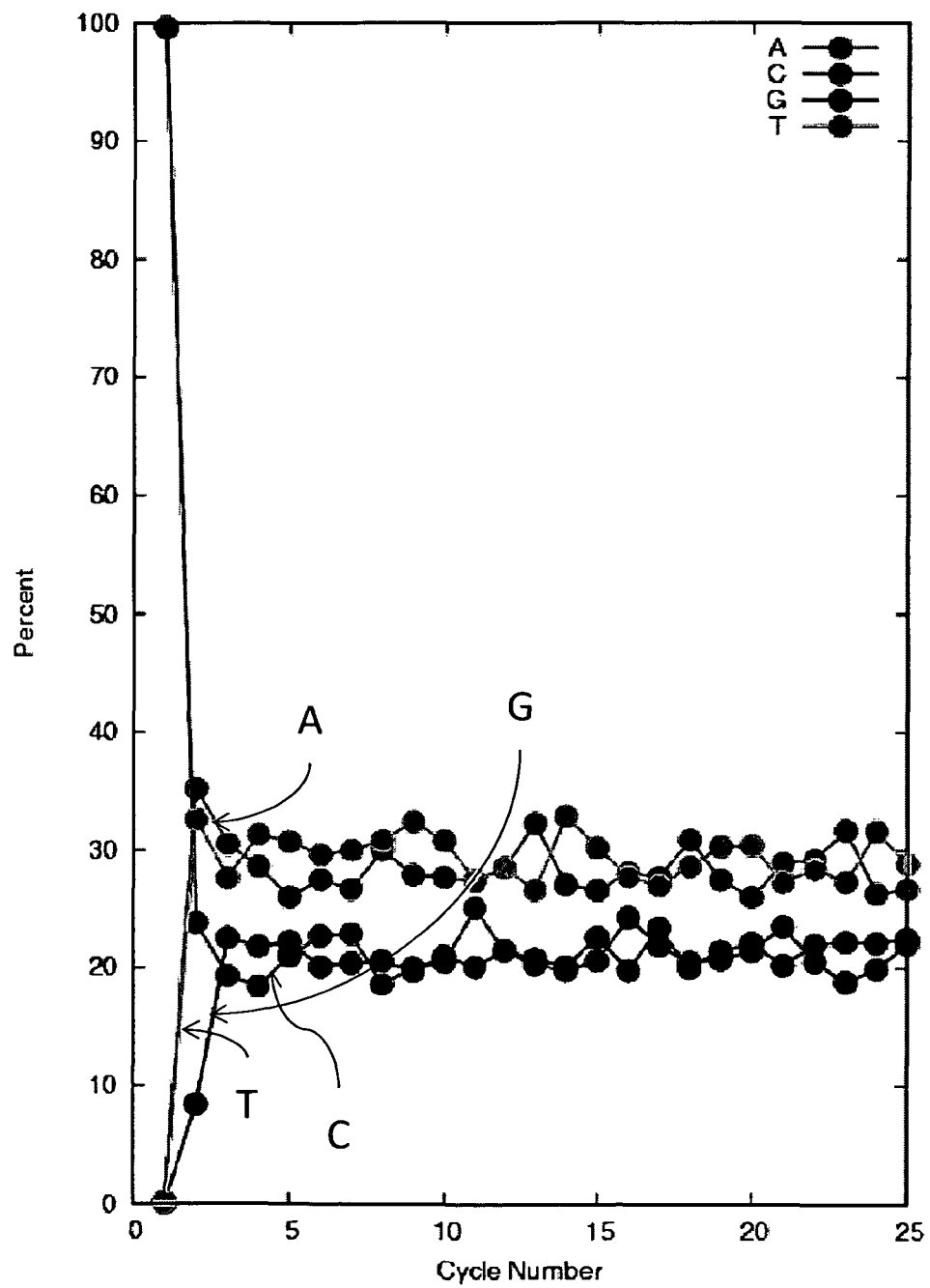
FIG. 13 depicts the percent base calls per sequencing step for lane 3 of an exemplary embodiment of the present invention, where the last step of the dark base extension was a missing C step, and as expected, 100% of the first sequencing base was "C".

FIG. 13 shows the percent base calls per sequencing step for Lane 3. Also as expected, 100% of the first base called was "C."

The sequences from the seconding sequencing were matched with the sequences from the first sequencing as the templates were the same. Because there were alignment changes between the first and second sequencings (flow cell was removed from the sequencer for dark base extension), a search algorithm was used to match the sequences with a range of 150 units of x, y coordinates from the Illumina qseq files. One million passed filter sequences from lane one, second sequencing (25 bases long) were checked and 71.3% of the sequences matched part of the sequences from seconding sequencing (100 bases long). Similarly, one million passed filter sequences from lane three, second sequencing (25 base long) were checked and 76.56% of the sequences matched part of the sequences from second sequencing (100 bases long).

Figure 14:
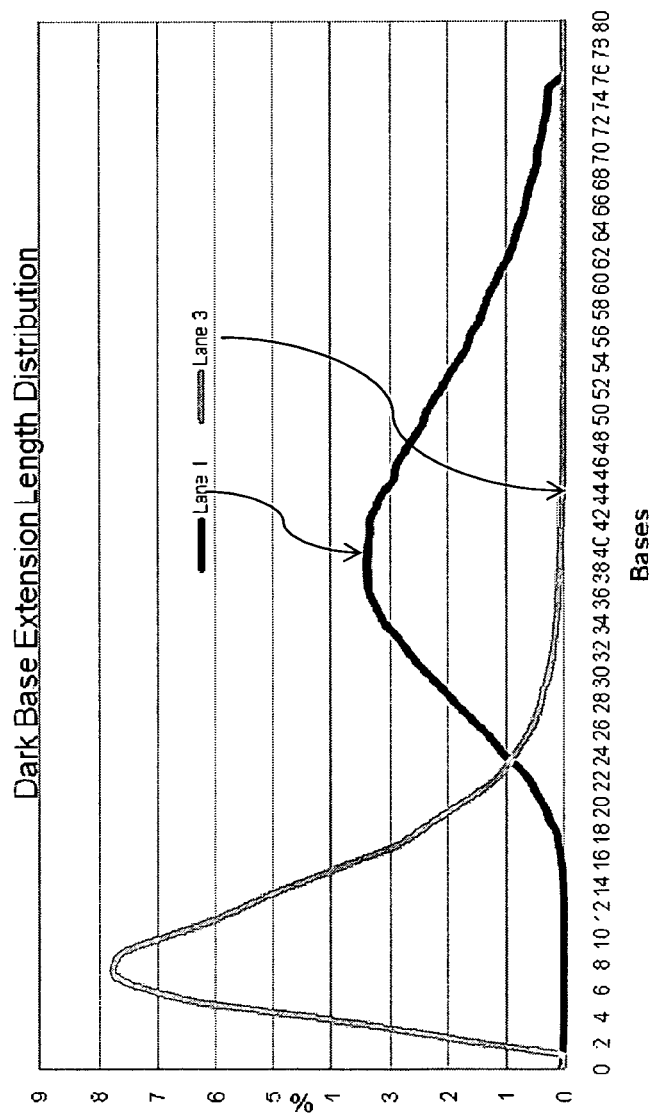
FIG. 14 depicts the distribution of dark base extensions in lane 1 (10 steps) and lane 3 (4 steps).

The sequence match positions were also analyzed. FIG. 14 shows that the distribution of dark base extensions in Lane 1 (10 steps) and Lane 3 (4 steps). These distributions agree with the expected distribution. Both the high exact sequence match and the correct distribution indicate that the sequence after dark extension worked reasonably well.

When 8.8 million sequences from Lane 1 were checked to examine whether the actual dark extension match with expectations according to the sequences from sequence 1, 98.2% of the dark base extension was found as expected. Among the 8.8 million sequences, 8.7 million sequences matched with the 10 step (ATGC cycle) dark base extension. An additional 5,673 sequences from second sequencing did not have first base calls. Assuming that the first base was "T" as expected for these sequences, they matched with the 10 step dark base extension.

Example 4: Massively Parallel Sequencing Following Controlled Extension

Massively parallel sequencing following controlled extension was again demonstrated using an Illumina HiScanSQ sequencer. Eight genomic samples enriched for exon regions were used to prepare Illumina pair end sequencing library and sequenced for 75 bases per end (2×75 bases) according to a standard protocol based on Agilent and Illumina reagents and protocols. After the second end sequencing (read 2), lanes 1-6 and 8 were used for controlled extension using a cBot cluster generation system (Illumina), custom programmed by Centrillion Biosciences, Inc. to perform controlled extension with a custom assembled reagent kit.

The cBot cluster generation system was reprogrammed to utilize a custom edited protocol to deliver nucleotide combinations at specified time intervals, as well as other reagents. After all lanes were stripped with 0.1N NaOH (120 µl) to remove sequencing extension products, an Illumina sequencing primer (SP2, 95 µL) was introduced into all lanes to hybridize to clusters of ssDNA template on the surface of the flow cell. Hybridization was performed for 15 min at 60° C., followed by slow cooling to 20° C. at a rate of 3° C./min.

Controlled extension was accomplished by repeated introduction of unlabeled native nucleotide triplets (85 µL for 1 minute), followed by apyrase containing washing solution (120 µL for 2 minutes). Finally, a wash solution of NEB2 (120 µl, 1×) was pumped through the flow cell before proceeding to the following dark base extension step. For example, Lane 4—(10 steps), nucleotide combinations were: —missing A, C, G, T, A, C, G, T, A, C; Lane 5—(16 steps)—missing A, C, G, T, A, C, G, T, A, C, A, C, G, T, A, C; Lane 6—(20 steps)—missing A, C, G, T, A, C, G, T, A, C, A, C, G, T, A, C, G, T, A, C; and Lane 7—(0 steps)—control, sequencing primer only (no dark base extension).

After dark base extension, the flow cell was loaded to an Illumina HiScanSQ sequencer to sequence 75 bases (second sequencing).

Lane 4 generated about 1,927 million base reads with about 25.7 million clusters passing filter. Lane 5 generated about 1,324 million base reads with about 17.6 million clusters passing filter. Lane 6 generated about 884 million base reads with about 11.8 million clusters passing filter.

The sequences from the second sequencing were matched with the sequences from the second read of the first sequencing. Because the second sequencing was extended longer than the second read of the first sequencing, the sequences from the second sequencing may or may not overlap with the sequences from the second read of the first sequencing from the same cluster. The sequences from both sequencing runs were mapped to the human genome and a search algorithm was used to compare the mapping position on human chromosomes to determine if two sequences were from the same cluster based on their mapping positions. Because there were cluster alignment changes between the first and second sequencings (flow cell was removed from the sequencer for dark base extension), the search algorithm considered to match the sequences with a range of 600 units of x, y coordinates from the Illumina qseq files.

One million passed filter sequences from lane 4, second sequencing (75 bases long) were checked and 80.4% of the sequences mapped to the positions next to where the sequences from first sequencing (75 bases long) were mapped. Similarly, one million passed filter sequences from lane 5, second sequencing (75 base long) were checked and 81.8% of the sequences mapped to the positions next to where the sequences from first sequencing (75 bases long) were mapped. Similarly, one million passed filter sequences from lane 6, second sequencing (75 base long) were checked and 82% of the sequences mapped to the positions next to where the sequences from first sequencing (75 bases long) were mapped.

Figure 15:
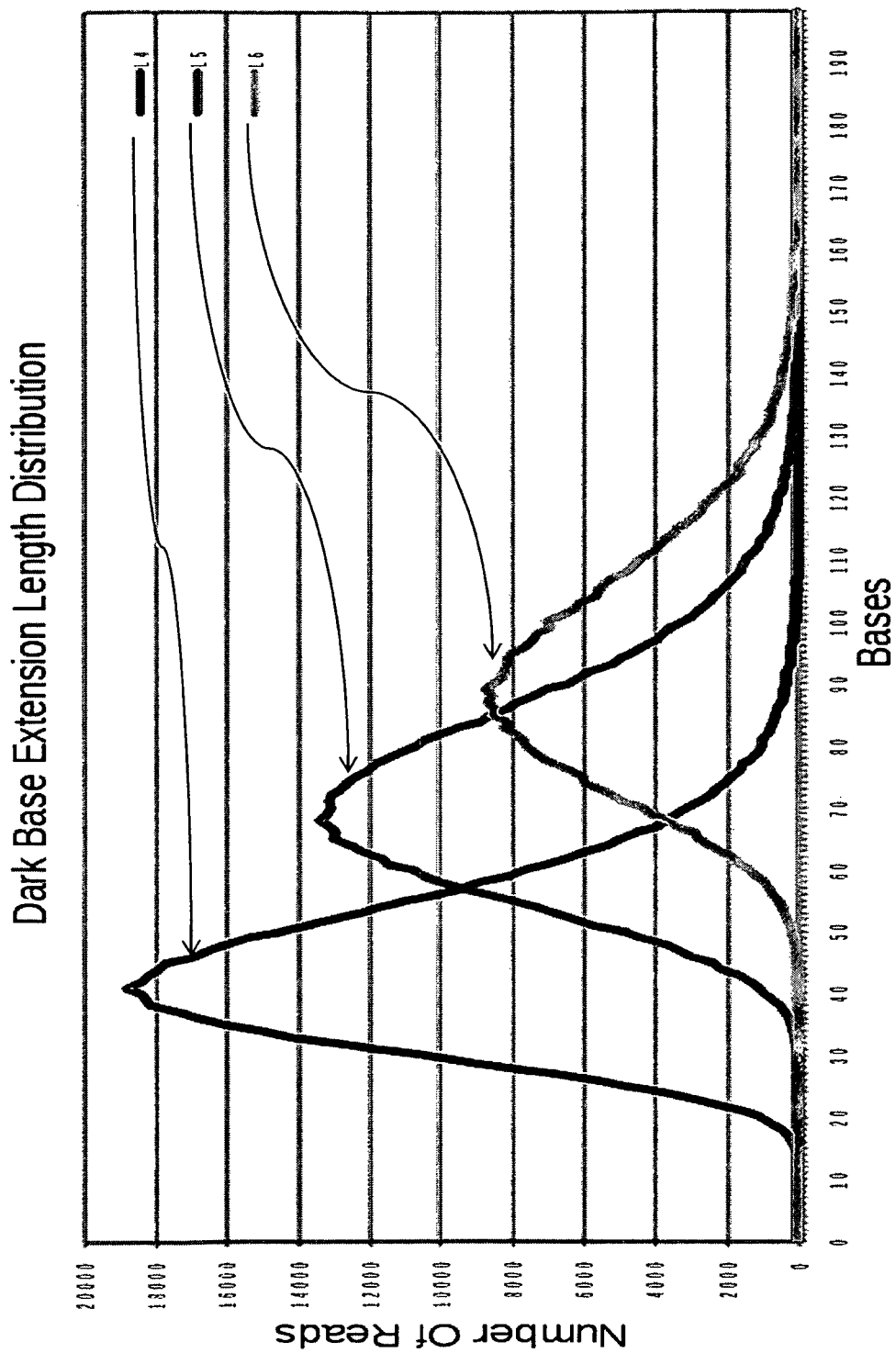
FIG. 15 depicts the distribution of dark base extensions in lane 4 (10 steps), lane 5 (16 steps) and lane 6 (20 steps) in another exemplary embodiment of the present invention.

The sequence match positions were also analyzed. FIG. 15 shows that the distribution of dark base extensions in Lane 4 (10 steps), Lane 5 (16 steps) and Lane 6 (20 steps). These distributions agree with the expected distribution. Both the high sequence mapping position match and the correct distribution indicate that the sequencing after dark extension worked reasonably well.

Example 5: Sequencing of Human and *E. Coli* DNA Samples

Introduction

Complete genome sequencing offers a truly unbiased view of the genome. It allows the entire genetic code of an individual to be deduced all at once and reveals comprehensive genetic information in personal health care. For a rare genetic disease for which the underlying mutation is currently unknown, whole-genome sequencing may be the only feasible way to identify the causative variant. However, the high cost of whole genome sequencing still prohibits routine genetic screens in large populations of individuals.

Next-generation sequencing (NGS) technologies represent major improvements in accuracy, read-length and cost. DNA sequencing-by-synthesis (SBS) technologies using a polymerase (Illumina, 454, Ion Torrent), and a ligase enzyme (Solid) have already been incorporated in several commercially available NGS platforms with significant success. Although the platforms differ in their engineering configurations and sequencing chemistries, they share a technical paradigm in that bases have been read sequentially, through iterative cycles of polymerase-mediated fluorescent-labeled nucleotide extensions or through successive fluorescent-labeled oligonucleotide ligation. Since fluorescently-labeled nucleotides are not native substrates of the polymerase, it is difficult for the reaction to achieve 100% completion. The cumulative effect of incomplete extensions at each step lead to dephasing that ultimately contributes to significant decreases in signal intensity in long reads. In addition, incomplete removal of terminating groups on labeled nucleotides can lead to further signal loss. In order to optimize the enzyme-substrate system current NGS platforms extensively rely on expensive proprietary enzymes, along with fluorescent nucleotides, optics, and instrumentation.

These fundamental system requirements limit current platforms ability to increase read length while maintaining high read quality. +S™ technology, an implementation of some embodiments described above, overcomes this hurdle by resetting the sequencing chemistry using length-controlled extension. Consequently, regions of DNA template farther away from the sequencing primer could be reached via +S, effectively increasing the read length without the signal loss and quality reduction inherent in current NGS platforms. This example demonstrates that +S™ technology that employs controlled extension in addition to sequencing greatly improves sequencing quality for long reads.

Materials and Methods

Library Preparation:

Human DNA samples and *E. Coli* (strain ATCC 11303) DNA sample were sheared using a Covaris protocol (Covaris, Inc., Woburn, Mass., USA) to desired length distribution. Resulting fragmented Human DNA samples were processed according to Agilent Sure Select™ Exome Protocols to prepare human exome libraries for sequencing. The resulting fragmented *E. Coli* DNA was further separated using 2% Agarose gel and a band ranging 600 to 700 bp was excised. After DNA extraction, the sample was processed according to Illumina TruSeq DNA Sample Preparation Guide to generate libraries for sequencing.

Standard Illumina Cluster Generation and Pair-End Sequencing:

Human Exome and *E. Coli* libraries were quantified by qPCR, diluted to proper concentration and denatured with 0.1 N NaOH according to Illumina TruSeq cBot procedure. Denatured human libraries and the 1% *E. Coli* Library were loaded into the cBot along with TruSeq PE Cluster v3 plate and a v3 Flow Cell. After completion of the cluster generation, the flow cell was loaded into HiScanSQ sequencer along with TruSeq SBS Kit v3 and multiplexing reagents. The sequencing run was executed using 2×100 TruSeq v3 Paired-End protocol and fully completed before any +S related steps were performed.

Flow Cell Preparation for +S:

After the completion of the second 100 bp read of standard Illumina pair-end sequencing lane 1 was immediately protected, and did not go through further processing (no +S steps). This lane preserved the conditions at the end of the second read, and would serve as a control representing continuation of Illumina sequencing beyond the 100 bp length.

On the other hand, lane 2 and lane 3 of the flow cell were treated with 0.1 N NaOH (200 µL) to remove the synthesized strands which are not attached to the flow cell (i.e. the second 100 bp read). Thus, only single stranded template molecules attached to the flow cell remained.

A sequencing primer mix was prepared by adding Illumina multiplex read2 sequencing primer (PN 1005721) to a final concentration of 0.5 µM in hybridization mix (5×SSC, 0.05% Tween-20). Lanes 2 and 3 were hybridized with the sequence primer mix according to standard Illumina cBot protocol. At this point lane 2 was also protected until further sequencing.

+S Extension:

Lane 3 underwent the +S Extension method. In total, twenty four cycles of three base +S Extensions were performed on lane 3 at 37° C. Three nucleotides (a triplet format) were added at each addition step together (forming a cycle). For clarity, we named the addition of tri-nucleotides as "minus the fourth nucleotide mix". Therefore, -A mix consists of (dC, dG, dT); -C mix contains (dA, dG, dT); -G mix contains (dA, dC, dT); and finally, -T is the addition of (dA, dC, dG). During the +S Extension, the sequence of cycles of tri-nucleotides (triplets) was "-A, -C, -G, -T, -A, -C, -G, -T, -A, -C, -G, -T, -A, —C, -G, -T, -A, -C, -G, -T, -A, -C, -G, -T", for a total of 24 cycles. +S Extension mix included: 1× Thermopol buffer (NEB), 0.5 M GC-Melt (Clonetech), 4 mM DTT (Sigma), 1 mg/ml BSA (NEB), 0.2 mg/ml PVP-10 (Sigma), 0.8 µg/ul SSB (Epicentre), 2 mU/µl Pyrophosphatase (NEB) and 1.6 U/µl Bst Polymerase (NEB).

Appropriate nucleotide combinations were added to the +S extension mix to a final concentration of 5 µM (each nucleotide washing solution was prepared with 1× Thermopol, 4 mM DTT and 1 mU/ul apyrase (NEB)).

Prior to +S Extension, lane 3 was filled with 85 µl of the +S extension mix without nucleotides and then incubated for 30 seconds. The +S extension cycle was performed by pumping +S extension mix with nucleotides (35 µl), followed by 3 µl of air at a rate of 60 µl/min. Consequently, wash mix (120 µl) was pumped and incubated for 1 minute, followed by 1× Thermopol wash (120 µl). This order of reagent pumping was repeated for 24 cycles with the designated nucleotide triplet combination in each cycle (i.e. -A, -C, etc.). Finally, after +S Extension, lane 3 was loaded with holding buffer and protected until further sequencing.

Re-Run of Standard Illumina Sequencing (Single-Read):

With all the lanes (1, 2, 3) prepared, the flow cell was loaded into HiScanSQ sequencer along with TruSeq SBS Kit v3. In order to focus effectively with HisScanSQ after S+ process, 1 cycle of TruSequ v3 was performed for all the lanes (1, 2, 3). The new sequencing run was executed using single read 1×100 TruSeq v3 protocol as if starting from a new flow cell. In effect, this new single read 1×100 run is re-sequencing the 2nd read of the pair-end protocol that was completed earlier, where lane 1 is reading base positions 102-201 as a continuation of the previous run, lane 2 is re-reading bases 2-101 since it starts with only the sequencing primer, while lane 3 starts at a range of positions due to +S Extension. More precisely, the 24 cycles of +S Extension in lane 3 resulted in sequencing primers being extended by an average of 96 bp.

Data Analysis:

E. Coli sequencing reads were aligned to the assembled E. Coli genome (strain ATCC 11303) using sequence alignment tool BWA. The genome of E. Coli strain ATCC 11303 was assembled using sequencing reads of the same strain from a standard Illumina sequencing run. Only uniquely aligned reads were used in the quality calculation. In one quality calculation, all bases of each uniquely aligned read were counted regardless of the quality value. For an individual read, bases at each position were recorded as correct or wrong based on the comparison to the reference E. Coli genome, then the Phred-style quality score Q at each base position was calculated as the negative logarithm of error rate E at the base position:

$$Q = -10 * \log 10 E$$

where E=(number of bases recorded as wrong)/(number of bases recorded as correct+number of based recorded as wrong)

Sequencing quality was also measured using Genome Analysis Tool Kit (GATK, www.broadinstitute.org/gsa/wiki/index.php/The_Genome_Analysis_Toolkit). First, all sequence reads were aligned to the assembled E. Coli genome (strain ATCC 11303) using sequence alignment tool BWA. The CountCovariates module of GATK was then used to calculate the quality. In this calculation, continuous low quality bases (bases with raw Illumina quality score of 2) at the end of each read were dropped before the average quality was calculated.

Figure 16:
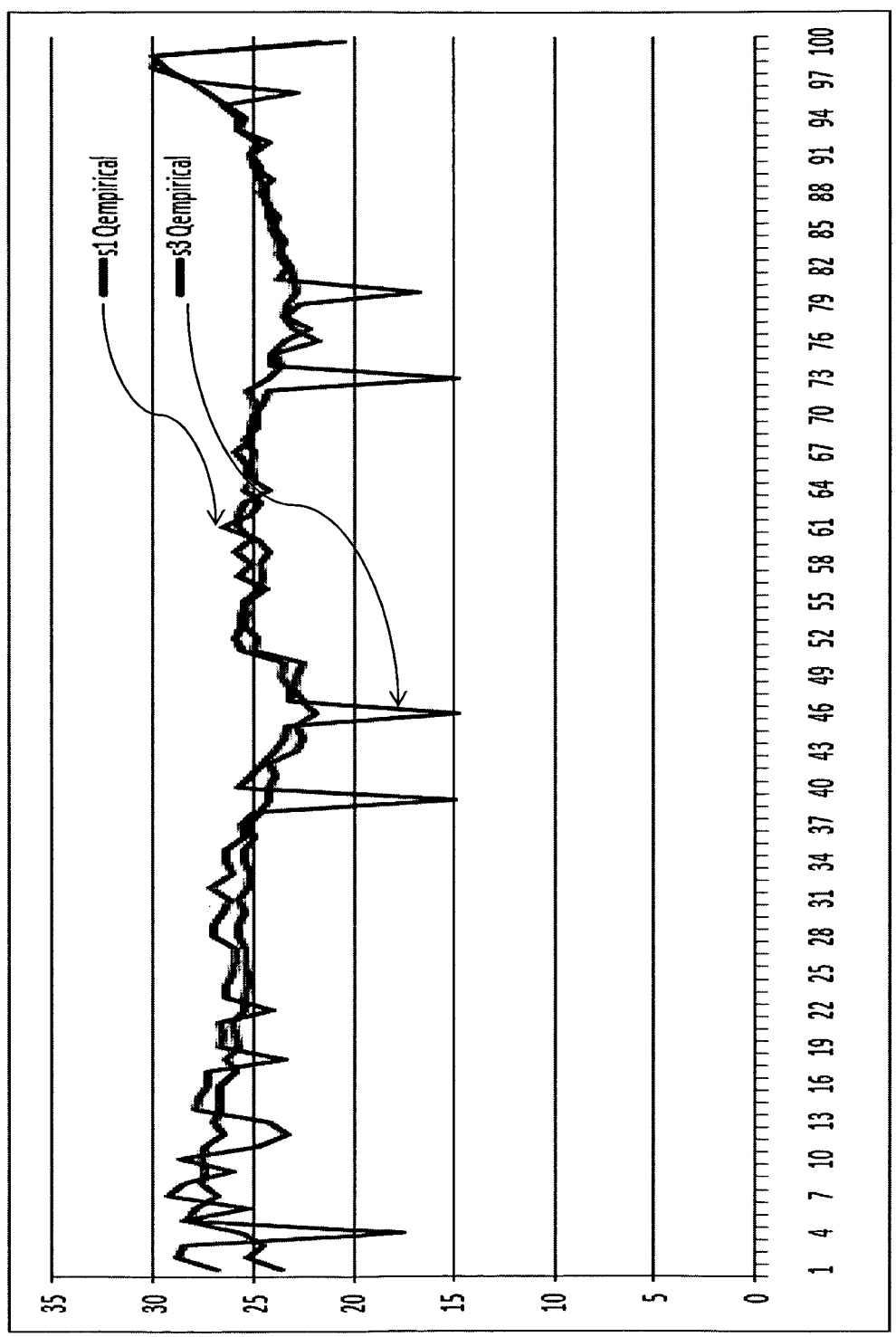
FIG. 16. is a summary of results for sequencing in Example 5.
Figure 16:
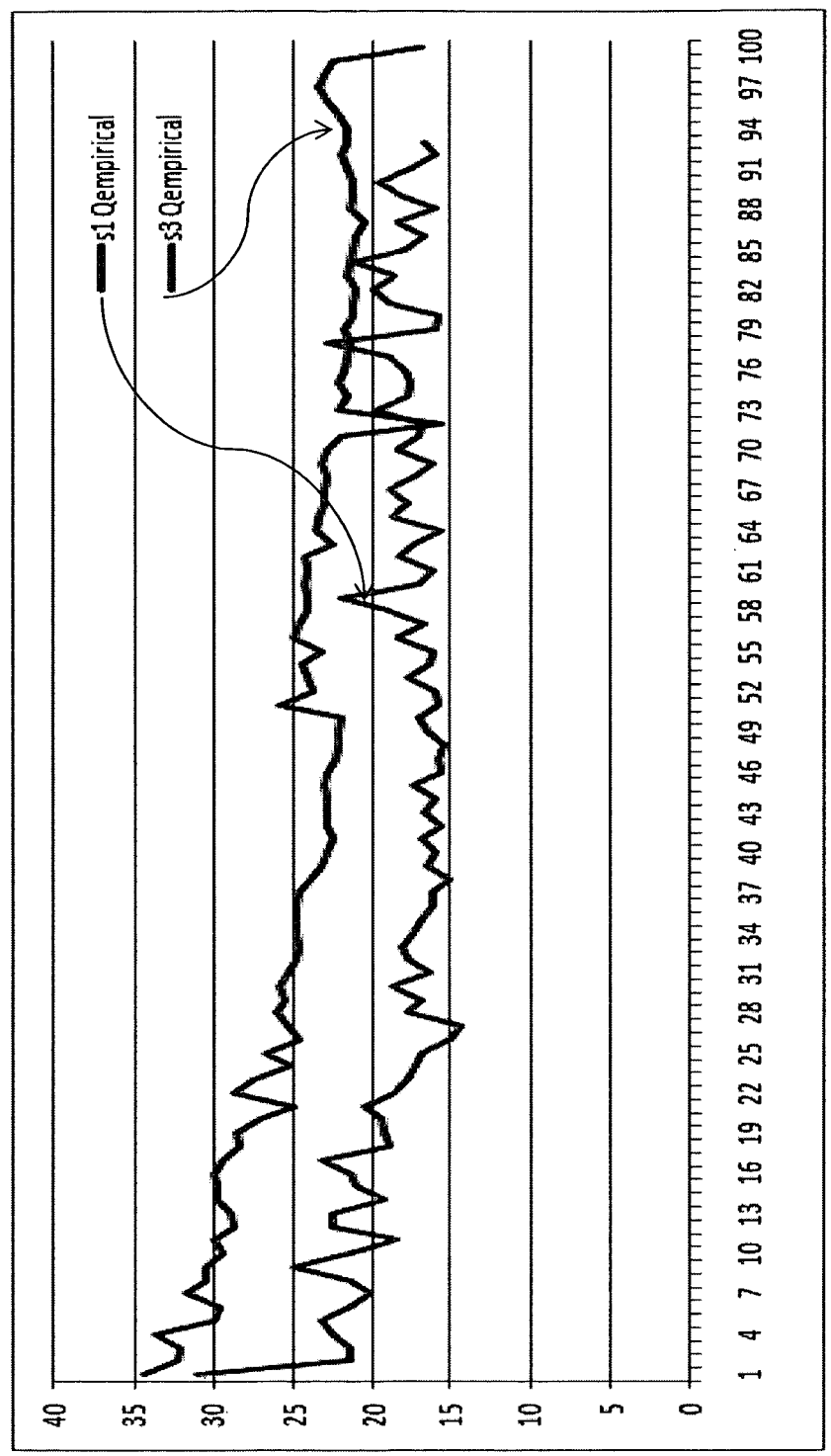
Figure 16:
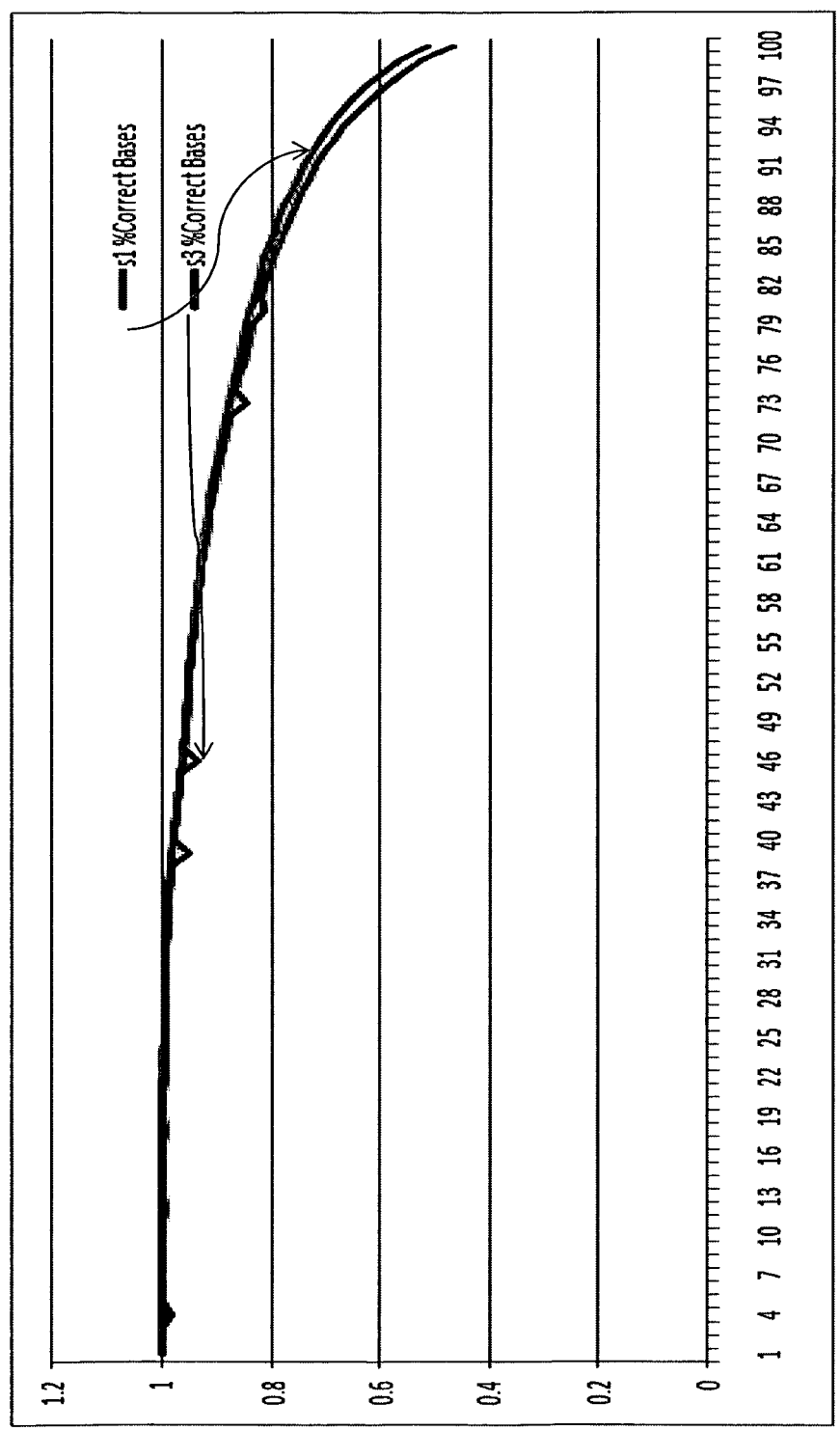
Figure 16:
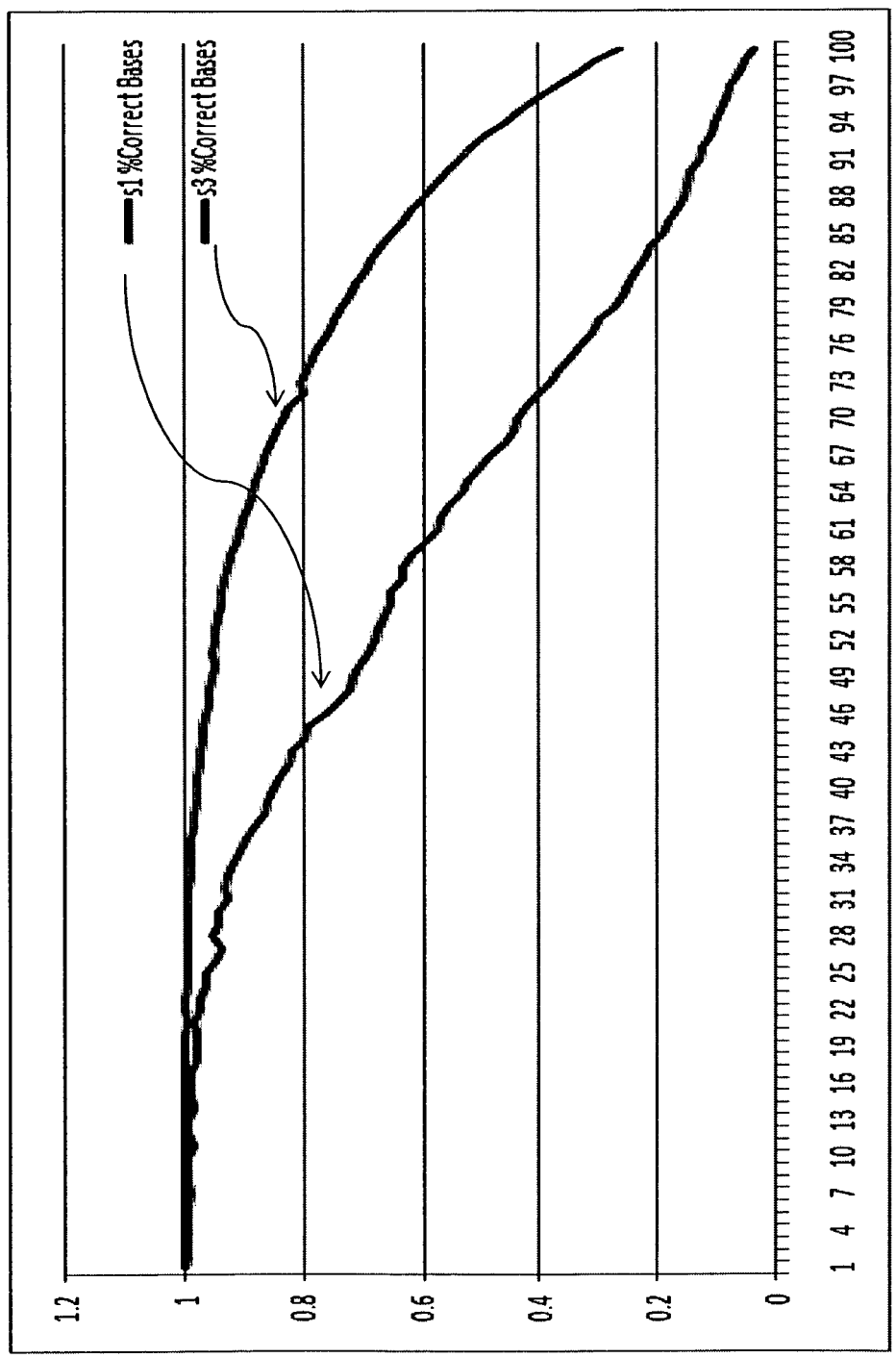

In FIG. 16, Q-Scores for bases 1 to 100 were taken from the sequencing reads using standard Illumina protocol for lane 1 (S1) and lane 3 (S3), (i.e. the 2nd read of 2×100 pair-end protocol). For lane 1, bases 101 to 200 Q-Scores were obtained from the continuation sequencing run using standard Illumina protocol (1×100) without +S extension. For lane 3, 24 steps of +S Extension were introduced before reads were sequenced using standard Illumina sequencing protocol (1×100), which provided the Q-Scores for lane 3.

Results

+S Technology on Illumina Sequencing Platform

This example demonstrates +S technology's ability to increase read length while maintaining read quality using Illumina's HiScanSQ sequencer. After 24-cycle +S extension on lane 3, the standard sequencing primer is extended on average about 100 bp before running the 1×100 Illumina Sequencing (see Methods and Materials). The +S Extension in lane 3 is similar in length to the lane 1 condition, which contains the 100 bp read of the original Illumina's SBS. Therefore, the single read 1×100 Illumina Sequencing is reading positions 101-200 in both lanes 1 and 3, with the difference that lane 1 is continuation of earlier Illumina sequencing, while lane 3 contains freshly made +S Extension of average length of 100 bp In this way, the two lanes could be compared side-by-side to evaluate the effectiveness of +S Extension in increasing read length while maintaining read quality. Finally, Lane 2 is the control lane for sequencing primer hybridization, cluster retention and flow-cell performance.

FIG. 16A compares the cluster density of different lanes after +S Extension on lane 3. Lane 1 is protected throughout +S process. Lane 2 was treated with NaOH and subsequently re-hybridized with sequencing primer together with Lane 3. Neither lanes 1 nor 2 were extended with +S. The similar cluster density in lanes 2 and 3 indicate good cluster retention after +S. Lane 1 (continuing sequencing 101-200 bases) has a lower cluster density, which is probably the result of dephasing in standard Illumina sequencing. Clearly, at approximately similar sequencing length, Lane 3 (+S) has a higher density than Lane 1 (standard Illumina sequencing).

FIG. 16B shows % cluster pass filter rate. After restarting the sequencer, only 10% of clusters passed filter on lane 1. In contrast, 70% of clusters passed filter on lane 3.

FIG. 16C shows the number of pass filter reads for different lanes. Lane 3 (+S) has a much higher pass filter rate than lane 1 and is only slightly lower than lane 2, which was sequencing the bases from 1 to 100 vs. lane 3's sequencing which sequenced on average positions 101 to 200. Similarly, the predicted quality scores of different lanes (FIG. 16D) show similar pattern, where +S sequencing dramatically improved the number of Q30 or above reads vs. lane 1.

We also performed +S Extension then standard Illumina sequencing on another lane (lane 8). The results of lane 8 show similar patterns to those of lane 3 (data not shown here).

Figure 17:
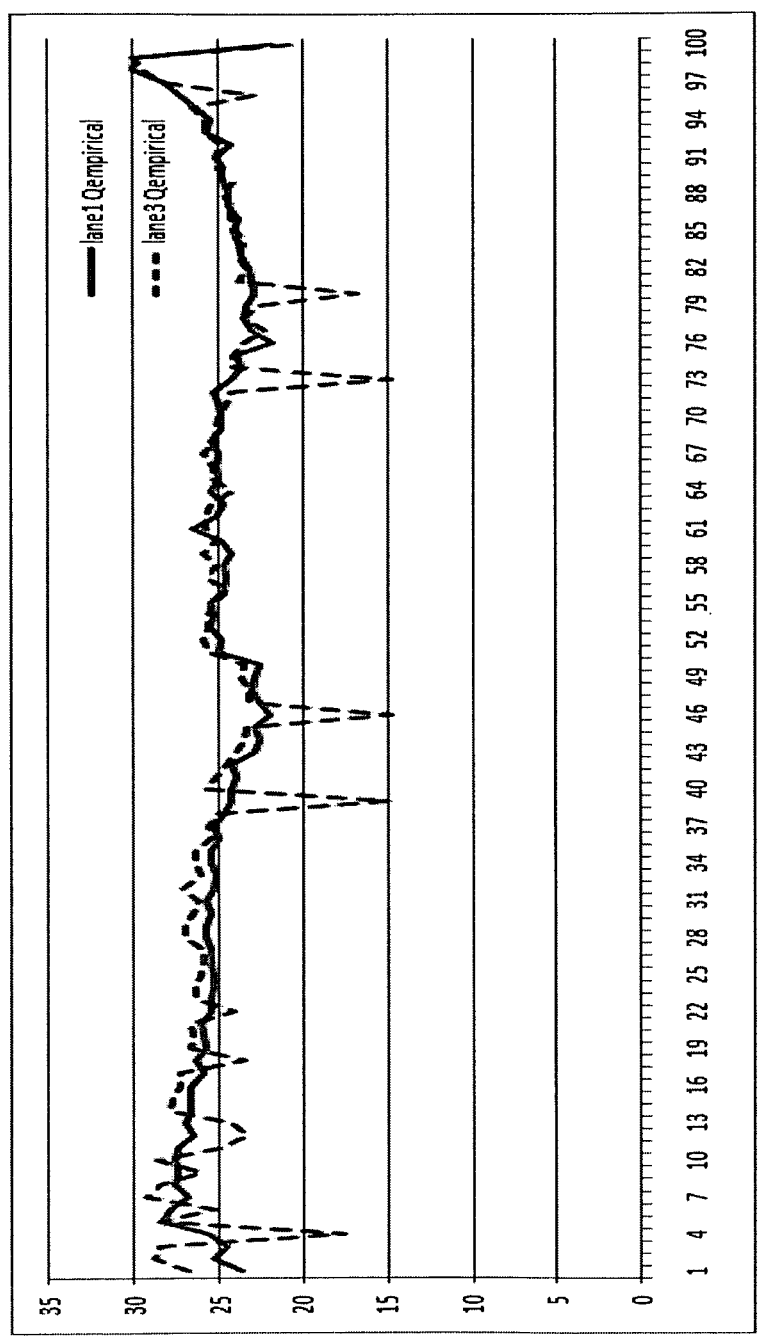
FIG. 17 shows quality score changes over read length.
Figure 17:
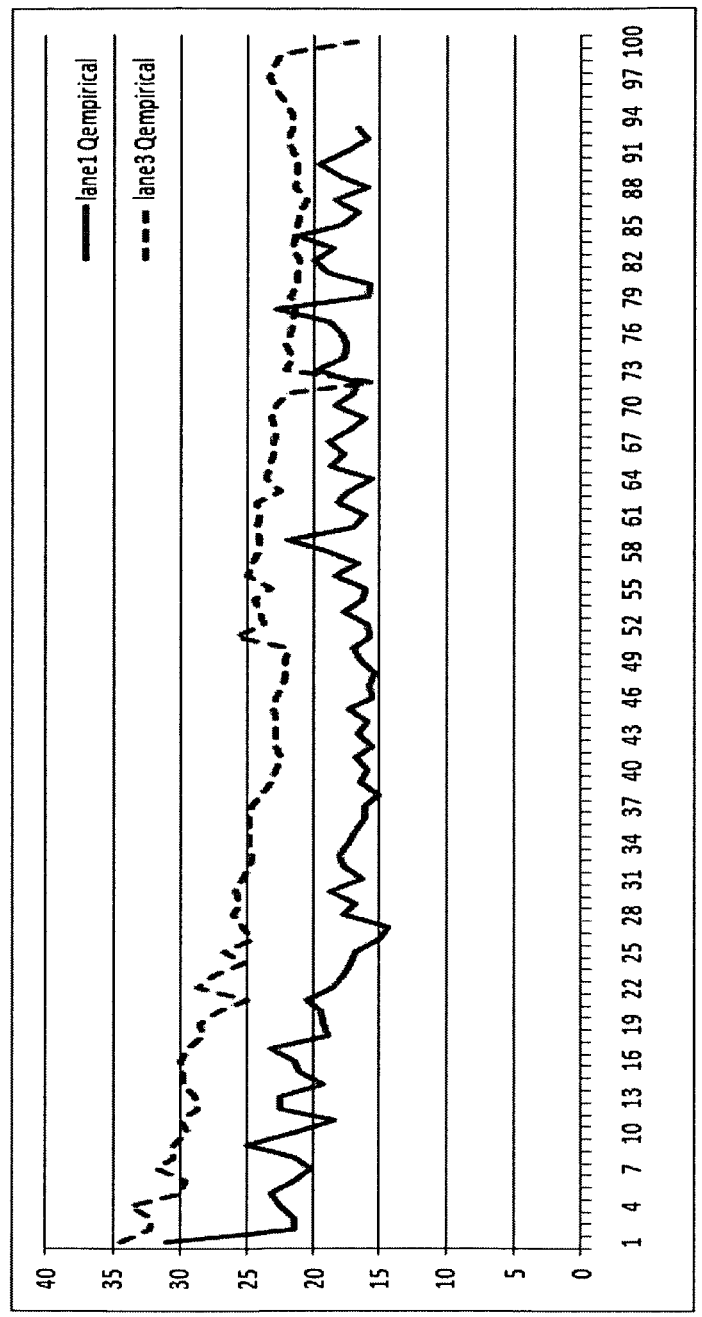

FIGS. 17A and 17B show the empirical (actual Q-Score distribution over read length) Q-Score calculated using GATK. FIG. 17A shows the 100 bp standard Illumina sequencing run. FIG. 17B shows the additional 100 bp Illumina sequencing run, which was after the 100 bp sequencing run shown in FIG. 17A and an extra 1 bp sequencing run. For lane 1, x-axis position 1 to 100 in FIG. 17A was the actual base position 1 to 100 on each DNA fragment sequenced; x-axis position 1 to 100 in FIG. 17B was actual base position 102 to 201 on each DNA fragment sequenced. For lane 3, x-axis position 1 to 100 in FIG. 17A was the actual base position on each DNA fragment sequenced; the actual base position on each DNA fragment for x-axis position 1 to 100 in FIG. 17B would depend on the actual +S extension size of each individual DNA fragment. Based on the +S extension size distribution, the average extension size on lane 3 is 97 bases. Therefore, the average of actual base position on DNA fragment for x-axis position 1 to 100 in FIG. 17B is 98 (97 plus 1 from additional 1 bp sequencing run) to 197. Because very few bases were available for lane 1 after x-axis position 94 in FIG. 17B, the empirical quality score was not calculated for lane 1 after x-axis position 94 in FIG. 17B. Clearly, even with the low quality bases at the end of reads had been dropped, the quality of actual base positions 102 to 193 of Illumina continuation sequencing (lane 1) was much worse than +S sequencing (lane 3). The several sudden dips in lane 3 Q-Scores were due to the bubbles in the flow cell which prevented proper imaging of the clusters at those base positions.

Because the low quality bases at the end of reads were dropped in GATK empirical quality (FIGS. 17A and 17B) calculation, the number of correct bases was calculated to show changes of overall correct bases as the read length increases (FIGS. 17C and 17D). The x-axis in FIG. 17C is the same to that in FIG. 17A and the x-axis in FIG. 17D is the same to that in FIG. 17B. Each read was aligned to the assembled reference *E coli* genome (strain ATCC 11303). A base on a read was called correct if it was the same to the aligned base on the reference genome. In FIGS. 17C and 17D, the number of correct base at each x-axis position was calculated as the number of reads that have correct bases at the position for the lane. Clearly, the reads from lane 3 in the additional sequencing after +S extension had much higher number of correct bases.

Overall, the output and quality of +S Sequencing at bases 101-200 in lane 3 were much better than without +S Extension Steps (lane 1 at bases 101-200). We also performed +S Sequencing on an additional lane (Lane 8). The results of lane 8 showed similar patterns to those of lane 3 (data not shown here).

Example 6: +S Sequencing Using Ion Torrent PGM

This example demonstrates that three nucleotide controlled extension can be performed using an Ion Torrent PGM. It also demonstrates that the commercial implementation of the controlled extension sequencing process, ±S Sequencing, can be performed using Ion Torrent as a readout device.

Materials and Methods

A "fusion" PCR construct of 176 bp insert size were designed according to Ion Torrent's guidelines (Ion Amplicon Library Preparation (Fusion Method) p/n 4468326 Rev. B). The basic sequence of the PCR construct was from the plasmid pBR322. After 25 cycles of amplification with Herculase II DNA Polymerase (Agilent #600675) the amplicons were extracted with Qiagen's Gel Extraction Kit (Qiagen #28704). Input DNA was amplified onto Ion Sphere™ Particles (ISPs) using Ion Torrent's Ion Xpress Template 200 kit (Life p/n Life #4471253). Enriched ISPs were hybridized with sequencing primer and DNA polymerase was bound according to protocol (Ion Torrent protocol 4469714 Rev. B). (Polymerase and primer from Ion's Sequencing Kit Life #4468995).

The Ion Torrent Personal Genome Machine was initialized with reagents from the sequencing kit. After initialization, the primed and polymerase-bound ISPs were loaded into a 314R chip with reagents from the Ion Sequencing 200 kit (Life #4471258) according to the 200 protocol (Life p/n 4471999 Rev. B). ISPs loaded into the chip were sequenced on the PGM with 320 nucleotide flows in Ion Torrent's SAMBA flow order. After extension, the chip was stored in a fridge in Annealing Buffer with PVP from Ion Torrent's Paired-End Sequencing Demonstrated Protocol (p/n MAN0006191; 900 ul of Annealing Buffer from sequencing kit was combined with 48 µl of 8% PVP-10).

After sequencing on the PGM, the extended sequencing primer was stripped with 0.1N NaOH and ISP-bound templates were hybridized with sequencing primer mixture (5 µl Sequencing Primer in 25 µl Annealing Buffer) at 65° C. for 5 min followed by room temperature for 15 minutes. The Personal Genome Machine was again washed and initialized and polymerase was bound onto the ISPs in the chip according to the Paired-End Demonstrated Protocol (1.5 µl of Polymerase from the Sequencing Kit was added to 6 µl of Annealing Buffer with PVP; the mixture was injected into the chip and incubated for 5 minutes). During the PGM's Inititialization 20 µl of each nucleotide was replaced by 20 µl of each of the other three nucleotides provided. For example, 20 µl of dATP was replaced with 20 µl of dCTP, 20 µl of dGTP, 20 µl of dTTP and the mixture was inserted into the dATP position on the PGM. This was repeated for each nucleotide position on the Personal Genome Machine. ISPs loaded into the chip were extended on the PGM with 16 nucleotide-triplet flows in Ion Torrent's SAMBA flow order.

After +S extension, the chip was stored in a fridge in Annealing Buffer with PVP from Ion Torrent's Paired-End Sequencing Demonstrated Protocol. After the PGM was washed and re-initialized according to the v2.0 protocol, the chip was washed 2λ with 50 µl of Enzyme Denaturation Solution (from PE Demonstrated Protocol: 1×TE, 50 mM NaCl, 2% SDS), reloaded onto the machine, and incubated with polymerase (see above). The extended chip was sequenced with 320 flows in the SAMBA flow order. Sequence calls were made on a Torrent Server using Torrent Suite v 2.0.1 (Ion Torrent/Life Technologies, Inc.). To make calls for sequencing after +S extension, a different key corresponding to the sequencing starting position of the 176mer was used. For the first sequencing, amplicons were sorted by barcode using the Torrent Suite software (all molecules of one amplicon type have the same barcode, which was different than the other amplicons included in the experiment). After +S extension, each amplicon calls a different sequence key, thus the reads generated by Torrent Suite only represented the population of amplicons that called that key. FastQ files were visually inspected for quality and read length using Prinseq online (edwards.sdsu.edu/prinseq beta/#).

Figure 18:
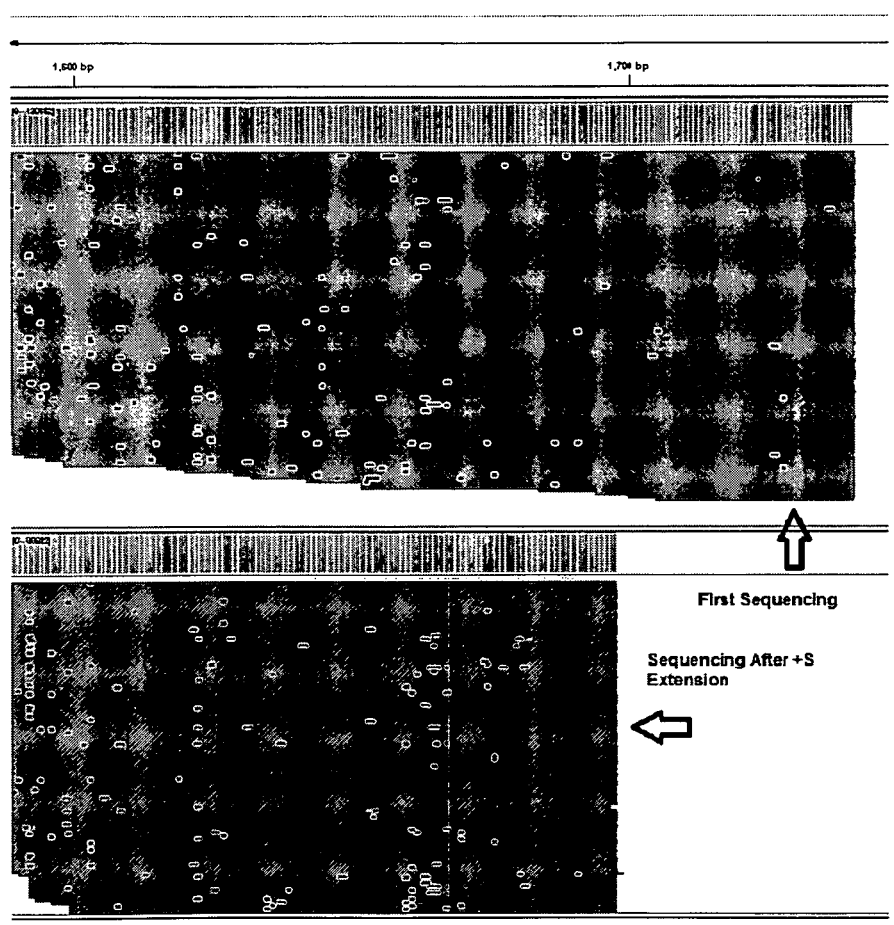
FIG. 18 is a summary of Q-scores changing over read length related to Example 6. The x-axis is read length in bp. Y-axis is measured or empirical Q-Score.

In FIG. 18, BAM files are automatically generated by Torrent Suite and visualized with IGV (www.broadinstitute.org/igv/). The alignment result clearly shows that reads after +S extension start a uniform position for one construct indicating minimum dephasing.

What is claimed is:

1. A method for sequencing a target nucleic acid, comprising the steps of:
    (a) providing a first extension primer hybridized with said target nucleic acid;
    (b) extending said first extension primer, said extending in step (b) comprises a first controlled extension comprising (i) contacting said first extension primer with a first set of nucleotides comprising three different unmodified nucleotides to a first defined length, or (ii) contacting said first extension primer with said first set of nucleotides comprising said three different unmodified nucleotides and a reversible terminator nucleotide to said first defined length, thereby said extending in step (b) produces an extended product comprising said first extension primer and an extended portion, wherein sequence of said extended portion is unknown;
    (c) using the extended product obtained in step (b) as a first sequencing primer from which to generate a first sequence read, and sequencing a first region of said target nucleic acid;
    (d) removing at least a part of said first sequence read;
    (e) providing a second extension primer hybridized with said target nucleic acid;
    (f) extending said second extension primer to a second defined length; and
    (g) sequencing a second region of said target nucleic acid, wherein said sequencing in (g) comprises providing the extended product obtained in step (f) as a second sequencing primer from which to generate a second sequence read, and wherein said second region is different from said first region.

2. The method of claim 1, wherein said removing in step (d) comprises enzymatic digestion of said first sequence read.

3. The method of claim 1, wherein said removing in step (d) comprises exonuclease digestion and wherein a base that is resistant to exonuclease digestion is incorporated to a position in said first sequence read during said sequencing in step (c).

4. The method of claim 1, wherein said first and second extension primers are the same.

5. The method of claim 1, wherein said first and second extension primers are different.

6. The method of claim 1, wherein said extending in step (b) comprises said first controlled extension comprising contacting said first extension primer with said first set of nucleotides comprising said three different unmodified nucleotides, wherein said extending in step (b) further comprises a second controlled extension after said first controlled extension, wherein said second controlled extension uses a second set of nucleotides comprising another three different unmodified nucleotides, wherein said extended product in steps (b) further comprises another extended portion after said extended portion, wherein before said second controlled extension, said first set of nucleotides used in said first controlled extension are removed.

7. The method of claim 6, wherein said first set of nucleotides used in said first controlled extension is different than said second set of nucleotides used in said second controlled extension.

8. The method of claim 6, wherein said first set of nucleotides are removed by washing and a nucleotide degrading enzyme prior to said second controlled extension.

9. The method of claim 1, wherein said first controlled extension is performed with said first set of nucleotides and said reversible terminator nucleotide to incorporate said reversible terminator nucleotide, wherein before a subsequent controlled extension, said reversible terminator nucleotide incorporated is deblocked.

10. The method of claim 1, wherein the sequence of said target nucleic acid is determined by assembling said first, second, and optionally additional sequence reads.

11. The method of claim 1, wherein said target nucleic acid is attached to a substrate.

12. The method of claim 11, wherein said substrate is a flow cell.

13. The method of claim 11, wherein said substrate comprises glass.

14. The method of claim 11, wherein said target nucleic acid is attached to said substrate via a capture probe.

15. The method of claim 1, wherein said first and second sequence reads start at positions that are at least 5, 10, 15, 20, 25, 30, 35, 40, 50, 60, 70, 80, 90, 100, 150, 175, or 200 bases apart on said target nucleic acid.

* * * * *